US009085766B2

(12) United States Patent
Crane et al.

(10) Patent No.: US 9,085,766 B2
(45) Date of Patent: Jul. 21, 2015

(54) METHODS OF PRODUCING RECOMBINANT HEME-BINDING PROTEINS AND USES THEREOF

(75) Inventors: Brian R. Crane, Ithaca, NY (US); Jawahar Sudhamsu, San Francisco, CA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/113,769

(22) Filed: May 23, 2011

(65) Prior Publication Data
US 2011/0287467 A1    Nov. 24, 2011

Related U.S. Application Data

(60) Provisional application No. 61/347,193, filed on May 21, 2010.

(51) Int. Cl.
| | | |
|---|---|---|
| C12P 21/06 | (2006.01) | |
| C12N 9/00 | (2006.01) | |
| C12N 9/88 | (2006.01) | |
| C07K 14/795 | (2006.01) | |
| C12P 21/00 | (2006.01) | |

(52) U.S. Cl.
CPC ............... *C12N 9/88* (2013.01); *C07K 14/795* (2013.01); *C12P 21/00* (2013.01); *G01N 2333/795* (2013.01); *G01N 2333/80* (2013.01); *G01N 2333/805* (2013.01); *G01N 2500/00* (2013.01)

(58) Field of Classification Search
CPC .................................. C12N 9/00; C12N 9/88
USPC ............................................ 435/69.1, 183, 6
See application file for complete search history.

(56) References Cited

PUBLICATIONS

Gao et al., J. Bacteriology, 187(15), 5084-5089, 2005.*
Graves et al., "Enhancing Stability and Expression of Recombinant Human Hemoglobin in *E. coli*: Progress in the Development of a Recombinant HBOC Source," Biochimica et Biophysica Acta 1784:1471-1479 (2008).
Ishikawa et al., "Expression of Rat Heme Oxygenase in *Escherichia coli* as a Catalytically Active, Full-Length Form That Binds to Bacterial Membranes," Eur. J. Biochem. 202:161-165 (1991).
Kery et al., "Delta-Aminolevulinate Increases Heme Saturation and Yield of Human Cystathionine Beta-Synthase Expressed in *Escherichia coli*," Archives of Biochemistry and Biophysics 316(1):24-29 (1995).
Shen et al., "Production of Unmodified Human Adult Hemoglobin in *Escherichia coli*," Proc. Nat'l. Acad. Sci. U.S.A. 90:8108-8112 (1993).
Smith et al., "Expression of a Synthetic Gene for Horseradish Peroxidase C in *Escherichia coli* and Folding and Activation of the Recombinant Enzyme with Ca2+ and Heme," J. Biol. Chem. 265(22):13335-13343 (1990).
Sudhamsu et al., "Co-Expression of Ferrochelatase Allows for Complete Heme Incorporation Into Recombinant Proteins Produced in *E. coli*," Protein Expr. Purif. 73(1):78-82 (2010).
Varnado & Goodwin, "System for the Expression of Recombinant Hemoproteins in *Escherichia coli*," Protein Expr. Purif. 35:76-83 (2004).
Weickert et al., "Optimization of Heterologous Protein Production in *Escherichia coli*," Curr. Opin. Biotechnol. 7:494-499 (1996).

\* cited by examiner

*Primary Examiner* — Maryam Monshipouri
(74) *Attorney, Agent, or Firm* — LeClairRyan, a Professional Corporation

(57) ABSTRACT

The present invention is directed to methods of producing recombinant functional heme-binding proteins with complete heme incorporation and purified preparations of the same. The present invention is further directed to methods of identifying agents that modulate the activity of heme-binding proteins.

42 Claims, 5 Drawing Sheets

Full-length NOS also benefits from FC-co-expresson

METHODS OF PRODUCING RECOMBINANT HEME-BINDING PROTEINS AND USES THEREOF

This application claims the benefit of U.S. Provisional Patent Application Ser. No. 61/347,193, filed May 21, 2010, which is hereby incorporated by reference in its entirety.

This invention was made with government support under grant number NCHE-0749997 awarded by the National Science Foundation and grant number R01GM079679 awarded by the National Institutes of Health. The government has certain rights in this invention.

FIELD OF THE INVENTION

The present invention is directed to methods of producing recombinant heme-binding proteins with complete heme incorporation and methods of using the same.

BACKGROUND OF THE INVENTION

Heme proteins encompass a wide range of functions that include electron transfer, transport and storage of oxygen, production and sensing of nitric oxide, decomposition of reactive oxygen species, catalytic oxidation of substrates, signal transduction and control of gene expression (Gray et al., "Electron Transfer in Engineered Heme Enzymes," *Faseb. J.* 11:A781-A781 (1997); Sono et al., "Heme-Containing Oxygenases," *Chem. Rev.* 96:2841-2888 (1996); Alderton et al., "Nitric Oxide Synthases Structure, Function and Inhibition," *Biochem. J.* 357:593-615 (2001); and Perutz et al., "A Haemoglobin that Acts as an Oxygen Sensor: Signalling Mechanism and Structural Basis of its Homology with PAS Domains," *Chem. Biol.* 6:R291-R297 (1999)). Under incorporation of heme into recombinant proteins can adversely influence their characterization. Evaluation of enzymatic activity is systematically underestimated if a significant proportion of the recombinant sample does not contain heme. Furthermore, proteins devoid of heme may bind another non-native cofactor with a contaminating activity of its own. A pure protein sample is usually essential for structural characterization by techniques such as X-ray crystallography, as this method often requires a single, well-folded species for crystallization. Other methods of heme protein characterization are less sensitive to the level of heme incorporation, particularly if those methods directly detect the metallocofactor (e.g., UV/Vis, EPR, and Mossbauer spectroscopy) or rely on enzymatic activity. This is both good and bad in that under incorporation may not greatly affect the analysis, but heterogeneity in the sample may go undetected.

Incomplete heme incorporation into recombinant proteins has been a frequently encountered problem (Varadarajan et al., "Cloning, Expression in *Escherichia-Coli*, and Reconstitution of Human Myoglobin," *Pro. Nat. Acad. Sci. U.S.A.* 82:5681-5684 (1985); Ishikawa et al., "Expression of Rat Heme Oxygenase in *Escherichia-Coli* as a Catalytically Active, Full-Length Form that Binds to Bacterial-Membranes," *Eur. J. Biochem.* 202:161-165 (1991); Smith et al., "Expression of a Synthetic Gene for Horseradish Peroxidase-C in *Escherichia-Coli* and Folding and Activation of the Recombinant Enzyme with Ca-2+ and Heme," *J. Biol. Chem.* 265:13335-13343 (1990); Kery et al., "Delta-Aminolevulinate Increases Heme Saturation and Yield of Human Cystathionine Beta-Synthase Expressed in *Escherichia-Coli*," *Archives Biochem. Biophys.* 31:624-29 (1995); Varnado et al., "Properties of a Novel Periplasmic Catalase-Peroxidase from *Escherichia Coli* O157: H7," *Archives Biochem. Biophys.* 42:1166-174 (2004); and Graves et al., "Enhancing Stability and Expression of Recombinant Human Hemoglobin in *E-Coli*: Progress in the Development of a Recombinant HBOC Source," *Biochimica Et Biophysica Acta-Proteins And Proteomics* 1784:1471-1479 (2008)) and thus, techniques have been developed to improve heme loading (Kery et al., "Delta-Aminolevulinate Increases Heme Saturation and Yield of Human Cystathionine Beta-Synthase Expressed in *Escherichia-Coli*," *Archives Biochem. Biophys.* 31:624'29 (1995); Varnado et al., "Properties of a Novel Periplasmic Catalase-Peroxidase from *Escherichia Coli* O157: H7," *Archives Biochem. Biophys.* 42:1166-174 (2004); Graves et al., "Enhancing Stability and Expression of Recombinant Human Hemoglobin in *E-Coli*: Progress in the Development of a Recombinant HBOC Source," *Biochimica Et Biophysica Acta-Proteins And Proteomics* 1784:1471-1479 (2008); Weickert et al., "Optimization of Heterologous Protein Production in *Escherichia Coli*," *Curr. Opinion In Biotechnol.* 7:494-499 (1996); Shen et al., "Production of Unmodified Human Adult Hemoglobin in *Escherichia-Coli*," *Pro. Nat, Acad. Sci. U.S.A.* 90:8108-8112 (1993); Varnado et al., "System for the Expression of Recombinant Hemoproteins in *Escherichia Coli*," *Prot. Exp. Pur.* 35:76-83 (2004); and Vaniado et al., "Expression of Recombinant Hemoproteins in *E. Coli* Using a Heme Protein Expression System," *Biophys. J.* 384A-384A (2007)). During induction of recombinant protein expression from highly active vectors, such as those that employ the T7-polymerase, a population of protein will fold without the heme co-factor under conditions where folding outpaces heme delivery (Weickert et al., "Blackmore, Stabilization of Apoglobin by Low Temperature Increases Yield of Soluble Recombinant Hemoglobin in *Escherichia Coli*," *App. Environ. Microbiol.* 63:4313-4320 (1997)). Supplementing the growth media with δ-amino levulinic acid (d-ALA), a precursor in the C5 heme biosynthesis pathway, increases levels of heme biosynthesis and thereby heme incorporation into the target protein (Kery et al., "Delta-Aminolevulinate Increases Heme Saturation and Yield of Human Cystathionine Beta-Synthase Expressed in *Escherichia-Coli*," *Archives Biochem. Biophys.* 31:624-29 (1995); Pcsce et al., "The 109 Residue Nerve Tissue Minihemoglobin from Cerebratulus Lacteus Highlights Striking Structural Plasticity of the Alpha-Helical Globin Fold," *Structure* 10:725-735 (2002); and Summerford et al., "Bacterial Expression of Scapharca Dimeric Hemoglobin—A Simple-Model System for Investigating Protein Cooperativity," *Prot. Engineer.* 8:593-599 (1995)). Increased heme biosynthesis rates through d-ALA supplementation does not achieve complete heme incorporation into all heme-binding proteins (Weickert et al., "Optimization of Heterologous Protein Production in *Escherichia Coli*," *Curr. Opinion In Biotechnol.* 7:494-499 (1996); Shen et al., "Production of Unmodified Human Adult Hemoglobin in *Escherichia-Coli*," *Pro. Nat. Acad. Sci. U.S.A.* 90:8108-8112 (1993); Weickert et al., "High-Fidelity Translation of Recombinant Human Hemoglobin in *Escherichia Coli*," *Appl. Environ. Microbiol.* 64:589-1593 (1998); and Wcickert et al., "A Mutation that Improves Soluble Recombinant Hemoglobin Accumulation in *Escherichia Coli* in Heme Excess," *App. Environ. Microbiol.* 65:640-647 (1999)).

Another technique for increasing home incorporation into recombinant proteins involves supplying the bacteria with hemin in the growth media. However, most *E. coli* strains do not possess an efficient heme transport system, and thus uptake of hemin relies on diffusion through the cell membrane. As a result, hemin feeding is much more effective with strains that co-express heme transport genes from other gramnegative bacteria, along with the heme-protein of interest (Graves et al., "Enhancing Stability and Expression of Recombinant Human Hemoglobin in *E-Coli*: Progress in the Development of a Recombinant HBOC Source," *Biochimica Et Biophysica Acta—Proteins And Proteomics* 1784:1471-1479 (2008); Varnado et al., "System for the Expression of Recombinant Hemoproteins in *Escherichia Coli*," *Prot. Exp. Pur.* 35:76-83 (2004); and Varnado et al., "Expression of Recombinant Hemoproteins in *E. Coli* Using a Heme Protein Expression System," *Biophys. J.* 384A-384A (2007)). For example, co-expression of the heme transport system from *P. shigelloides*, which consists of the proteins Hug A/B/C/D, TonB, and Exb B/D, while also supplementing the growth media with hemin, results in higher amounts of the target holo-protein (in this case hemoglobin) (Graves et al., "Enhancing Stability and Expression of Recombinant Human Hemoglobin in *E-Coli*: Progress in the Development of a Recombinant HBOC Source," *Biochimica Et Biophysica Acta—Proteins And Proteomics* 1784:1471-1479 (2008)). A similar method involves the co-expression of the heme receptor ChuA from *E. coli*. strain O157:H7 to enhance hemin (Varnado et al., "System for the Expression of Recombinant Hemoproteins in *Escherichia Coli*," *Prot. Exp. Pur.* 35:76-83 (2004)). This latter method also shows a significant increase in the amount of heme-loaded protein generated, although in both cases, the ratio of holoprotein:apoprotein was not evaluated. Another approach utilizes the heme-permeability of *E. coli* strain RP523, which has the hem B, porphobilinogen synthase gene disrupted to prevent native heme synthesis. All heme and/or heme analogs are procured by the cells from the growth media and incorporation is nearly stoichiometric for proteins expressed in the cytoplasm (0.8-1.0 heme/heme analog per protein) (Woodward et al., "An *Escherichia Coli* Expression-Based Method for Heme Substitution," *Nat. Methods* 4:43-45 (2007)).

Full incorporation of heme in recombinant proteins is also important for commercial applications. For example, the feasibility of employing recombinant human hemoglobin as an oxygen delivery pharmaceutical is limited by the yield of holoprotein that can be made in *E. coli* (Graves et al. "Enhancing Stability and Expression of Recombinant Human Hemoglobin in *E-Coli*: Progress in the Development of a Recombinant HBOC Source," *Biochimica Et Biophysica Acta—Proteins And Proteomics* 1784:1471-1479 (2008)). Some of the methods discussed above, while effective, require co-expression of several heme transport proteins, which could limit yields, and/or require addition of the heme cofactor.

The present invention is directed to overcoming these and other deficiencies in the art.

SUMMARY OF THE INVENTION

A first aspect of the present invention relates to a method of producing a functional recombinant heme-binding protein. This method involves co-expressing a recombinant heme-binding protein and recombinant ferrochelatase protein, or polypeptide thereof, under conditions effective for complete heme incorporation into the recombinantly produced heme-binding protein, thereby producing a functional heme-binding protein.

A second aspect of the present invention relates to a system for producing functional heme-binding proteins. This system comprises an expression system and one or more expression constructs encoding a recombinant heme-binding protein and a recombinant ferrochelatase.

A third aspect of the present invention relates to a purified preparation of recombinant functional heme-binding protein.

A fourth aspect of the present invention relates to a method of identifying an agent that modulates activity of a heme-binding protein. This method involves providing a candidate agent and providing a recombinant functional heme-binding protein. This method further involves contacting the candidate agent with the recombinant functional heme-binding protein under conditions at which the functional heme-binding protein is active and comparing the activity of the functional heme-binding protein as a result of said contacting to the activity of the heme-binding protein alone, both under said conditions at which the heme-binding protein is active. A candidate agent that modulates the activity of a heme-binding protein is identified based on said comparing.

Another aspect of the present invention relates to a method of evaluating the metabolism of an agent by a heme-binding protein. This method involves providing a candidate agent and providing a recombinant functional heme-binding protein. This method further involves contacting the candidate agent with the recombinant functional home-binding protein under conditions at which the functional heme-binding protein is active and comparing the activity of the functional heme-binding protein as a result of said contacting to the activity of the heme-binding protein alone, both under said conditions at which the heme-binding protein is active. The metabolism of the candidate agent by a heme-binding protein is evaluated based on said comparing.

The present invention is a straightforward and inexpensive method for high fidelity incorporation of heme into recombinantly overexpressed heme proteins. Co-expression of just one native protein, ferrochelatase (FC), in the presence of δ-ALA is sufficient to achieve 100% heme incorporation into three unrelated home proteins derived from different organisms. Since pre-existing methods of recombinant heme-binding protein production result in sub-optimal heme incorporation and varying amounts of protein production depending on the protein of interest, the ability to achieve complete heme incorporation as described herein, has important implications for heme-binding protein biochemical characterization, spectroscopy, structural studies, and for the production of homogeneous commercial heme-binding proteins with high activity.

BRIEF DESCRIPTION OF THE DRAWINGS

FIG. 2A(iv) shows the difference spectrum (i.e., the spectrum of FIG. 2A(ii)—the spectrum of FIG. 2A(iii)), which highlights spectral lines resulting from contamination by photosensitive protoporphyrin IX, The fluorescence spectrum shown in FIG. 2B obtained after a 397 nm excitation is representative of that of protoporphyrin IX bound to protein (see infra), and is from the same sample as FIG. 2B.

DETAILED DESCRIPTION OF THE INVENTION

Figure 1:
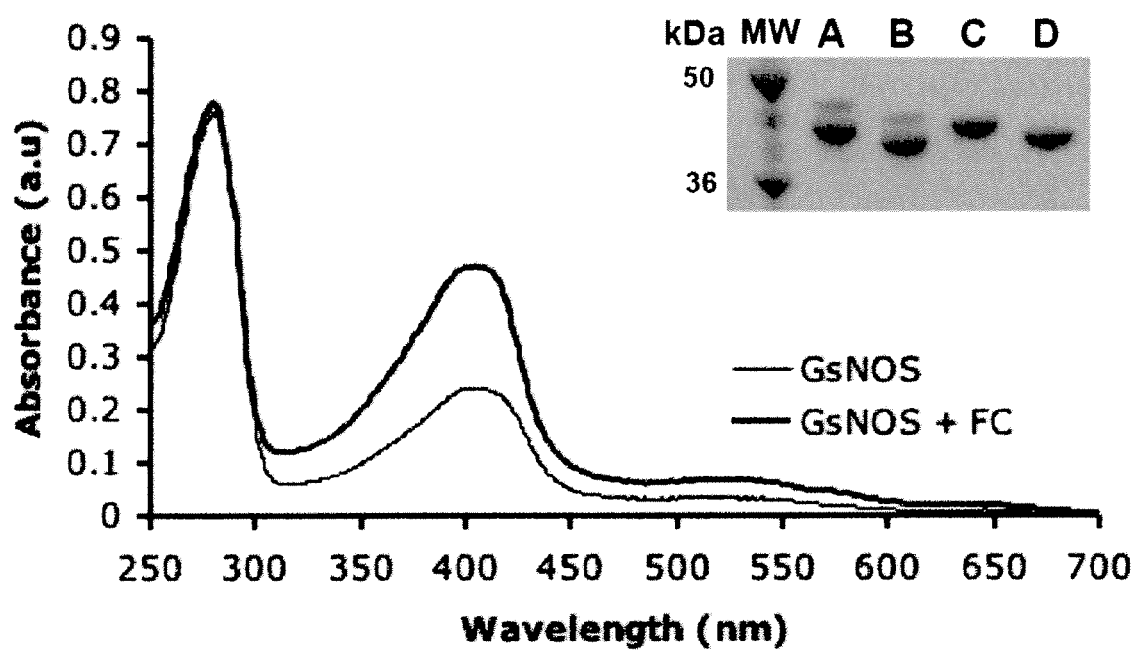
FIG. 1 shows the UV-Vis spectra of *Geobacillus stearothermophilus* nitric oxide synthase (gsNOS) expressed alone (thin line) and gsNOS expressed with ferrochelatase (FC) (thick line). Co-expression of FC results in a substantial increase in home content of gsNOS as measured by the $Abs_{403}/Abs_{280}$ ratio. This value saturates at 0.6, which indicates nearly complete heme incorporation. The inset of FIG. 1 is an immunoblot showing that GsNOS expressed by itself results in two bands on SDS-PAGE (lane A), both of which shift on His-tag cleavage (lane B), GsNOS co-expressed with FC results in just one band (lane C), that shifts on His-tag cleavage (lane D) as expected.

A first aspect of the present invention relates to a method of producing functional recombinant heme-binding proteins. This method involves co-expressing a recombinant heme-binding protein and recombinant ferrochelatase protein, or polypeptide thereof, under conditions effective for complete heme incorporation into the recombinantly produced heme-binding protein, thereby producing a functional heme-binding protein.

In accordance with this aspect of the invention, a heme-binding protein encompasses any protein that contains a heme prosthetic group either covalently or noncovalently bound to itself. Heme-binding proteins have diverse biological functions including, oxygen transport, catalysis, active membrane transport, electron transport, and sensory. The various classes of heme-binding proteins that are encompassed by the methods of the present invention include, without limitation, globins (e.g., hemoglobin, myoglobin, neuroglobin, cytoglobin, leghemoglobin), cytochromes (e.g., a-, b-, and c-types, cd1-nitrite reductase, cytochrome oxidase), transferrins (e.g., lactotransferrin, serotransferrin, melanotransferrin), bacterioferririns, hydroxylamine oxidoreductase, nitrophorins, peroxidases (e.g., lignin peroxidase), cyclooxygenases (e.g., COX-1, COX-2, COX-3, prostaglandin H synthase), catalases, cytochrome P-450s, chloroperoxidases, PAS-domain heme sensors, H-NOX heme sensors (e.g., soluble guanylate cyclase, FixL, DOS, HemAT, and CooA), heme-oxygenases, and nitric oxide synthases. The recombinant heme-binding protein produced using the methods of the present invention can be prokaryotic or eukaryotic. For example, in one embodiment of the present invention the recombinant heme-binding protein is mammalian, preferably human. In another embodiment of the present invention the recombinant heme-binding protein is bacterial. In yet another embodiment of the present invention, the recombinant heme-binding protein is fungal, preferably yeast.

Table 1 provides a non-exhaustive list of exemplary human heme-binding proteins that are suitable for production using the methods of the present invention. Table 1 identifies each heme-binding protein by its Universal Protein Resource Knowledgebase (UniProtKB)/Swiss Prot accession number, which provides the amino acid sequence of the identified protein, and the EMBL Nucleotide Database accession number, which provides the nucleotide sequence encoding the heme-binding protein. The UniProtKB/Swiss Prot and EMBL accession numbers, along with the corresponding amino acid and nucleotide sequence information for each entry in Table 1 is hereby incorporated by reference. Table 1 further identifies the UniProtKB/Swiss Prot entry name, protein names and gene names for each identified heme-binding protein.

Table 2 provides a list of lignin peroxidases, which are heme-binding proteins also suitable for production using the methods of the present invention. As described herein, lignin peroxidases metabolism the lignin of plant cell walls which facilitates the breakdown of cell wall polysaccharides to simple sugars and the subsequent conversion of these sugars to usable bio-fuel. Table 2 identifies each lignin peroxidase by its UniProtKB/Swiss Prot accession number, which provides the amino acid sequence of the protein, and the EMBL Nucleotide Database accession number, which provides the encoding nucleotide sequence. The UniProtKB/Swiss Prot and EMBL accession numbers, along with the corresponding amino acid and nucleotide sequence information for each entry in Table 2 is hereby incorporated by reference. Table 2 further identifies the UniProtKB/Swiss Prot entry name, protein names, protein family, gene names, and organism for each entry.

Traditional methods of producing recombinant heme-binding proteins generate recombinant proteins having incomplete heme incorporation. Under incorporation of heme into recombinant proteins can adversely influence their function. In contrast to these traditional methods, the methods of the present invention generate recombinant heme-binding proteins that have complete heme incorporation. Therefore, these proteins are completely functional and are more suitable for research, clinical, and commercial applications. Incomplete heme incorporation into a recombinant protein can be detected by the presence of free base porphyrin using fluorescence spectroscopy

TABLE 1

Human Heme-Binding Proteins

| Heme-binding Protein Class | UniProtKB/Swiss-Prot Accession No. | Entry name | Protein names | Gene names | EMBL Accession No. |
| --- | --- | --- | --- | --- | --- |
| Globins | Q8WWM9 | CYGB_HUMAN | Cytoglobin (Histoglobin) (HGb) (Stellate cell activation-associated protein) | CYGB STAP | AJ315162; AB057769; AK098057; CH471099; BC029798; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | P09105 | HBAT_HUMAN | Hemoglobin subunit theta-1 (Hemoglobin theta-1 chain) (Theta-1-globin) | HBQ1 | X06482; M33022; DQ431198; AE006462; BC056686; M91453; |
| | P02008 | HBAZ_HUMAN | Hemoglobin subunit zeta (HBAZ) (Hemoglobin zeta chain) (Zeta-globin) | HBZ HBZ2 | J00182; M24173; Z84721; CR456848; AE006462; CH471112; BC027892; |
| | P69905 | HBA_HUMAN | Hemoglobin subunit alpha (Alpha-globin) (Hemoglobin alpha chain) | HBA1; HBA2 | J00153; J00153; V00491; V00493; V00488; V00516; AF230076; AF525460; DQ431198; DQ431198; AF097635; AF105974; AF349571; AF536204; DQ499017; DQ499018; AK223392; AE006462; AE006462; Z84721; Z84721; BC005931; BC008572; BC032122; BC050661; BC101846; BC101848; |
| | P68871 | HBB_HUMAN | Hemoglobin subunit beta (Beta-globin) (Hemoglobin beta chain) [Cleaved into: LVV-hemorphin-7] | HBB | M25079; V00499; DQ126270; DQ126271; DQ126272; DQ126273; DQ126274; DQ126275; DQ126276; DQ126277; DQ126278; DQ126279; DQ126280; DQ126281; DQ126282; DQ126283; DQ126284; DQ126285; DQ126286; DQ126287; DQ126288; DQ126289; DQ126290; DQ126291; DQ126292; DQ126293; DQ126294; DQ126295; DQ126296; DQ126297; DQ126298; DQ126299; DQ126300; DQ126301; DQ126302; DQ126303; DQ126304; DQ126305; DQ126306; DQ126307; DQ126308; DQ126309; DQ126310; DQ126311; DQ126312; DQ126313; DQ126314; DQ126315; DQ126316; DQ126317; DQ126318; DQ126319; DQ126320; DQ126321; DQ126322; DQ126323; DQ126324; DQ126325; AF007546; AF083883; AF117710; AF181989; AF349114; AF527577; AY136510; AY163866; AY260740; AY509193; EF450778; EU694432; AK311825; CR536530; CR541913; CH471064; BC007075; U01317; V00497; V00500; L26462; L26463; L26464; L26465; L26466; L26467; L26468; L26469; L26470; L26471; L26472; L26473; L26 |
| | P02042 | HBD_HUMAN | Hemoglobin subunit delta (Delta-globin) (Hemoglobin delta chain) | HBD | U01317; V00505; AF339401; AF339402; AF339403; AF339404; AF339405; AF339406; AF339407; AF339408; AF339409; AF339410; AF339411; AF339412; AF339413; AF339414; AF339415; AF339416; AF339417; AY034468; DQ157442; BC069307; BC070282; |
| | P02100 | HBE_HUMAN | Hemoglobin subunit epsilon (Epsilon-globin) (Hemoglobin epsilon chain) | HBE1 HBE | U01317; V00508; CR541912; CH471064; BC015537; |
| | P69891 | HBG1_HUMAN | Hemoglobin subunit gamma-1 (Gamma-1-globin) (Hb F Agamma) (Hemoglobin gamma-1 chain) (Hemoglobin gamma-A chain) | HBG1 PRO2979 | M91036; M91037; V00513; V00514; J00176; U01317; AF130098; CH471064; BC010913; BC020719; AF487523; |
| | P69892 | HBG2_HUMAN | Hemoglobin subunit gamma-2 (Gamma-2-globin) (Hb F Ggamma) (Hemoglobin gamma-2 chain) (Hemoglobin gamma-G chain) | HBG2 | M91036; M91037; U01317; V00515; M15386; AY662983; AK290492; BC010914; BC029387; BC130457; BC130459; M11427; |
| | Q6B0K9 | HBM_HUMAN | Hemoglobin subunit mu (Hemoglobin mu chain) (Mu-globin) | HBM HBAP2 | AY698022; DQ431198; BC035682; |
| | P02144 | MYG_HUMAN | Myoglobin | MB | X00371; X00372; X00373; M14603; M10090; M14602; CR456516; CR541949; DQ003030; AL022334; AL049747; BC014547; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | Q9NPG2 | NGB_HUMAN | Neuroglobin | NGB | AJ245944; AJ245946; AF422796; AF422797; AC007375; AC007954; BC032509; |
| Cytochrome P450s | P15538 | C11B1_HUMAN | Cytochrome P450 11B1, mitochondrial (CYPXIB1) (Cytochrome P-450c11) (Cytochrome P450C11) (Steroid 11-beta-hydroxylase) (EC 1.14.15.4) | CYP11B1 S11BH | M32879; M32863; M32878; X55764; D16153; D16155; EU332839; CH471162; BC096287; M24667; D10169; |
| | P19099 | C11B2_HUMAN | Cytochrome P450 11B2, mitochondrial (Aldosterone synthase) (ALDOS) (EC 1.14.15.4) (EC 1.14.15.5) (Aldosterone-synthesizing enzyme) (CYPXIB2) (Cytochrome P-450Aldo) (Cytochrome P-450C18) (Steroid 18-hydroxylase) | CYP11B2 | M32881; M32864; M32880; X54741; D13752; EU326306; CH471162; |
| | A6NCC7 | C21AL_HUMAN | Putative cytochrome P450 21-like protein ENSP00000364438 | | |
| | Q4G0S4 | C27C1_HUMAN | Cytochrome P450 27C1 (EC 1.14.—.—) | CYP27C1 | AK131190; BC039307; |
| | Q6ZSU1 | C2G1L_HUMAN | Putative cytochrome P450 2G1-like protein | | AK127151; |
| | P05108 | CP11A_HUMAN | Cholesterol side-chain cleavage enzyme, mitochondrial (EC 1.14.15.6) (CYPXIA1) (Cholesterol desmolase) (Cytochrome P450 11A1) (Cytochrome P450(scc)) | CYP11A1 CYP11A | M14565; X05367; X05368; X05369; X05370; X05371; X05372; X05373; X05374; AK292300; CH471136; BC032329; X14257; M28253; |
| | P05093 | CP17A_HUMAN | Steroid 17-alpha-hydroxylase/17,20 lyase (EC 1.14.99.9) (CYPXVII) (Cytochrome P450 17A1) (Cytochrome P450-C17) (Cytochrome P450c17) (Steroid 17-alpha-monooxygenase) | CYP17A1 CYP17 S17AH | M14564; M19489; M63871; M31153; M31146; M31147; M31148; M31149; M31150; M31151; M31152; BT020000; AL358790; BC062997; BC063388; |
| | P11511 | CP19A_HUMAN | Cytochrome P450 19A1 (EC 1.14.14.1) (Aromatase) (CYPXIX) (Cytochrome P-450AROM) (Estrogen synthase) | CYP19A1 ARO1 CYAR CYP19 | M22246; X13589; M18856; J04127; Y07508; M30804; M30796; M30797; M30798; M30800; M30801; M30802; M30803; AY957953; BC107785; M28420; |
| | P04798 | CP1A1_HUMAN | Cytochrome P450 1A1 (EC 1.14.14.1) (CYPIA1) (Cytochrome P450 form 6) (Cytochrome P450-C) (Cytochrome P450-P1) | CYP1A1 | X02612; K03191; X04300; AF253322; AK223113; BC023019; M12079; AF040259; |
| | P05177 | CP1A2_HUMAN | Cytochrome P450 1A2 (EC 1.14.14.1) (CYPIA2) (Cytochrome P(3)450) (Cytochrome P450 4) (Cytochrome P450-P3) | CYP1A2 | Z00036; L00389; L00384; L00385; L00386; L00388; L00387; M31667; M31664; M31665; M31666; M12078; AF182274; AF253322; DQ022432; BC067424; BC067425; BC067426; BC067427; BC067428; M55053; |
| | Q16678 | CP1B1_HUMAN | Cytochrome P450 1B1 (EC 1.14.14.1) (CYPIB1) | CYP1B1 | U03688; U56438; AF450132; AF450131; BT019979; AY393998; BC012049; AF171066; |
| | Q6UW02 | CP20A_HUMAN | Cytochrome P450 20A1 (EC 1.14.—.—) | CYP20A1 UNQ667/PRO1301 | AY359068; AC011737; BC020616; BC033752; |
| | P08686 | CP21A_HUMAN | Steroid 21-hydroxylase (EC 1.14.99.10) (21-OHase) (Cytochrome P-450c21) (Cytochrome P450 21) (Cytochrome P450 XXI) (Cytochrome P450-C21) (Cytochrome P450-C21B) | CYP21A2 CYP21 CYP21B | M12792; M13936; M26856; X58906; BC125182; K02771; M19711; M17252; |
| | Q07973 | CP24A_HUMAN | 1,25-dihydroxyvitamin D(3) 24-hydroxylase, mitochondrial (24-OHase) | CYP24A1 CYP24 | L13286; AL138805; U60669; S67623; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | O43174 | CP26A_HUMAN | (Vitamin D(3) 24-hydroxylase) (EC 1.14.13.n4) (Cytochrome P450 24A1) (Cytochrome P450-CC24)<br>Cytochrome P450 26A1 (EC 1.14.—.—) (Cytochrome P450 retinoic acid-inactivating 1) (Cytochrome P450RAI) (hP450RAI) (Retinoic acid 4-hydroxylase) (Retinoic acid-metabolizing cytochrome) | CYP26A1 CYP26 P450RAI1 | AF005418; AL358613; CH471066; |
| | Q9NR63 | CP26B_HUMAN | Cytochrome P450 26B1 (EC 1.14.—.—) (Cytochrome P450 26A2) (Cytochrome P450 retinoic acid-inactivating 2) (Cytochrome P450RAI-2) (Retinoic acid-metabolizing cytochrome) | CYP26B1 CYP26A2 P450RAI2 | AF252297; AC007002; AK313433; BC069443; BC109205; |
| | Q8V0L0 | CP26C_HUMAN | Cytochrome P450 26C1 (EC 1.14.—.—) | CYP26C1 | AY356349; AL358613; |
| | Q02318 | CP27A_HUMAN | Sterol 26-hydroxylase, mitochondrial (EC 1.14.13.15) (5-beta-cholestane-3-alpha,7-alpha,12-alpha-triol 27-hydroxylase) (Cytochrome P-450C27/25) (Cytochrome P450 27) (Sterol 27-hydroxylase) (Vitamin D(3) 25-hydroxylase) | CYP27A1 CYP27 | M62401; X59812; AY178622; AK290418; CH471063; BC040430; BC051851; S62709; |
| | O15528 | CP27B_HUMAN | 25-hydroxyvitamin D-1 alpha hydroxylase, mitochondrial (EC 1.14.13.13) (25-OHD-1 alpha-hydroxylase) (25-hydroxyvitamin D(3) 1-alpha-hydroxylase) (VD3 1A hydroxylase) (Calcidiol 1-monooxygenase) (Cytochrome P450 subfamily XXVIIB polypeptide 1) (Cytochrome P450C1 alpha) (Cytochrome P450VD1-alpha) (Cytochrome p450 27B1) | CYP27B1 CYP1ALPHA CYP27B | AF027152; AB005038; AB005989; AB005990; AB006987; AF020192; AF246895; AY288916; |
| | P11509 | CP2A6_HUMAN | Cytochrome P450 2A6 (EC 1.14.14.1) (CYPIIA6) (Coumarin 7-hydroxylase) (Cytochrome P450 IIA3) (Cytochrome P45D(I)) | CYP2A6 CYP2A3 | X13897; X13929; X13930; M33318; AF182275; AK312964; EU135979; FJ440681; CH471126; BC096253; BC096254; BC096255; BC096256; AF326721; K03192; |
| | P20853 | CP2A7_HUMAN | Cytochrome P450 2A7 (EC 1.14.14.1) (CYPIIA7) (Cytochrome P450 IIA4) | CYP2A7 | M33317; U22029; |
| | Q16696 | CP2AD_HUMAN | Cytochrome P450 2A13 (EC 1.14.14.1) (CYPIIA13) | CYP2A13 | U22028; AF209774; AY513604; AY513605; AY513606; AY513608; AY513609; |
| | P20813 | CP2B6_HUMAN | Cytochrome P450 2B6 (EC 1.14.14.1) (CYPIIB6) (Cytochrome P450 IIB1) | CYP2B6 | M29874; AF182277; DQ298753; AC023172; |
| | P10632 | CP2C8_HUMAN | Cytochrome P450 2C8 (EC 1.14.14.1) (CYPIIC8) (Cytochrome P450 IIC2) (Cytochrome P450 MP-12) (Cytochrome P450 MP-20) (Cytochrome P450 form 1) (S-mephenytoin 4-hydroxylase) | CYP2C8 | M17397; M17398; Y00498; AK292753; AK315823; AY514490; AL359672; CH471066; BC020596; X54807; M21941; M21942; X51535; |
| | P11712 | CP2C9_HUMAN | Cytochrome P450 2C9 ((R)-limonene 6-monooxygenase) (EC 1.14.13.80) ((S)-limonene 6-monooxygenase) | CYP2C9 CYP2C10 | AY341248; AY702706; D00173; M15331; M21939; M21940; S46963; |

TABLE 1-continued

Human Heme-Binding Proteins

| Heme-binding Protein Class | UniProtKB/Swiss-Prot Accession No. | Entry name | Protein names | Gene names | EMBL Accession No. |
|---|---|---|---|---|---|
| | | | (EC 1.14.13.48) ((S)-limonene 7-monooxygenase) (EC 1.14.13.49) (CYPIIC9) (Cytochrome P-450MP) (Cytochrome P450 MP-4) (Cytochrome P450 MP-8) (Cytochrome P450 PB-1) (S-mephenytoin 4-hydroxylase) | | |
| | P33260 | CP2CI_HUMAN | Cytochrome P450 2C18 (EC 1.14.14.1) (CYPIIC18) (Cytochrome P450-6b/29c) | CYP2C18 | M61856; L16876; L16871; L16872; L16869; L16870; L16875; L16873; L16874; AK313403; AL583836; CH471066; BC069666; BC096257; BC096258; |
| | P33261 | CP2CJ_HUMAN | Cytochrome P450 2C19 ((R)-limonene 6-monooxygenase) (EC 1.14.13.80) ((S)-limonene 6-monooxygenase) (EC 1.14.13.48) ((S)-limonene 7-monooxygenase) (EC 1.14.13.49) (CYPIIC17) (CYPIIC19) (Cytochrome P450-11A) (Cytochrome P450-254C) (Mephenytoin 4-hydroxylase) | CYP2C19 | M61854; M61858; L07093; AY796203; AL583836; AL133513; AL133513; AL583836; L39098; L39097; L39102; L39099; L39100; L39101; |
| | P10635 | CP2D6_HUMAN | Cytochrome P450 2D6 (EC 1.14.14.1) (CYPIID6) (Cytochrome P450-DB1) (Debrisoquine 4-hydroxylase) | CYP2D6 CYP2DL1 | M20403; X08006; M33388; AY545216; DQ282144; DQ282145; DQ282146; DQ282151; DQ282154; DQ282155; BC075023; BC075024; |
| | P05181 | CP2E1_HUMAN | Cytochrome P450 2E1 (EC 1.14.13.—) (4-nitrophenol 2-hydroxylase) (EC 1.14.13.n7) (CYPIIE1) (Cytochrome P450-J) | CYP2E1 CYP2E | J02625; J02843; AF182276; DQ515958; AL161645; CH471211; AF084225; D50111; |
| | P24903 | CP2F1_HUMAN | Cytochrome P450 2F1 (EC 1.14.14.1) (CYPIIF1) | CYP2F1 | J02906; AF372573; AF372570; AF372571; AF372572; EF122241; EF122242; EF122243; EF122244; EF122245; |
| | P51589 | CP2J2_HUMAN | Cytochrome P450 2J2 (EC 1.14.14.1) (Arachidonic acid epoxygenase) (CYPIIJ2) | CYP2J2 | U37143; AF272142; AY426985; BC032594; |
| | Q6VVX0 | CP2R1_HUMAN | Vitamin D 25-hydroxylase (EC 1.14.13.15) (Cytochrome P450 2R1) | CYP2R1 | AY323817; BC104907; BC104909; AY800276; |
| | Q96SQ9 | CP2S1_HUMAN | Cytochrome P450 2S1 (EC 1.14.14.1) (CYPIIS1) | CYP2S1 UNQ891/PRO1906 | AF335278; AY358603; AK027605; BC033691; |
| | Q7Z449 | CP2U1_HUMAN | Cytochrome P450 2U1 (EC 1.14.14.1) | CYP2U1 | AY343323; CH471057; BC012027; BC132767; BC136483; |
| | Q8TAV3 | CP2W1_HUMAN | Cytochrome P450 2W1 (EC 1.14.14.—) (CYPIIW1) | CYP2W1 | BC025761; |
| | Q9HB55 | CP343_HUMAN | Cytochrome P450 3A43 (EC 1.14.14.1) | CYP3A43 | AF319634; AF337813; AF280107; AF280108; AF280109; AF280110; AF280111; AY390423; AY390424; AY390425; AY390426; |
| | Q9NYL5 | CP39A_HUMAN | 24-hydroxycholesterol 7-alpha-hydroxylase (Oxysterol 7-alpha-hydroxylase) (EC 1.14.13.99) (Cytochrome P450 39A1) (hCYP39A1) | CYP39A1 | AF237982; AK292283; AL591242; AL035670; AL035670; AL591242; BC010358; |
| | P08684 | CP3A4_HUMAN | Cytochrome P450 3A4 (Albendazole monooxygenase) (EC 1.14.13.32) (Albendazole sulfoxidase) (CYPIIIA3) (CYPIIIA4) (Cytochrome P450 3A3) (Cytochrome P45C HLp) (Cytochrome P450 NF-25) (Cytochrome P450-PCN1) (Nifedipine oxidase) (Quinine 3-monooxygenase) (EC 1.14.13.67) | CYP3A4 CYP3A3 | D00003; M13785; M18907; M14096; X12387; J04449; AF182273; AF280107; AF209389; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | | | (Taurochenodeoxycholate 6-alpha-hydroxylase) (EC 1.14.13.97) | | |
| | P20815 | CP3A5_HUMAN | Cytochrome P450 3A5 (EC 1.14.14.1) (CYPIIIA5) (Cytochrome P450 HLp2) (Cytochrome P450-PCN3) | CYP3A5 | J04813; AC005020; CH236956; CH471091; BC033862; AF280107; L35912; S74699; S74700; |
| | P24462 | CP3A7_HUMAN | Cytochrome P450 3A7 (EC 1.14.14.1) (CYPIIIA7) (Cytochrome P450-HFLA) | CYP3A7 | D00408; AF280107; CH236956; CH471091; BC067436; |
| | Q9Y6A2 | CP46A_HUMAN | Cholesterol 24-hydroxylase (CH24H) (EC 1.14.13.98) (Cytochrome P450 46A1) | CYP46A1 CYP46 | AF094480; BC022539; |
| | Q02928 | CP4AB_HUMAN | Cytochrome P450 4A11 (20-hydroxyeicosatetraenoic acid synthase) (20-HETE synthase) (CYP4AII) (CYPIVA11) (Cytochrome P-450HK-omega) (Cytochrome P450HL-omega) (Fatty acid omega-hydroxylase) (Lauric acid omega-hydroxylase) (EC 1.14.15.3) | CYP4A11 CYP4A2 | L04751; D26481; S67580; S67581; AF525488; AY369778; AL731892; AL731892; BC041158; X71480; |
| | Q5TCH4 | CP4AM_HUMAN | Cytochrome P450 4A22 (CYPIVA22) (Fatty acid omega-hydroxylase) (Lauric acid omega-hydroxylase) (EC 1.14.15.3) | CYP4A22 | AF208532; AY280371; AY280372; AL135960; AL135960; BC148248; |
| | P13584 | CP4B1_HUMAN | Cytochrome P450 4B1 (EC 1.14.14.1) (CYPIVB1) (Cytochrome P450-HP) | CYP4B1 | J02871; X16699; AF491285; AY064485; AY064486; AY151048; DQ518907; AL593856; AL356793; AL593856; AL356793; AL356793; AL593856; AL356793; AL593856; BC017758; |
| | P78329 | CP4F2_HUMAN | Leukotriene-B(4) omega-hydroxylase 1 (EC 1.14.13.30) (CYPIVF2) (Cytochrome P450 4F2) (Cytochrome P450-LTB-omega) (Leukotriene-B(4) 20-monooxygenase 1) | CYP4F2 | D26480; U02388; AB015306; AK290790; AF467894; AC005336; BC067437; BC067439; BC067440; AF221943; |
| | Q08477 | CP4F3_HUMAN | Leukotriene-B(4) omega-hydroxylase 2 (EC 1.14.13.30) (CYPIVF3) (Cytochrome P450 4F3) (Cytochrome P450-LTB-omega) (Leukotriene-B(4) 20-monooxygenase 2) | CYP4F3 LTB4H | D12620; D12621; AB002454; AB002461; AF054821; AY792513; |
| | P98187 | CP4F8_HUMAN | Cytochrome P450 4F8 (EC 1.14.14.1) (CYPIVF8) | CYP4F8 | AF133298; |
| | Q9HBI6 | CP4F8_HUMAN | Cytochrome P450 4F11 (EC 1.14.14.1) (CYPIVF11) | CYP4F11 | AF236085; AC005336; BC016853; |
| | Q9HCS2 | CP4FC_HUMAN | Cytochrome P450 4F12 (EC 1.14.14.1) (CYPIVF12) | CYP4F12 UNQ568/PRO1129 | AY008841; AB035130; AB035131; AY358977; AC004523; CH471106; |
| | Q6NT55 | CP4FN_HUMAN | Cytochrome P450 4F22 (EC 1.14.14.—) | CYP4F22 | AK096820; BC069351; BC093894; BC093896; |
| | Q6ZWL3 | CP4V2_HUMAN | Cytochrome P450 4V2 (EC 1.14.—.—) | CYP4V2 | AY422002; AK122600; AK126473; FJ440682; BC060857; |
| | Q8N118 | CP4X1_HUMAN | Cytochrome P450 4X1 (EC 1.14.14.1) (CYPIVX1) | CYP4X1 UNQ1929/PRO4404 | AY358537; AK098065; BC028102; |
| | Q86W10 | CP4Z1_HUMAN | Cytochrome P450 4Z1 (EC 1.14.14.1) (CYPIVZ1) | CYP4Z1 UNQ3060/PRO9882 | AY262056; AY358631; AK292175; AL450996; AL135960; AL135960; AL450996; |
| | Q8N1L4 | CP4Z2_HUMAN | Putative cytochrome P450 family member 4Z2 | CYP4Z2P | AY696295; AK097373; |
| | Q16350 | CP51A_HUMAN | Lanosterol 14-alpha demethylase (LDM) (EC 1.14.13.70) (CYPLI) (Cytochrome P450 51A1) (Cytochrome P450-14DM) (Cytochrome P45014DM) (Cytochrome P450LI) (Sterol 14-alpha demethylase) | CYP51A1 CYP51 | U23942; D55653; U51692; U51684; U51685; U51686; U51687; U51688; U51689; U51690; U51691; AK314205; AK295932; AC000120; CH236949; CH471091; CH471091; BC032322; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | P22680 | CP7A1_HUMAN | Cholesterol 7-alpha-monooxygenase (EC 1.14.13.17) (CYPVII (Cholesterol 7-alpha-hydroxylase) (Cytochrome P450 7A1) | CYP7A1 CYP7 | X56088; M93133; BC101777; BC112184; L13460; M89647; |
| | O75881 | CP7B1_HUMAN | 25-hydroxycholesterol 7-alpha-hydroxylase (Oxysterol 7-alpha-hydroxylase) (EC 1.14.13.100) (Cytochrome P450 7B1) | CYP7B1 | AF029403; AF127090; AF176805; AF176800; AF176801; AF176802; AF176803; AF176804; CH471068; BC136574; |
| | Q9UNU6 | CP8B1_HUMAN | 7-alpha-hydroxycholest-4-en-3-one 12-alpha-hydroxylase (EC 1.14.13.95) (7-alpha-hydroxy-4-cholesten-3-one 12-alpha-hydroxylase) (CYPVIIIB1) (Cytochrome P450 8B1) (Sterol 12-alpha-hydroxylase) | CYP8B1 CYP12 | AF090318; AF090320; AK315330; BC067434; BC067441; BC067442; BC067444; |
| | Q16647 | PTGIS_HUMAN | Prostacyclin synthase (EC 5.3.99.4) (Prostaglandin I2 synthase) | PTGIS CYP8 CYP8A1 | D38145; AF297048; AF297049; AF297050; AF297051; AF297052; AL118525; BC101809; BC101811; |
| | P24557 | THAS_HUMAN | Thromboxane-A synthase (TXA synthase) (TXS) (EC 5.3.99.5) (Cytochrome P450 5A1) | TBXAS1 CYP5 CYP5A1 | M80647; D34625; L36085; L36075; L36076; L36077; L36078; L36079; L36080; L36081; L36082; L36083; L36084; AF233615; AF233616; AF233617; AF233618; AF233619; AF233620; AF233621; AF233622; AF233623; AF233624; AF233625; BC041157; M74055; |
| Cytochrome b5 | Q6P9G0 | CB5D1_HUMAN | Cytochrome b5 domain-containing protein 1 | CYB5D1 | AK057061; AK289520; CH471108; CH471108; CH471108; BC060779; |
| | O43169 | CYB5B_HUMAN | Cytochrome b5 type B (Cytochrome b5 outer mitochondrial membrane isoform) | CYB5B CYB5M OMB5 | AB009282; AK291576; BC004373; BC014431; |
| | P00167 | CYB5_HUMAN | Cytochrome b5 (Microsomal cytochrome b5 type A) (MCB5) | CYB5A CYB5 | M22865; M60174; L39945; L39792; L39941; L39942; L39943; L39944; CR456990; CH471117; BC015182; |
| | Q9UMX5 | NENF_HUMAN | Neudesin (Cell immortalization-related protein 2) (Neuron-derived neurotrophic factor) (Secreted protein of unknown function) (SPUF protein) | NENF CIR2 SPUF | AB126219; AF173937; AY762102; AK223135; CH471100; BC008823; |
| | Q8WUJ1 | NEUFC_HUMAN | Neuferricin (Cytochrome b5 domain-containing protein 2) | CYB5D2 | AK172844; AK313088; CH471108; CH471108; BC020263; BC051697; |
| | O00264 | PGRC1_HUMAN | Membrane-associated progesterone receptor component 1 (mPR) | PGRMC1 HPR6.6 PGRMC | Y12711; BC034238; AJ249131; |
| | O15173 | PGRC2_HUMAN | Membrane-associated progesterone receptor component 2 (Progesterone membrane-binding protein) (Steroid receptor protein DG6) | PGRMC2 DG6 PMBP | AJ002030; DQ496105; BC016692; BC092478; |
| | D6RFH4 | D6RFH4_HUMAN | Uncharacterized protein | CYB5B | |
| Cytochrome c | P08574 | CY1_HUMAN | Cytochrome c1, heme protein, mitochondrial (Complex III subunit 4) (Complex III subunit IV) (Cytochrome b-c1 complex subunit 4) (Ubiquinol-cytochrome-c reductase complex cytochrome c1 subunit) (Cytochrome c-1) | CYC1 | M16597; J04444; CR541674; BT019798; DQ300360; BC001006; BC015616; BC020566; X06994; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | P99999 | CYC_HUMAN | Cytochrome c | CYCS CYC | M22877; BT006946; AK311836; AL713681; AC007487; CH236948; CH471073; BC005299; BC008475; BC008477; BC009578; BC009579; BC009582; BC009587; BC009602; BC009607; BC014359; BC014361; BC015130; BC016006; BC021994; BC022330; BC067222; BC068464; BC070156; BC070346; BC071761; |
| Cytochrome c oxidases | Q5JTJ3 | CA031_HUMAN | Uncharacterized protein C1orf31 | C1orf31 | AL355472; AL355472; AL355472; BC025793; BC116455; |
| | P00403 | COX2_HUMAN | Cytochrome c oxidase subunit 2 (Cytochrome c oxidase polypeptide II) | MT-CO2 COII COXII MTCO2 | V00662; J01415; X15759; M25171; D38112; U12690; U12691; U12692; U12693; U12694; AF004339; AY339402; AY339403; AY339404; AY339405; AY339406; AY339407; AY339408; AY339409; AY339410; AY339411; AY339412; AY339413; AY339414; AY339415; AY339416; AY339417; AY339418; AY339419; AY339420; AY339421; AY339422; AY339423; AY339424; AY339425; AY339426; AY339427; AY339428; AY339429; AY339430; AY339431; AY339432; AY339433; AY339434; AY339435; AY339436; AY339437; AY339438; AY339439; AY339440; AY339441; AY339442; AY339443; AY339444; AY339445; AY339446; AY339447; AY339448; AY339449; AY339450; AY339451; AY339452; AY339453; AY339454; AY339455; AY339456; AY339457; AY339458; AY339459; AY339460; AY339461; AY339462; AY339463; AY339464; AY339465; AY339466; AY339467; AY339468; AY339469; AY339470; AY339471; AY339472; AY339473; AY339474; AY339475; AY339476; AY339477; AY339478; AY339479; AY339480; AY339481; AY339482; AY339483; AY339484; AY339485; AY339486; AY339487; AY339488; AY339489; AY339490; AY339492; AY339493; AY339494; AY339495; AY339496; AY339498; AY339499; AY339500; AY339501; AY339502; AY339503; AY339504; AY339505; AY339506; AY339507; AY339508; AY339509; AY339510; AY339511; AY339512; AY339513; AY339514. |
| | P00414 | COX3_HUMAN | Cytochrome c oxidase subunit 3 (Cytochrome c oxidase polypeptide III) | MT-CO3 COIII COXIII MTCO3 | J01415; V00662; DQ654394; DQ654395; DQ654396; DQ654397; DQ654398; DQ654399; DQ654400; DQ654401; DQ654402; DQ654403; DQ654404; DQ654405; DQ654406; DQ654407; DQ654408; DQ654409; DQ654410; DQ654411; DQ654412; DQ654413; DQ654414; DQ654415; DQ654416; DQ654417; DQ654418; DQ654419; DQ654420; DQ654421; DQ654422; DQ654423; DQ654424; DQ654425; DQ654426; DQ654427; DQ654428; DQ654429; DQ654430; DQ654431; DQ654432; DQ654433; DQ654434; DQ654435; DQ654436; DQ654437; DQ654438; DQ654439; DQ654440; DQ654441; DQ654442; DQ654443; AF004341; |
| | P13073 | COX41_HUMAN | Cytochrome c oxidase subunit 4 isoform 1, mitochondrial (Cytochrome c oxidase polypeptide IV) | COX4I1 COX4 | M21575; M34600; X54802; U90915; AF005889; AF017115; AF042746; AF042744; AF042745; BT019825; AK311847; CH471114; CH471114; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | | | (Cytochrome c oxidase subunit IV isoform 1) (COX IV-1) | | BC008704; BC021236; BC062437; |
| | Q96KJ9 | COX42_HUMAN | Cytochrome c oxidase subunit 4 isoform 2, mitochondrial (Cytochrome c oxidase subunit IV isoform 2) (COX IV-2) | COX4I2 COX4L2 | AF257180; AL117381; BC057779; |
| | P20674 | COX5A_HUMAN | Cytochrome c oxidase subunit 5A, mitochondrial (Cytochrome c oxidase polypeptide Va) | COX5A | M22760; DQ987236; DQ987237; CR407649; CH471136; BC024240; |
| | P10606 | COX5B_HUWlAN | Cytochrome c oxidase subunit 5B, mitochondrial (Cytochrome c oxidase polypeptide Vb) | COX5B | M19961; M59250; BC006229; U41284; |
| | P09669 | COX6C_HUMAN | Cytochrome c oxidase subunit 6C (Cytochrome c oxidase polypeptide VIc) | COX6C | X13238; AF067637; AF067636; BT007007; AK311791; CH471060; BC000187; |
| | P24311 | COX7B_HUMAN | Cytochrome c oxidase subunit 7B, mitochondrial (Cytochrome c oxidase polypeptide VIIb) | COX7B | Z14244; BT009767; CR450332; CR542124; AK311879; AL356235; CH471104; BC018386; |
| | P15954 | COX7C_HUMAN | Cytochrome c oxidase subunit 7C, mitochondrial (Cytochrome c oxidase polypeptide VIIc) | COX7C | X16560; AF067639; AF067638; BT007098; BC001005; BC007498; |
| | O14548 | COX7R_HUMAN | Cytochrome c oxidase subunit 7A-related protein, mitochondrial (COX7a-related protein) (Cytochrome c oxidase subunit VIIa-related protein) (EB1) | COX7A2L COX7AR COX7RP | AB007618; AF127788; AY007643; BT007371; BC005251; BC007095; |
| | O60397 | COX7S_HUMAN | Putative Cytochrome c oxidase subunit 7A3, mitochondrial (Cytochrome c oxidase subunit VIIa 3) | COX7A2P2 COX7A3 COX7AL2 COX7AP2 | AC004544; |
| | P10176 | COX8A_HUMAN | Cytochrome c oxidase subunit 8A, mitochondrial (Cytochrome c oxidase polypeptide VIII-liver/heart) (Cytochrome c oxidase subunit 8-2) | COX8A COX8 COX8L | J04823; BC063025; |
| | Q7Z4L0 | COX8C_HUMAN | Cytochrome c oxidase subunit 8C, mitochondrial (Cytochrome c oxidase polypeptide 8 isoform 3) (Cytochrome c oxidase polypeptide VIII isoform 3) (COX VIII-3) (Cytochrome c oxidase subunit 8-3) | COX8C | AY161004; BC101125; BC101126; |
| | P12074 | CX6A1_HUMAN | Cytochrome c oxidase subunit 6A1, mitochondrial (Cytochrome c oxidase polypeptide VIa-liver) (Cytochrome c oxidase subunit VIA-liver) (COX VIa-L) | COX6A1 COX6AL | AK312009; AL021546; BC007723; BC070186; BC107861; X15341; |
| | Q02221 | CX6A2_HUMAN | Cytochrome c oxidase subunit 6A2, mitochondrial (Cytochrome c oxidase polypeptide VIa-heart) (COXVIAH) (Cytochrome c oxidase subunit VIA-muscle) (COX VIa-M) | COX6A2 COX6A COX6AH | M83308; U66875; BC029818; |
| | P14854 | CX6B1_HUMAN | Cytochrome c oxidase subunit 6B1 (Cytochrome c oxidase subunit VIb isoform 1) (COX VIb-1) | COX6B1 COX6B | X13923; X54473; AK312140; BT006945; CR456789; CR542137; AC002115; BC001015; BC002478; X58139; |
| | Q6YFQ2 | CX6B2_HUMAN | Cytochrome c oxidase subunit 6B2 (Cancer/testis antigen 59) (CT59) | COX6B2 | AY152398; AK057427; BC026123; BC100899; BC100900; BC100901; BC100902; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | P24310 | CX7A1_HUMAN | (Cytochrome c oxidase subunit VIb isoform 2) (COX VIb-2) (Cytochrome c oxidase subunit VIb, testis-specific isoform) Cytochrome c oxidase subunit 7A1, mitochondrial (Cytochrome c oxidase subunit VIIa-heart) (Cytochrome c oxidase subunit VIIa-H) (Cytochrome c oxidase subunit VIIa-muscle) (Cytochrome c oxidase subunit VIIa-M) | COX7A1 COX7AH | M83186; U81524; AC002984; AF037372; AF127789; AD001527; BC002757; |
| | P14406 | CX7A2_HUMAN | Cytochrome c oxidase subunit 7A2, mitochondrial (Cytochrome c oxidase subunit VIIa-liver/heart) (Cytochrome c oxidase subunit VIIa-L) (Cytochrome c oxidase subunit VIIaL) | COX7A2 COX7AL | X15822; AF134406; CR407646; CR542125; AK312154; AL080250; BC101826; BC101828; |
| | Q8TF08 | CX7B2_HUMAN | Cytochrome c oxidase subunit 7B2, mitochondrial (Cytochrome c oxidase polypeptide VIIb2) | COX7B2 | AF125109; BC035923; BC107855; |
| Prostaglandin G/H synthase | P23219 | PGH1_HUMAN | Prostaglandin G/H synthase 1 (EC 1.14.99.1) (Cyclooxygenase-1) (COX-1) (Prostaglandin H2 synthase 1) (PGH synthase 1) (PGHS-1) (PHS 1) (Prostaglandin-endoperoxide synthase 1) | PTGS1 COX1 | M31822; M31812; M31813; M31814; M31815; M31816; M31817; M31818; M31819; M31820; M31821; M59979; S78220; S36219; S36271; AF440204; AK290022; AY449688; AL162424; AL359636; AL162424; AL359636; AL162424; AL359636; AL162424; AL359636; AL162424; CH471090; BC029840; |
| | P35354 | PGH2_HUMAN | Prostaglandin G/H synthase 2 (EC 1.14.99.1) (Cyclooxygenase-2) (COX-2) (PHS II) (Prostaglandin H2 synthase 2) (PGH synthase 2) (PGHS-2) (Prostaglandin-endoperoxide synthase 2) | PTGS2 COX2 | L15326; M90100; D28235; U04636; AY462100; AY229989; AY382629; AK292167; AL033533; CH471067; BC013734; |
| Catalases | P04040 | CATA_HUMAN | Catalase (EC 1.11.1.6) | CAT | X04085; X04086; X04087; X04088; X04089; X04090; X04091; X04092; X04093; X04094; X04095; X04096; X04076; AY028632; AK291585; AK315350; AY545477; AL035079; CH471064; CH471064; BC110398; BC112217; BC112219; L13609; K02400; AK301577; |
| Peroxidases | B4DWK8 | B4DWK8_HUMAN | Catalase (EC 1.11.1.6) | | |
| | Q9NRD9 | DUOX1_HUMAN | Dual oxidase 1 (EC 1.11.1.—) (EC 1.6.3.1) (Large NOX 1) (Long NOX 1) (NADPH thyroid oxidase 1) (Thyroid oxidase 1) | DUOX1 DUOX LNOX1 THOX1 | AF230495; AF213465; AK172859; BC114628; |
| | Q9NRD8 | DUOX2_HUMAN | Dual oxidase 2 (EC 1.11.1.—) (EC 1.6.3.1) (Large NOX 2) (Long NOX 2) (NADH/NADPH thyroid oxidase p138-tox) (NADPH oxidase/peroxidase DUOX2) (NADPH thyroid oxidase 2) (Thyroid oxidase 2) (p138 thyroid oxidase) | DUOX2 LNOX2 THOX2 | AF230496; AF267981; AF181972; |
| | P11678 | PERE_HUMAN | Eosinophil peroxidase (EPO) (EC 1.11.1.7) [Cleaved into: Eosinophil peroxidase light chain; Eosinophil peroxidase heavy chain] | EPX EPER EPO EPP | M29913; M29904; M29905; M29906; M29907; M29908; M29909; M29910; M29911; M29912; DQ054598; X14346; |

TABLE 1-continued

Human Heme-Binding Proteins

| Heme-binding Protein Class | UniProtKB/ Swiss-Prot Accession No. | Entry name | Protein names | Gene names | EMBL Accession No. |
|---|---|---|---|---|---|
| | P22079 | PERL_HUMAN | Lactoperoxidase (LPO) (EC 1.11.1.7) (Salivary peroxidase) (SPO) | LPO SAPX | U39573; AY324876; BC107166; BC107167; M58151; |
| | P05164 | PERM_HUMAN | Myeloperoxidase (MPO) (EC 1.11.1.7) [Cleaved into: 89 kDa myeloperoxidase; 84 kDa myeloperoxidase; Myeloperoxidase light chain; Myeloperoxidase heavy chain] | MPO | J02694; M17176; M17170; M17171; M17172; M17173; M17174; M17175; X04876; M19507; M19508; M19508; X15377; S56200; DQ088846; CH471109; BC130476; D14466; |
| | P07202 | PERT_HUMAN | Thyroid peroxidase (TPO) (EC 1.11.1.8) | TPO | J02969; J02970; Y00406; M25715; M25702; M25703; M25704; M25705; M25706; M25707; M25708; M25709; M25710; M25711; M25712; M25713; M25714; X17358; M17755; AF439430; AF533528; AY136822; AF533529; AF533530; AF533531; M55702; M55702; |
| | A1KZ92 | PXDNL_HUMAN | Peroxidasin-like protein (EC 1.11.1.7) (Cardiac peroxidase) (Vascular peroxidase 2) | PXDNL VPO2 | EU170240; AY877349; AK058200; AK131524; CH471068; |
| | Q92626 | PXDN_HUMAN | Peroxidasin homolog (EC 1.11.1.7) (Melanoma-associated antigen MG50) (Vascular peroxidase 1) (p53-responsive gene 2 protein) | PXDN KIAA0230 MG50 PRG2 VPO VPO1 | AF200348; EF090903; D86983; CH471053; CH471053; BC098579; |
| Trans-ferrins | P02787 | TRFE_HUMAN | Serotransferrin (Transferrin) (Beta-1 metal-binding globulin) (Siderophilin) | TF PRO1400 | M12530; M17611; M17610; M17614; M17612; M17613; S95936; AF288144; AF294270; AF294271; AF288139; AF288140; AF288141; AF288142; AF288143; AY308797; DQ525716; CH471052; BC059367; M21569; M15673; M21570; X04600; AJ252279; M11372; M11361; M11362; M11363; M11364; M11365; M11366; M11367; M11368; M11369; M11370; M11371; AF118063; M12525; U88581; AF058327; M26641; |
| | P02788 | TRFL_HUMAN | Lactotransferrin (Lactoferrin) (EC 3.4.21.—) (Talalactoferrin) [Cleaved into: Kaliocin-1; Lactoferroxin-A; Lactoferroxin-B; Lactoferroxin-C] | LTF LF | X53961; U07643; M93150; M83202; M83205; M73700; AF332168; AY137470; AY165046; AY178998; BC015822; BC015823; BC022347; S52659; X52941; M18642; U95626; |
| | P08582 | TRFM_HUMAN | Melanotransferrin (Melanoma-associated antigen p97) (CD antigen CD228) | MFI2 MAP97 | M12154; BC001875; BC002623; BC007550; BC071910; |
| Nitric Oxide Synthases | P29475 | NOS1_HUMAN | Nitric oxide synthase, brain (EC 1.14.13.39) (Constitutive NOS) (NC-NOS) (NOS type I) (Neuronal NOS) (N-NOS) (nNOS) (Peptidyl-cysteine S-nitrosylase NOS1) (bNOS) | NOS1 | U17327; U17326; U17299; U17300; U17301; U17302; U17303; U17304; U17305; U17307; U17308; U17309; U17310; U17311; U17312; U17313; U17314; U17315; U17316; U17317; U17318; U17319; U17320; U17321; U17322; U17323; U17324; U17325; D16408; L02881; U31466; AY445095; |
| | P35228 | NOS2_HUMAN | Nitric oxide synthase, inducible (EC 1.14.13.39) (Hepatocyte NOS) (HEP-NOS) (Inducible NO synthase) (Inducible NOS) (iNOS) (NOS type II) (Peptidyl-cysteine S-nitrosylase NOS2) | NOS2 NOS2A | L24553; L09210; X73029; U05810; U31511; D26525; U20141; AF068236; AB022318; DQ060518; EU332854; BC130283; BC144126; S75615; |
| | P29474 | NOS3_HUMAN | Nitric oxide synthase, endothelial (EC 1.14.13.39) (Constitutive NOS) (cNOS) (EC-NOS) (Endothelial NOS) (eNOS) (NOS type III) (NOSIII) | NOS3 | M93718; M95296; L10709; L10693; L10694; L10695; L10696; L10697; L10698; L10699; L10700; L10701; L10702; L10703; L10704; L10705; L10706; L10707; L10708; L26914; X76303; X76304; X76305; X76306; X76307; X76308; X76309; X76310; |

TABLE 1-continued

Human Heme-Binding Proteins

| Heme-binding Protein Class | UniProtKB/Swiss-Prot Accession No. | Entry name | Protein names | Gene names | EMBL Accession No. |
|---|---|---|---|---|---|
| | O75713 | O75713_HUMAN | Neuronal nitric-oxide synthase isoform mu (EC 1.14.13.39) (Fragment) | nNOSmu | X76311; X76312; X76313; X76314; X76315; X76316; D26607; AF400594; AK292928; AK315213; AK223636; AF519768; EU332855; CH471173; BC063294; BC069465; L23210; S80791; AJ004918 |
| Heme-oxy-genases | P09601 | HMOX1_HUMAN | Heme oxygenase 1 (HO-1) (EC 1.14.99.3) | HMOX1 HO HO1 | X06985; CR456505; AY460337; Z82244; M23041; X14782; |
| | P30519 | HMOX2_HUMAN | Heme oxygenase 2 (HO-2) (EC 1.14.99.3) | HMOX2 HO2 | D21243; S34389; BT019788; AY771350; CH471112; CH471112; BC002396; AF051306; |

TABLE 2

Lignin Peroxidases

| UniProtKB/Swiss-Prot Accession | Entry name | Protein names | Gene names | EMBL Accession No. | Protein family | Organism |
|---|---|---|---|---|---|---|
| P28313 | PER_ARTRA | Peroxidase (EC 1.11.1.7) | | D63792; | Peroxidase family, Ligninase subfamily | *Arthromyces ramosus* |
| P28314 | PER_COPCI | Peroxidase (EC 1.11.1.7) | CIP1 | X69457; X70789; | Peroxidase family, Ligninase subfamily | *Coprinopsis cinerea* (Inky cap fungus) (*Hormographiella aspergillata*) |
| A8NK72 | PER_COPC7 | Peroxidase (EC 1.11.1.7) | CIP1 CC1G_02104 | AACS02000010; | Peroxidase family, Ligninase subfamily | *Coprinopsis cinerea* (strain Okayama-7/130/FGSC 9003) (Inky cap fungus) (*Hormographiella aspergillata*) |
| P49012 | LIG2_PHACH | Ligninase LG2 (EC 1.11.1.14) (Diarylpropane peroxidase) (Lignin peroxidase) | GLG2 LIP2 | M74229; M92644; | Peroxidase family, Ligninase subfamily | *Phanerochaete chrysosporium* (White-rot fungus) (*Sporotrichum pruinosum*) |
| P21764 | LIG3_PHACH | Ligninase LG3 (EC 1.11.1.14) (Diarylpropane peroxidase) (Lignin peroxidase) | GLG3 LIP | X51590; | Peroxidase family, Ligninase subfamily | *Phanerochaete chrysosporium* (White-rot fungus) (*Sporotrichum pruinosum*) |
| P11542 | LIG4_PHACH | Ligninase H2 (EC 1.11.1.14) (Diarylpropane peroxidase) (LG4) (Lignin peroxidase) | GLG4 LIP2 | X15599; M18743; | Peroxidase family, Ligninase subfamily | *Phanerochaete chrysosporium* (White-rot fungus) (*Sporotrichum pruinosum*) |
| P11543 | LIG5_PHACH | Ligninase LG5 (EC 1.11.1.14) (Diarylpropane peroxidase) (Lignin peroxidase) | GLG5 LIP6 | M18794; X55343; M63496; | Peroxidase family, Ligninase subfamily | *Phanerochaete chrysosporium* (White-rot fungus) (*Sporotrichum pruinosum*) |
| P50622 | LIG6_PHACH | Ligninase LG6 (EC 1.11.1.14) (Diarylpropane peroxidase) (Lignin peroxidase) | GLG6 | M80213; | Peroxidase family, Ligninase subfamily | *Phanerochaete chrysosporium* (White-rot fungus) (*Sporotrichum pruinosum*) |
| P06181 | LIG8_PHACH | Ligninase H8 (EC 1.11.1.14) (Diarylpropane peroxidase) (Lignin peroxidase) | LPOA | M37701; Y00262; M27401; M27884; | Peroxidase family, Ligninase subfamily | *Phanerochaete chrysosporium* (White-rot fungus) (*Sporotrichum pruinosum*) |
| P31837 | LIGA_PHACH | Ligninase A (EC 1.11.1.14) (Diarylpropane peroxidase) (Lignin peroxidase) | LIPA LPOB | X54257; M37701; | Peroxidase family, Ligninase subfamily | *Phanerochaete chrysosporium* (White-rot fungus) (*Sporotrichum pruinosum*) |

TABLE 2-continued

Lignin Peroxidases

| UniProtKB/Swiss-Prot Accession | Entry name | Protein names | Gene names | EMBL Accession No. | Protein family | Organism |
|---|---|---|---|---|---|---|
| P31838 | LIGB_PHACH | Ligninase B (EC 1.11.1.14) (Diarylpropane peroxidase) (Lignin peroxidase) | LIPB | X54257; | Peroxidase family, Ligninase subfamily | *Phanerochaete chrysosporium* (White-rot fungus) (*Sporotrichum pruinosum*) |
| Q02567 | PEM1_PHACH | Manganese peroxidase 1 (MnP-1) (EC 1.11.1.13) (Manganese peroxidase isozyme 1) (Peroxidase manganese-dependent 1) (Peroxidase manganese-dependent I) | MNP1 | M60672; M77513; J04624; | Peroxidase family, Ligninase subfamily | *Phanerochaete chrysosporium* (White-rot fungus) (*Sporotrichum pruinosum*) |
| P78733 | PEM3_PHACH | Manganese peroxidase H3 (EC 1.11.1.13) (Peroxidase manganese-dependent H3) | | U10306; | Peroxidase family, Ligninase subfamily | *Phanerochaete chrysosporium* (White-rot fungus) (*Sporotrichum pruinosum*) |
| P19136 | PEM4_PHACH | Manganese peroxidase H4 (EC 1.11.1.13) (MP-I) (Peroxidase manganese-dependent H4) | | J04980; | Peroxidase family, Ligninase subfamily | *Phanerochaete chrysosporium* (White-rot fungus) (*Sporotrichum pruinosum*) |
| Q9URB1 | PEM5_PHACH | Manganese peroxidase H5 (EC 1.11.1.13) (Peroxidase manganese-dependent H5) (Fragment) | | | Peroxidase family, Ligninase subfamily | *Phanerochaete chrysosporium* (White-rot fungus) (*Sporotrichum pruinosum*) |
| P20010 | LIG_PHLRA | Ligninase-3 (EC 1.11.1.14) (Diarylpropane peroxidase) (Lignin peroxidase) (Ligninase III) | | | Peroxidase family, Ligninase subfamily | *Phlebia radiata* (White-rot fungus) |
| Q70LM3 | PEM2_PHLRA | Manganese peroxidase 2 (MnP2) (EC 1.11.1.13) (Manganese peroxidase isozyme 2) | mnp2 | AJ315701; AJ566199; | Peroxidase family, Ligninase subfamily | *Phlebia radiata* (White-rot fungus) |
| Q96TS6 | PEM3_PHLRA | Manganese peroxidase 3 (MnP3) (EC 1.11.1.13) (Manganese peroxidase isozyme 3) | mnp3 | AJ310930; AJ566200; | Peroxidase family, Ligninase subfamily | *Phlebia radiata* (White-rot fungus) |
| Q9UR19 | VPL1_PLEER | Versatile peroxidase VPL1 (EC 1.11.1.16) (Versatile liquid phase peroxidase 1) | vpl1 | AF007221; AF007223; | Peroxidase family, Ligninase subfamily | *Pleurotus eryngii* (Boletus of the steppes) |
| O94753 | VPL2_PLEER | Versatile peroxidase VPL2 (EC 1.11.1.16) (Versatile liquid phase peroxidase 2) | vpl2 | AF007222; AF007224; | Peroxidase family, Ligninase subfamily | *Pleurotus eryngii* (Boletus of the steppes) |
| Q9UVP6 | VPS1_PLEER | Versatile peroxidase VPS1 (EC 1.11.1.16) (Versatile solid phase peroxidase 1) | vps1 ps1 | AF175710; | Peroxidase family, Ligninase subfamily | *Pleurotus eryngii* (Boletus of the steppes) |
| C0IW58 | LNP_TAICA | Low-redox potential peroxidase (EC 1.11.1.7) (Putative ligninolytic peroxidase) | LnP | EU289404; EU526903; | Peroxidase family, Ligninase subfamily | *Taiwanofungus camphoratus* (Poroid brown-rot fungus) (*Antrodia camphorata*) |
| P20011 | LIGA_TRAVE | Ligninase A (EC 1.11.1.14) (Diarylpropane peroxidase) (Lignin peroxidase) (Fragment) | | | Peroxidase family, Ligninase subfamily | *Trametes versicolor* (White-rot fungus) (*Coriolus versicolor*) |
| P20012 | LIGB_TRAVE | Ligninase B (EC 1.11.1.14) (Diarylpropane | | | Peroxidase family, Ligninase subfamily | *Trametes versicolor* (White-rot fungus) (*Coriolus versicolor*) |

TABLE 2-continued

Lignin Peroxidases

| UniProtKB/Swiss-Prot Accession | Entry name | Protein names | Gene names | EMBL Accession No. | Protein family | Organism |
|---|---|---|---|---|---|---|
| P20013 | LIGC_TRAVE | peroxidase) (Lignin peroxidase) (Fragment) Ligninase C (EC 1.11.1.14) (Diarylpropane peroxidase) (Lignin peroxidase) | | M64993; | Peroxidase family, Ligninase subfamily | *Trametes versicolor* (White-rot fungus) (*Coriolus versicolor*) |

(excitation at 397 nm) and resonance Raman spectroscopy. As demonstrated herein, recombinant heme-binding proteins generated using the methods of the present invention show no evidence of free base porphryin incorporation.

The recombinant ferrochelatase protein or polypeptide used in the methods of the present invention includes any recombinant ferrochelatase, or polypeptide thereof that is capable of catalyzing the insertion of ferrous iron into protoporphyrin IX to form protoheme (i.e., enzyme classification (EC) no. 4.99.1.1). Well over 400 ferrochelatases from both prokaryotes and eukaryotes have been characterized and are known in the art (see e.g., UniProtKB, (GenBank). Table 3 below provides a listing of 429 known ferrochelatase enzymes from the UniProtKB database identified by UniProtKB/Swiss-Pro Accession number, protein name, gene name, organism, EC number, and EMBL accession number. Each of the ferrochelatases listed in Table 3 is suitable for use in the present invention. The UniProtKB/Swiss Prot and EMBL accession numbers, along with the corresponding amino acid and nucleotide sequence information for each entry in Table 3 is hereby incorporated by reference. Selection of an appropriate ferrochelatase to use when carrying out the methods of the present invention is based on the recombinant heme-binding protein being produced and/or the chosen expression system.

It is to be understood that the present invention contemplates the use of any bacterial, archaeal, fungal, plant, and animal ferrochelatase known in the art. The present invention also contemplates the use of polypeptide fragments of ferrochelatase which retain iron insertion activity (i.e., suitable proteins or polypeptides have an enzyme classification of 4.99.1.1). Methods of analyzing and measuring the enzyme activity of ferrochelatase are well known in the art (see e.g., Miyamoto et al., "Overproduction, Purification, and Characterization of Ferrochelatase from *Escherichia coli*," *J. Biochem.* 115:545-551 (1994) and Taketani et al., "Rat Liver Ferrochelatase," *J. Biol. Chem.*, 256(24):12748-53 (1981), which are hereby incorporated by reference in their entirety). Therefore, suitable ferrochelatase proteins or polypeptides not identified in Table 3 can be readily identified by one of skill in the art using these enzyme activity assays.

TABLE 3

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| P42043 | HEMH1_ARATH | HEM15 At5g26030 T1N24.17 | *Arabidopsis thaliana* (Mouse-ear cress) | 4.99.1.1 | Ferrochelatase-1, chloroplastic/mitochondrial (EC 4.99.1.1) (Ferrochelatase I) (Heme synthase 1) (Protoheme ferro-lyase 1) | X73417; Y13382; AF149413; |
| Q81U22 | HEMH1_BACAN | hemH1 hemH-1 BA_1071 GBAA_1071 BAS1000 | *Bacillus anthracis* | 4.99.1.1 | Ferrochelatase 1 (EC 4.99.1.1) (Heme synthase 1) (Protoheme ferro-lyase 1) | AE016879; AE017334; AE017225; |
| Q73C98 | HEMH1_BACC1 | hemH1 BCE_1168 | *Bacillus cereus* (strain ATCC 10987) | 4.99.1.1 | Ferrochelatase 1 (EC 4.99.1.1) (Heme synthase 1) (Protoheme ferro-lyase 1) | AE017194; |
| Q81GW5 | HEMH1_BACCR | hemH1 BC_1069 | *Bacillus cereus* (strain ATCC 14579/DSM 31) | 4.99.1.1 | Ferrochelatase 1 (EC 4.99.1.1) (Heme synthase 1) (Protoheme ferro-lyase 1) | AE016877; |
| Q63ES4 | HEMH1_BACCZ | hemH1 BCE33L0987 | *Bacillus cereus* (strain ZK/E33L) | 4.99.1.1 | Ferrochelatase 1 (EC 4.99.1.1) (Heme synthase 1) (Protoheme ferro-lyase 1) | CP000001; |
| Q6HM97 | HEMH1_BACHK | hemH1 BT9727_0985 | *Bacillus thuringiensis* subsp. *konkukian* | 4.99.1.1 | Ferrochelatase 1 (EC 4.99.1.1) (Heme synthase 1) (Protoheme ferro-lyase 1) | AE017355; |
| Q69TB1 | HEMH1_ORYSJ | Os09g0297000 LOC_Os09g12560 P0592C05.24 | *Oryza sativa* subsp. *japonica* (Rice) | 4.99.1.1 | Ferrochelatase-1, chloroplastic (EC 4.99.1.1) (Ferrochelatase I) (Heme synthase 1) (Protoheme ferro-lyase 1) | AP004756; AP008215; AK068174; |
| Q8EFF4 | HEMH1_SHEON | hemH1 hemH-1 SO_2019 | *Shewanella oneidensis* | 4.99.1.1 | Ferrochelatase 1 (EC 4.99.1.1) (Heme synthase 1) (Protoheme ferro-lyase 1) | AE014299; |
| O04921 | HEMH2_ARATH | At2g30390 T06B20.24 T9D9.1 | *Arabidopsis thaliana* (Mouse-ear cress) | 4.99.1.1 | Ferrochelatase-2, chloroplastic (EC 4.99.1.1) (Heme synthase 2) (Protoheme ferro-lyase 2) | Y13156; U93215; AC002338; BT000465; BT008877; |
| Q81TU9 | HEMH2_BACAN | hemH2 hemH-2 BA_1158 GBAA_1158 BAS1075 | *Bacillus anthracis* | 4.99.1.1 | Ferrochelatase 2 (EC 4.99.1.1) (Heme synthase 2) (Protoheme ferro-lyase 2) | AE016879; AE017334; AE017225; |
| Q73C08 | HEMH2_BACC1 | hemH2 BCE_1260 | *Bacillus cereus* (strain ATCC 10987) | 4.99.1.1 | Ferrochelatase 2 (EC 4.99.1.1) (Heme synthase 2) (Protoheme ferro-lyase 2) | AE017194; |
| Q81GN7 | HEMH2_BACCR | hemH2 BC_1154 | *Bacillus cereus* (strain ATCC 14579/DSM 31) | 4.99.1.1 | Ferrochelatase 2 (EC 4.99.1.1) (Heme synthase 2) (Protoheme ferro-lyase 2) | AE016877; |
| Q63EK7 | HEMH2_BACCZ | hemH2 BCE33L1054 | *Bacillus cereus* (strain ZK/E33L) | 4.99.1.1 | Ferrochelatase 2 (EC 4.99.1.1) (Heme synthase 2) (Protoheme ferro-lyase 2) | CP000001; |
| Q6HM28 | HEMH2_BACHK | hemH2 BT9727_1056 | *Bacillus thuringiensis* subsp. *konkukian* | 4.99.1.1 | Ferrochelatase 2 (EC 4.99.1.1) (Heme synthase 2) (Protoheme ferro-lyase 2) | AE017355; |
| Q0DIV0 | HEMH2_ORYSJ | Os05g0361200 LOC_Os05g29760 P0530H10.9 P0692D12.2 | *Oryza sativa* subsp. *japonica* (Rice) | 4.99.1.1 | Ferrochelatase-2, chloroplastic (EC 4.99.1.1) (Heme synthase 2) (Protoheme ferro-lyase 2) | AC134348; AC135929; AP008211; AK073873; |
| Q8EBZ7 | HEMH2_SHEON | hemH2 hemH-2 SO_3348 | *Shewanella oneidensis* | 4.99.1.1 | Ferrochelatase 2 (EC 4.99.1.1) (Heme synthase 2) (Protoheme ferro-lyase 2) | AE014299; |
| Q6F7N0 | HEMH_ACIAD | hemH ACIAD3255 | *Acinetobacter* sp. (strain ADP1) | 4.99.1.1 | Ferrochelatase (EC 4.99.1.1) (Heme synthase) (Protoheme ferro-lyase) | CR543861; |
| B7H0X1 | HEMH_ACIB3 | hemH ABBFA_003155 | *Acinetobacter baumannii* (strain AB307-0294) | 4.99.1.1 | Ferrochelatase (EC 4.99.1.1) (Heme synthase) (Protoheme ferro-lyase) | CP001172; |
| B7I4A8 | HEMH_ACIB5 | hemH AB57_0460 | *Acinetobacter baumannii* (strain AB0057) | 4.99.1.1 | Ferrochelatase (EC 4.99.1.1) (Heme synthase) (Protoheme ferro-lyase) | CP001182; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| B2I2R9 | HEMH_ACIBC | hemH ACICU_00392 | Acinetobacter baumannii (strain ACICU) | 4.99.1.1 | Ferrochelatase (EC 4.99.1.1) (Heme synthase) (Protoheme ferro-lyase) | CP000863; |
| B0VLE0 | HEMH_ACIBS | hemH ABSDF3128 | Acinetobacter baumannii (strain SDF) | 4.99.1.1 | Ferrochelatase (EC 4.99.1.1) (Heme synthase) (Protoheme ferro-lyase) | CU468230; |
| A3M1P7 | HEMH_ACIBT | hemH A1S_0382 | Acinetobacter baumannii (strain ATCC 17978/NCDC KC 755) | 4.99.1.1 | Ferrochelatase (EC 4.99.1.1) (Heme synthase) (Protoheme ferro-lyase) | CP000521; |
| B0VEC9 | HEMH_ACIBY | hemH ABAYE3393 | Acinetobacter baumannii (strain AYE) | 4.99.1.1 | Ferrochelatase (EC 4.99.1.1) (Heme synthase) (Protoheme ferro-lyase) | CU459141; |
| C1F1C7 | HEMH_ACIC5 | hemH ACP_2433 | Acidobacterium capsulatum (strain ATCC 51196/DSM 11244/JCM 7670) | 4.99.1.1 | Ferrochelatase (EC 4.99.1.1) (Heme synthase) (Protoheme ferro-lyase) | CP001472; |
| A3N3M9 | HEMH_ACTP2 | hemH APL_1937 | Actinobacillus pleuropneumoniae serotype 5b (strain L20) | 4.99.1.1 | Ferrochelatase (EC 4.99.1.1) (Heme synthase) (Protoheme ferro-lyase) | CP000569; |
| B3H307 | HEMH_ACTP7 | hemH APP7_2025 | Actinobacillus pleuropneumoniae serotype 7 (strain AP76) | 4.99.1.1 | Ferrochelatase (EC 4.99.1.1) (Heme synthase) (Protoheme ferro-lyase) | CP001091; |
| B0BTL7 | HEMH_ACTPJ | hemH APJL_1983 | Actinobacillus pleuropneumoniae serotype 3 (strain JL03) | 4.99.1.1 | Ferrochelatase (EC 4.99.1.1) (Heme synthase) (Protoheme ferro-lyase) | CP000687; |
| A0KL51 | HEMH_AERHH | hemH AHA_2488 | Aeromonas hydrophila subsp. hydrophila (strain ATCC 7966/NCIB 9240) | 4.99.1.1 | Ferrochelatase (EC 4.99.1.1) (Heme synthase) (Protoheme ferro-lyase) | CP000462; |
| Q8U9F7 | HEMH_AGRT5 | hemH Atu3771 AGR_L_2129 | Agrobacterium tumefaciens (strain C58/ATCC 33970) | 4.99.1.1 | Ferrochelatase (EC 4.99.1.1) (Heme synthase) (Protoheme ferro-lyase) | AE007870; |
| B9JS40 | HEMH_AGRVS | hemH Avi_3712 | Agrobacterium vitis (strain S4/ATCC BAA-846) (Rhizobium vitis (strain S4)) | 4.99.1.1 | Ferrochelatase (EC 4.99.1.1) (Heme synthase) (Protoheme ferro-lyase) | CP000633; |
| Q0VSV6 | HEMH_ALCBS | hemH ABO_0294 | Alcanivorax borkumensis (strain SK2/ATCC 700651/DSM 11573) | 4.99.1.1 | Ferrochelatase (EC 4.99.1.1) (Heme synthase) (Protoheme ferro-lyase) | AM286690; |
| B6EHK1 | HEMH_ALISL | hemH VSAL_I0816 | Aliivibrio salmonicida (strain LFI1238) (Vibrio salmonicida (strain LFI1238)) | 4.99.1.1 | Ferrochelatase (EC 4.99.1.1) (Heme synthase) (Protoheme ferro-lyase) | FM178379; |
| B4S1G4 | HEMH_ALTMD | hemH MADE_00654 | Alteromonas macleodii (strain DSM 17117/Deep ecotype) | 4.99.1.1 | Ferrochelatase (EC 4.99.1.1) (Heme synthase) (Protoheme ferro-lyase) | CP001103; |
| Q3MCT9 | HEMH_ANAVT | hemH Ava_1574 | Anabaena variabilis (strain ATCC 29413/PCC 7937) | 4.99.1.1 | Ferrochelatase (EC 4.99.1.1) (Heme synthase) (Protoheme ferro-lyase) | CP000117; |
| B7GF12 | HEMH_ANOFW | hemH Aflv_2279 | Anoxybacillus flavithermus (strain DSM 21510/WK1) | 4.99.1.1 | Ferrochelatase (EC 4.99.1.1) (Heme synthase) (Protoheme ferro-lyase) | CP000922; |
| O67083 | HEMH_AQUAE | hemH aq_948 | Aquifex aeolicus | 4.99.1.1 | Ferrochelatase (EC 4.99.1.1) (Heme synthase) (Protoheme ferro-lyase) | AE000657; |
| Q5P1H1 | HEMH_AROAE | hemH AZOSEA27180 ebA4802 | Aromatoleum aromaticum (strain EbN1) (Azoarcus sp. (strain EbN1)) | 4.99.1.1 | Ferrochelatase (EC 4.99.1.1) (Heme synthase) (Protoheme ferro-lyase) | CR555306; |
| A1K8P4 | HEMH_AZOSB | hemH azo2582 | Azoarcus sp. (strain BH72) | 4.99.1.1 | Ferrochelatase (EC 4.99.1.1) (Heme synthase) (Protoheme ferro-lyase) | AM406670; |
| C1DEU1 | HEMH_AZOVD | hemH Avin_41370 | Azotobacter vinelandii (strain DJ/ATCC BAA-1303) | 4.99.1.1 | Ferrochelatase (EC 4.99.1.1) (Heme synthase) (Protoheme ferro-lyase) | CP001157; |
| Q9KDK9 | HEMH_BACHD | hemH BH1203 | Bacillus halodurans | 4.99.1.1 | Ferrochelatase (EC 4.99.1.1) (Heme synthase) (Protoheme ferro-lyase) | BA000004; |
| A8FBM6 | HEMH_BACP2 | hemH BPUM_0959 | Bacillus pumilus (strain SAFR-032) | 4.99.1.1 | Ferrochelatase (EC 4.99.1.1) (Heme synthase) (Protoheme ferro-lyase) | CP000813; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| Q5WHT1 | HEMH_BACSK | hemH ABC1539 | Bacillus clausii (strain KSM-K16) | 4.99.1.1 | Ferrochelatase (EC 4.99.1.1) (Heme synthase) (Protoheme ferro-lyase) | AP006627; |
| P32396 | HEMH_BACSU | hemH hemF BSU10130 | Bacillus subtilis | 4.99.1.1 | Ferrochelatase (EC 4.99.1.1) (Heme synthase) (Protoheme ferro-lyase) | M97208; Y14083; AL009126; |
| A9VI99 | HEMH_BACWK | hemH BcerKBAB4_0990 | Bacillus weihenstephanensis (strain KBAB4) | 4.99.1.1 | Ferrochelatase (EC 4.99.1.1) (Heme synthase) (Protoheme ferro-lyase) | CP000903; |
| Q6MHT3 | HEMH_BDEBA | hemH Bd3456 | Bdellovibrio bacteriovorus | 4.99.1.1 | Ferrochelatase (EC 4.99.1.1) (Heme synthase) (Protoheme ferro-lyase) | BX842655; |
| Q7WGI0 | HEMH_BORBR | hemH BB3938 | Bordetella bronchiseptica (Alcaligenes bronchisepticus) | 4.99.1.1 | Ferrochelatase (EC 4.99.1.1) (Heme synthase) (Protoheme ferro-lyase) | BX640449; |
| Q7W515 | HEMH_BORPA | hemH BPP3489 | Bordetella parapertussis | 4.99.1.1 | Ferrochelatase (EC 4.99.1.1) (Heme synthase) (Protoheme ferro-lyase) | BX640433; |
| Q7VVX8 | HEMH_BORPE | hemH BP2503 | Bordetella pertussis | 4.99.1.1 | Ferrochelatase (EC 4.99.1.1) (Heme synthase) (Protoheme ferro-lyase) | BX640418; |
| P22600 | HEMH_BOVIN | FECH | Bos taurus (Bovine) | 4.99.1.1 | Ferrochelatase, mitochondrial (EC 4.99.1.1) (Heme synthase) (Protoheme ferro-lyase) | L34173; |
| P28602 | HEMH_BRAJA | hemH bll7752 | Bradyrhizobium japonicum | 4.99.1.1 | Ferrochelatase (EC 4.99.1.1) (Heme synthase) (Protoheme ferro-lyase) | M92427; BA000040; |
| A5EBP8 | HEMH_BRASB | hemH BBta_1357 | Bradyrhizobium sp. (strain BTAi1/ATCC BAA-1182) | 4.99.1.1 | Ferrochelatase (EC 4.99.1.1) (Heme synthase) (Protoheme ferro-lyase) | CP000494; |
| B2SCP3 | HEMH_BRUA1 | hemH BAbS19_II00700 | Brucella abortus (strain S19) | 4.99.1.1 | Ferrochelatase (EC 4.99.1.1) (Heme synthase) (Protoheme ferro-lyase) | CP000888; |
| Q2YIS9 | HEMH_BRUA2 | hemH BAB2_0075 | Brucella abortus (strain 2308) | 4.99.1.1 | Ferrochelatase (EC 4.99.1.1) (Heme synthase) (Protoheme ferro-lyase) | AM040265; |
| P0A3D8 | HEMH_BRUAB | hemH BruAb2_0076 | Brucella abortus | 4.99.1.1 | Ferrochelatase (EC 4.99.1.1) (Heme synthase) (Protoheme ferro-lyase) | AF358663; AY027659; AE017224; |
| A9MDJ3 | HEMH_BRUC2 | hemH BCAN_B0079 | Brucella canis (strain ATCC 23365/NCTC 10854) | 4.99.1.1 | Ferrochelatase (EC 4.99.1.1) (Heme synthase) (Protoheme ferro-lyase) | CP000873; |
| C0RK28 | HEMH_BRUMB | hemH BMEA_B0080 | Brucella melitensis biotype 2 (strain ATCC 23457) | 4.99.1.1 | Ferrochelatase (EC 4.99.1.1) (Heme synthase) (Protoheme ferro-lyase) | CP001489; |
| P0A3D6 | HEMH_BRUME | hemH BMEII0018 | Brucella melitensis | 4.99.1.1 | Ferrochelatase (EC 4.99.1.1) (Heme synthase) (Protoheme ferro-lyase) | AE008918; |
| A5VTJ7 | HEMH_BRUO2 | hemH BOV_A0071 | Brucella ovis (strain ATCC 25840/63/290/NCTC 10512) | 4.99.1.1 | Ferrochelatase (EC 4.99.1.1) (Heme synthase) (Protoheme ferro-lyase) | CP000709; |
| A9WXE2 | HEMH_BRUSI | hemH BSUIS_B0081 | Brucella suis (strain ATCC 23445/NCTC 10510) | 4.99.1.1 | Ferrochelatase (EC 4.99.1.1) (Heme synthase) (Protoheme ferro-lyase) | CP000912; |
| P0A3D7 | HEMH_BRUSU | hemH BRA0076 | Brucella suis | 4.99.1.1 | Ferrochelatase (EC 4.99.1.1) (Heme synthase) (Protoheme ferro-lyase) | AE014292; |
| B1YT15 | HEMH_BURA4 | hemH BamMC406_0664 | Burkholderia ambifaria (strain MC40-6) | 4.99.1.1 | Ferrochelatase (EC 4.99.1.1) (Heme synthase) (Protoheme ferro-lyase) | CP001025; |
| Q1BYX9 | HEMH_BURCA | hemH Bcen_0262 | Burkholderia cenocepacia (strain AU 1054) | 4.99.1.1 | Ferrochelatase (EC 4.99.1.1) (Heme synthase) (Protoheme ferro-lyase) | CP000378; |
| B1JW14 | HEMH_BURCC | hemH Bcenmc03_0716 | Burkholderia cenocepacia (strain MC0-3) | 4.99.1.1 | Ferrochelatase (EC 4.99.1.1) (Heme synthase) (Protoheme ferro-lyase) | CP000958; |
| A0K4S2 | HEMH_BURCH | hemH Bcen2424_0746 | Burkholderia cenocepacia (strain HI2424) | 4.99.1.1 | Ferrochelatase (EC 4.99.1.1) (Heme synthase) (Protoheme ferro-lyase) | CP000458; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| Q0BI24 | HEMH_BURCM | hemH Bamb_0640 | Burkholderia ambifaria (strain ATCC BAA-244/AMMD) (Burkholderia cepacia (strain AMMD)) | 4.99.1.1 | Ferrochelatase (EC 4.99.1.1) (Heme synthase) (Protoheme ferro-lyase) | CP000440; |
| A3MNA4 | HEMH_BURM7 | hemH BMA10247_2211 | Burkholderia mallei (strain NCTC 10247) | 4.99.1.1 | Ferrochelatase (EC 4.99.1.1) (Heme synthase) (Protoheme ferro-lyase) | CP000548; |
| A2S570 | HEMH_BURM9 | hemH BMA10229_A1104 | Burkholderia mallei (strain NCTC 10229) | 4.99.1.1 | Ferrochelatase (EC 4.99.1.1) (Heme synthase) (Protoheme ferro-lyase) | CP000546; |
| Q62HD1 | HEMH_BURMA | hemH BMA2330 | Burkholderia mallei (Pseudomonas mallei) | 4.99.1.1 | Ferrochelatase (EC 4.99.1.1) (Heme synthase) (Protoheme ferro-lyase) | CP000010; |
| A1V0U1 | HEMH_BURMS | hemH BMASAVP1_A0495 | Burkholderia mallei (strain SAVP1) | 4.99.1.1 | Ferrochelatase (EC 4.99.1.1) (Heme synthase) (Protoheme ferro-lyase) | CP000526; |
| A3NYY2 | HEMH_BURP0 | hemH BURPS1106A_3316 | Burkholderia pseudomallei (strain 1106a) | 4.99.1.1 | Ferrochelatase (EC 4.99.1.1) (Heme synthase) (Protoheme ferro-lyase) | CP000572; |
| Q3JP06 | HEMH_BURP1 | hemH BURPS1710b_3326 | Burkholderia pseudomallei (strain 1710b) | 4.99.1.1 | Ferrochelatase (EC 4.99.1.1) (Heme synthase) (Protoheme ferro-lyase) | CP000124; |
| A3ND73 | HEMH_BURP6 | hemH BURPS668_3283 | Burkholderia pseudomallei (strain 668) | 4.99.1.1 | Ferrochelatase (EC 4.99.1.1) (Heme synthase) (Protoheme ferro-lyase) | CP000570; |
| B2JGE7 | HEMH_BURP8 | hemH Bphy_2502 | Burkholderia phymatum (strain DSM 17167/STM815) | 4.99.1.1 | Ferrochelatase (EC 4.99.1.1) (Heme synthase) (Protoheme ferro-lyase) | CP001043; |
| B2SXB8 | HEMH_BURPP | hemH Bphyt_0733 | Burkholderia phytofirmans (strain DSM 17436/PsJN) | 4.99.1.1 | Ferrochelatase (EC 4.99.1.1) (Heme synthase) (Protoheme ferro-lyase) | CP001052; |
| Q63R43 | HEMH_BURPS | hemH BPSL2831 | Burkholderia pseudomallei (Pseudomonas pseudomallei) | 4.99.1.1 | Ferrochelatase (EC 4.99.1.1) (Heme synthase) (Protoheme ferro-lyase) | BX571965; |
| Q39JD2 | HEMH_BURS3 | hemH Bcep18194_A3835 | Burkholderia sp. (strain 383) (Burkholderia cepacia (strain ATCC 17760/NCIB 9086/R18194)) | 4.99.1.1 | Ferrochelatase (EC 4.99.1.1) (Heme synthase) (Protoheme ferro-lyase) | CP000151; |
| Q2SYZ9 | HEMH_BURTA | hemH BTH_I1303 | Burkholderia thailandensis (strain E264/ATCC 700388/DSM 13276/CIP 106301) | 4.99.1.1 | Ferrochelatase (EC 4.99.1.1) (Heme synthase) (Protoheme ferro-lyase) | CP000086; |
| A4JBR6 | HEMH_BURVG | hemH Bcep1808_0707 | Burkholderia vietnamiensis (strain G4/LMG 22486) (Burkholderia cepacia (strain R1808)) | 4.99.1.1 | Ferrochelatase (EC 4.99.1.1) (Heme synthase) (Protoheme ferro-lyase) | CP000614; |
| Q145F5 | HEMH_BURXL | hemH Bxeno_A0496 Bxe_A3965 | Burkholderia xenovorans (strain LB400) | 4.99.1.1 | Ferrochelatase (EC 4.99.1.1) (Heme synthase) (Protoheme ferro-lyase) | CP000270; |
| A7ZE60 | HEMH_CAMC1 | hemH Ccon26_12120 CCC13826_0053 | Campylobacter concisus (strain 13826) | 4.99.1.1 | Ferrochelatase (EC 4.99.1.1) (Heme synthase) (Protoheme ferro-lyase) | CP000792; |
| A0RNU4 | HEMH_CAMFF | hemH CFF8240_0703 | Campylobacter fetus subsp. fetus (strain 82-40) | 4.99.1.1 | Ferrochelatase (EC 4.99.1.1) (Heme synthase) (Protoheme ferro-lyase) | CP000487; |
| A8FKS9 | HEMH_CAMJ8 | hemH C8J_0467 | Campylobacter jejuni subsp. jejuni serotype O:6 (strain 81116/NCTC 11828) | 4.99.1.1 | Ferrochelatase (EC 4.99.1.1) (Heme synthase) (Protoheme ferro-lyase) | CP000814; |
| A7H4N6 | HEMH_CAMJD | hemH JJD26997_1433 | Campylobacter jejuni subsp. doylei (strain ATCC BAA-1458/RM4099/269.97) | 4.99.1.1 | Ferrochelatase (EC 4.99.1.1) (Heme synthase) (Protoheme ferro-lyase) | CP000768; |
| Q9PI08 | HEMH_CAMJE | hemH Cj0503c | Campylobacter jejuni | 4.99.1.1 | Ferrochelatase (EC 4.99.1.1) (Heme synthase) (Protoheme ferro-lyase) | AL111168; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| A1VYL5 | HEMH_CAMJJ | hemH CJJ81176_0531 | *Campylobacter jejuni* subsp. *jejuni* serotype O:23/36 (strain 81-176) | 4.99.1.1 | Ferrochelatase (EC 4.99.1.1) (Heme synthase) (Protoheme ferro-lyase) | CP000538; |
| Q5HVR0 | HEMH_CAMJR | hemH CJE0610 | *Campylobacter jejuni* (strain RM1221) | 4.99.1.1 | Ferrochelatase (EC 4.99.1.1) (Heme synthase) (Protoheme ferro-lyase) | CP000025; |
| B8GW40 | HEMH_CAUCN | hemH CCNA_03878 | *Caulobacter crescentus* (strain NA1000/CB15N) | 4.99.1.1 | Ferrochelatase (EC 4.99.1.1) (Heme synthase) (Protoheme ferro-lyase) | CP001340; |
| P57777 | HEMH_CAUCR | hemH CC_3762 | *Caulobacter crescentus* (*Caulobacter vibrioides*) | 4.99.1.1 | Ferrochelatase (EC 4.99.1.1) (Heme synthase) (Protoheme ferro-lyase) | AF184071; AE005673; |
| O42479 | HEMH_CHICK | FECH | *Gallus gallus* (Chicken) | 4.99.1.1 | Ferrochelatase, mitochondrial (EC 4.99.1.1) (Heme synthase) (Protoheme ferro-lyase) | U68033; |
| Q5L6X6 | HEMH_CHLAB | hemH CAB136 | *Chlamydophila abortus* | 4.99.1.1 | Ferrochelatase (EC 4.99.1.1) (Heme synthase) (Protoheme ferro-lyase) | CR848038; |
| Q824K8 | HEMH_CHLCV | hemH CCA_00137 | *Chlamydophila caviae* | 4.99.1.1 | Ferrochelatase (EC 4.99.1.1) (Heme synthase) (Protoheme ferro-lyase) | AE015925; |
| Q25Z7 | HEMH_CHLFF | hemH CF0869 | *Chlamydophila felis* (strain Fe/C-56) | 4.99.1.1 | Ferrochelatase (EC 4.99.1.1) (Heme synthase) (Protoheme ferro-lyase) | AP006861; |
| Q9PIQ6 | HEMH_CHLMU | hemH TC_0772 | *Chlamydia muridarum* | 4.99.1.1 | Ferrochelatase (EC 4.99.1.1) (Heme synthase) (Protoheme ferro-lyase) | AE002160; |
| Q9Z7V1 | HEMH_CHLPN | hemH CPn_0603 CP_0144 CpB0627 | *Chlamydia pneumoniae* (*Chlamydophila pneumoniae*) | 4.99.1.1 | Ferrochelatase (EC 4.99.1.1) (Heme synthase) (Protoheme ferro-lyase) | AE001363; AE002161; BA000008; AE009440; |
| B0B858 | HEMH_CHLT2 | hemH CTL0746 | *Chlamydia trachomatis* serovar L2 (strain 434/Bu/ATCC VR-902B) | 4.99.1.1 | Ferrochelatase (EC 4.99.1.1) (Heme synthase) (Protoheme ferro-lyase) | AM884176; |
| Q3KLL2 | HEMH_CHLTA | hemH CTA_0532 | *Chlamydia trachomatis* serovar A (strain HAR-13/ATCC VR-571B) | 4.99.1.1 | Ferrochelatase (EC 4.99.1.1) (Heme synthase) (Protoheme ferro-lyase) | CP000051; |
| B0BCC3 | HEMH_CHLTB | hemH CTLon_0741 | *Chlamydia trachomatis* serovar L2b (strain UCH-1/proctitis) | 4.99.1.1 | Ferrochelatase (EC 4.99.1.1) (Heme synthase) (Protoheme ferro-lyase) | AM884177; |
| O84492 | HEMH_CHLTR | hemH CT_485 | *Chlamydia trachomatis* | 4.99.1.1 | Ferrochelatase (EC 4.99.1.1) (Heme synthase) (Protoheme ferro-lyase) | AE001273; |
| Q7NV65 | HEMH_CHRVO | hemH CV_2480 | *Chromobacterium violaceum* | 4.99.1.1 | Ferrochelatase (EC 4.99.1.1) (Heme synthase) (Protoheme ferro-lyase) | AE016825; |
| Q6NH66 | HEMH_CORDI | hemH DIP1280 | *Corynebacterium diphtheriae* | 4.99.1.1 | Ferrochelatase (EC 4.99.1.1) (Heme synthase) (Protoheme ferro-lyase) | BX248357; |
| Q8FTB1 | HEMH_COREF | hemH CE1658 | *Corynebacterium efficiens* | 4.99.1.1 | Ferrochelatase (EC 4.99.1.1) (Heme synthase) (Protoheme ferro-lyase) | BA000035; |
| A4QEC1 | HEMH_CORGB | hemH cgR_1595 | *Corynebacterium glutamicum* (strain R) | 4.99.1.1 | Ferrochelatase (EC 4.99.1.1) (Heme synthase) (Protoheme ferro-lyase) | AP009044; |
| Q8NQA1 | HEMH_CORGL | hemH Cgl1537 cg1734 | *Corynebacterium glutamicum* (*Brevibacterium flavum*) | 4.99.1.1 | Ferrochelatase (EC 4.99.1.1) (Heme synthase) (Protoheme ferro-lyase) | BA000036; BX927152; |
| B6J5R6 | HEMH_COXB1 | hemH CbuK_1987 | *Coxiella burnetii* (strain CbuK_Q154) (*Coxiella burnetii* (strain Q154)) | 4.99.1.1 | Ferrochelatase (EC 4.99.1.1) (Heme synthase) (Protoheme ferro-lyase) | CP001020; |
| B6J386 | HEMH_COXB2 | hemH CbuG_1969 | *Coxiella burnetii* (strain CbuG_Q212) (*Coxiella burnetii* (strain Q212)) | 4.99.1.1 | Ferrochelatase (EC 4.99.1.1) (Heme synthase) (Protoheme ferro-lyase) | CP001019; |
| A9KGX9 | HEMH_COXBN | hemH CBUD_2060 | *Coxiella burnetii* (strain Dugway 5J108-111) | 4.99.1.1 | Ferrochelatase (EC 4.99.1.1) (Heme synthase) (Protoheme ferro-lyase) | CP000733; |
| Q83FA4 | HEMH_COXBU | hemH CBU_0042 | *Coxiella burnetii* | 4.99.1.1 | Ferrochelatase (EC 4.99.1.1) (Heme synthase) (Protoheme ferro-lyase) | AE016828; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| P42044 | HEMH_CUCSA | HEMH | Cucumis sativus (Cucumber) | 4.99.1.1 | Ferrochelatase-2, chloroplastic (EC 4.99.1.1) (Ferrochelatase II) (Heme synthase 2) (Protoheme ferro-lyase 2) | D26106; |
| Q0KCJ6 | HEMH_CUPNH | hemH H16_A1134 | Cupriavidus necator (strain ATCC 17699/H16/DSM 428/Stanier 337) (Ralstonia eutropha) | 4.99.1.1 | Ferrochelatase (EC 4.99.1.1) (Heme synthase) (Protoheme ferro-lyase) | AM260479; |
| Q473L7 | HEMH_CUPPJ | hemH Reut_A1037 | Cupriavidus pinatubonensis (strain JMP134/LMG 1197) (Alcaligenes eutrophus) (Ralstonia eutropha) | 4.99.1.1 | Ferrochelatase (EC 4.99.1.1) (Heme synthase) (Protoheme ferro-lyase) | CP000090; |
| B3R447 | HEMH_CUPTR | hemH RALTA_A1114 | Cupriavidus taiwanensis (strain R1/LMG 19424) (Ralstonia taiwanensis (strain LMG 19424)) | 4.99.1.1 | Ferrochelatase (EC 4.99.1.1) (Heme synthase) (Protoheme ferro-lyase) | CU633749; |
| B8HK77 | HEMH_CYAP4 | hemH Cyan7425_4517 | Cyanothece sp. (strain PCC 7425/ATCC 29141) | 4.99.1.1 | Ferrochelatase (EC 4.99.1.1) (Heme synthase) (Protoheme ferro-lyase) | CP001344; |
| B7KGB9 | HEMH_CYAP7 | hemH PCC7424_2167 | Cyanothece sp. (strain PCC 7424) (Synechococcus sp. (strain ATCC 29155)) | 4.99.1.1 | Ferrochelatase (EC 4.99.1.1) (Heme synthase) (Protoheme ferro-lyase) | CP001291; |
| B7K399 | HEMH_CYAP8 | hemH PCC8801_0320 | Cyanothece sp. (strain PCC 8801) (Synechococcus sp. (strain PCC 8801/RF-1)) | 4.99.1.1 | Ferrochelatase (EC 4.99.1.1) (Heme synthase) (Protoheme ferro-lyase) | CP001287; |
| Q47HJ6 | HEMH_DECAR | hemH Daro_0929 | Dechloromonas aromatica (strain RCB) | 4.99.1.1 | Ferrochelatase (EC 4.99.1.1) (Heme synthase) (Protoheme ferro-lyase) | CP000089; |
| Q9RV98 | HEMH_DEIRA | hemH DR_1131 | Deinococcus radiodurans | 4.99.1.1 | Ferrochelatase (EC 4.99.1.1) (Heme synthase) (Protoheme ferro-lyase) | AE000513; |
| Q6APB0 | HEMH_DESPS | hemH DP1085 | Desulfotalea psychrophila | 4.99.1.1 | Ferrochelatase (EC 4.99.1.1) (Heme synthase) (Protoheme ferro-lyase) | CR522870; |
| Q54IA8 | HEMH_DICDI | hemH DDB_G0288891 | Dictyostelium discoideum (Slime mold) | 4.99.1.1 | Ferrochelatase, mitochondrial (EC 4.99.1.1) (Heme synthase) (Protoheme ferro-lyase) | AAFI02000126; |
| Q9V9S8 | HEMH_DROME | Fech CG2098 | Drosophila melanogaster (Fruit fly) | 4.99.1.1 | Ferrochelatase, mitochondrial (EC 4.99.1.1) (Heme synthase) (Protoheme ferro-lyase) | AF076220; AE014297; AE014297; AE014297; AY058251; BT001392; BT001878; CP000800; |
| A7ZJN5 | HEMH_ECO24 | hemH EcE24377A_0515 | Escherichia coli O139:H28 (strain E24377A/ETEC) | 4.99.1.1 | Ferrochelatase (EC 4.99.1.1) (Heme synthase) (Protoheme ferro-lyase) | CP000800; |
| B7UKF5 | HEMH_ECO27 | hemH E2348_C_0410 | Escherichia coli O127:H6 (strain E2348/69/EPEC) | 4.99.1.1 | Ferrochelatase (EC 4.99.1.1) (Heme synthase) (Protoheme ferro-lyase) | FM180568; |
| B7MDZ7 | HEMH_ECO45 | hemH ECS88_0472 | Escherichia coli O45:K1 (strain S88/ExPEC) | 4.99.1.1 | Ferrochelatase (EC 4.99.1.1) (Heme synthase) (Protoheme ferro-lyase) | CU928161; |
| B7L7A0 | HEMH_ECO55 | hemH EC55989_0488 | Escherichia coli (strain 55989/EAEC) | 4.99.1.1 | Ferrochelatase (EC 4.99.1.1) (Heme synthase) (Protoheme ferro-lyase) | CU928145; |
| Q8XD39 | HEMH_ECO57 | hemH Z0592 ECs0528 | Escherichia coli O157:H7 | 4.99.1.1 | Ferrochelatase (EC 4.99.1.1) (Heme synthase) (Protoheme ferro-lyase) | AE005174; BA000007; |
| B5Z3Y6 | HEMH_ECO5E | hemH ECH74115_0568 | Escherichia coli O157:H7 (strain EC4115/EHEC) | 4.99.1.1 | Ferrochelatase (EC 4.99.1.1) (Heme synthase) (Protoheme ferro-lyase) | CP001164; |
| B7NIF5 | HEMH_ECO71 | hemH ECIAI39_0196 | Escherichia coli O7:K1 (strain IAI39/ExPEC) | 4.99.1.1 | Ferrochelatase (EC 4.99.1.1) (Heme synthase) (Protoheme ferro-lyase) | CU928164; |
| B7MQJ0 | HEMH_ECO81 | hemH ECED1_0498 | Escherichia coli O81 (strain ED1a) | 4.99.1.1 | Ferrochelatase (EC 4.99.1.1) (Heme synthase) (Protoheme ferro-lyase) | CU928162; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| B7M3W7 | HEMH_ECO8A | hemH ECIAI1_0478 | Escherichia coli O8 (strain IAI1) | 4.99.1.1 | Ferrochelatase (EC 4.99.1.1) (Heme synthase) (Protoheme ferro-lyase) | CU928160; |
| C4ZUS9 | HEMH_ECOBW | hemH BWG_0356 | Escherichia coli (strain K12/MC4100/BW2952) | 4.99.1.1 | Ferrochelatase (EC 4.99.1.1) (Heme synthase) (Protoheme ferro-lyase) | CP001396; |
| B1XFR2 | HEMH_ECODH | hemH ECDH10B_0431 | Escherichia coli (strain K12/DH10B) | 4.99.1.1 | Ferrochelatase (EC 4.99.1.1) (Heme synthase) (Protoheme ferro-lyase) | CP000948; |
| A7ZXD3 | HEMH_ECOHS | hemH EcHS_A0552 | Escherichia coli O9:H4 (strain HS) | 4.99.1.1 | Ferrochelatase (EC 4.99.1.1) (Heme synthase) (Protoheme ferro-lyase) | CP000802; |
| A1A8E1 | HEMH_ECOK1 | hemH Ecok1_04370 APECO1_1540 | Escherichia coli O1:K1/APEC | 4.99.1.1 | Ferrochelatase (EC 4.99.1.1) (Heme synthase) (Protoheme ferro-lyase) | CP000468; |
| Q0TKG6 | HEMH_ECOL5 | hemH ECP_0536 | Escherichia coli O6:K15:H31 (strain 536/UPEC) | 4.99.1.1 | Ferrochelatase (EC 4.99.1.1) (Heme synthase) (Protoheme ferro-lyase) | CP000247; |
| Q8FK83 | HEMH_ECOL6 | hemH c0595 | Escherichia coli O6 | 4.99.1.1 | Ferrochelatase (EC 4.99.1.1) (Heme synthase) (Protoheme ferro-lyase) | AE014075; |
| B1IZB9 | HEMH_ECOLC | hemH EcolC_3141 | Escherichia coli (strain ATCC 8739/DSM 1576/Crooks) | 4.99.1.1 | Ferrochelatase (EC 4.99.1.1) (Heme synthase) (Protoheme ferro-lyase) | CP000946; |
| P23871 | HEMH_ECOLI | hemH popA visA b0475 JW0464 | Escherichia coli (strain K12) | 4.99.1.1 | Ferrochelatase (EC 4.99.1.1) (Heme synthase) (Protoheme ferro-lyase) | D90259; U82664; U00096; AP009048; |
| B7N928 | HEMH_ECOLU | hemH ECUMN_0514 | Escherichia coli O17:K52:H18 (strain UMN026/ExPEC) | 4.99.1.1 | Ferrochelatase (EC 4.99.1.1) (Heme synthase) (Protoheme ferro-lyase) | CU928163; |
| B6I0C7 | HEMH_ECOSE | hemH ECSE_0500 | Escherichia coli (strain SE11) | 4.99.1.1 | Ferrochelatase (EC 4.99.1.1) (Heme synthase) (Protoheme ferro-lyase) | AP009240; |
| B1LJN3 | HEMH_ECOSM | hemH EcSMS35_0520 | Escherichia coli (strain SMS-3-5/SECEC) | 4.99.1.1 | Ferrochelatase (EC 4.99.1.1) (Heme synthase) (Protoheme ferro-lyase) | CP000970; |
| Q1RF60 | HEMH_ECOUT | hemH UTI89_C0503 | Escherichia coli (strain UTI89/UPEC) | 4.99.1.1 | Ferrochelatase (EC 4.99.1.1) (Heme synthase) (Protoheme ferro-lyase) | CP000243; |
| C5BD17 | HEMH_EDW19 | hemH NT01EI_1124 | Edwardsiella ictaluri (strain 93-146) | 499.1.1 | Ferrochelatase (EC 4.99.1.1) (Heme synthase) (Protoheme ferro-lyase) | CP001600; |
| A4W7F9 | HEMH_ENT38 | hemH Ent638_0955 | Enterobacter sp. (strain 638) | 4.99.1.1 | Ferrochelatase (EC 4.99.1.1) (Heme synthase) (Protoheme ferro-lyase) | CP000653; |
| Q833G5 | HEMH_ENTFA | hemH EF_1989 | Enterococcus faecalis (Streptococcus faecalis) | 4.99.1.1 | Ferrochelatase (EC 4.99.1.1) (Heme synthase) (Protoheme ferro-lyase) | AE016830; |
| A7MNM8 | HEMH_ENTS8 | hemH ESA_02788 | Enterobacter sakazakii (strain ATCC BAA-894) | 4.99.1.1 | Ferrochelatase (EC 4.99.1.1) (Heme synthase) (Protoheme ferro-lyase) | CP000783; |
| Q6D7Z4 | HEMH_ERWCT | hemH ECA1181 | Erwinia carotovora subsp. atroseptica (Pectobacterium atrosepticum) | 4.99.1.1 | Ferrochelatase (EC 4.99.1.1) (Heme synthase) (Protoheme ferro-lyase) | BX950851; |
| B2VHX1 | HEMH_ERWT9 | hemH ETA_24640 | Erwinia tasmaniensis (strain DSM 17950/Et1/99) | 4.99.1.1 | Ferrochelatase (EC 4.99.1.1) (Heme synthase) (Protoheme ferro-lyase) | CU468135; |
| B7LV14 | HEMH_ESCF3 | hemH EFER_0525 | Escherichia fergusonii (strain ATCC 35469/DSM 13698/CDC 0568-73) | 4.99.1.1 | Ferrochelatase (EC 4.99.1.1) (Heme synthase) (Protoheme ferro-lyase) | CU928158; |
| Q0RH75 | HEMH_FRAAA | hemH FRAAL4516 | Frankia alni (strain ACN14a) | 4.99.1.1 | Ferrochelatase (EC 4.99.1.1) (Heme synthase) (Protoheme ferro-lyase) | CT573213; |
| Q14H85 | HEMH_FRAT1 | hemH FTF1138 | Francisella tularensis subsp. tularensis (strain FSC 198) | 4.99.1.1 | Ferrochelatase (EC 4.99.1.1) (Heme synthase) (Protoheme ferro-lyase) | AM286280; |
| A7NBJ3 | HEMH_FRATF | hemH FTA_0870 | Francisella tularensis subsp. holarctica (strain FTNF002-00/FTA) | 4.99.1.1 | Ferrochelatase (EC 4.99.1.1) (Heme synthase) (Protoheme ferro-lyase) | CP000803; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| Q2A406 | HEMH_FRATH | hemH FTL_0821 | *Francisella tularensis* subsp. *holarctica* (strain LVS) | 4.99.1.1 | Ferrochelatase (EC 4.99.1.1) (Heme synthase) (Protoheme ferro-lyase) | AM233362; |
| B2SDE2 | HEMH_FRATM | hemH FTM_1306 | *Francisella tularensis* subsp. *mediasiatica* (strain FSC147) | 4.99.1.1 | Ferrochelatase (EC 4.99.1.1) (Heme synthase) (Protoheme ferro-lyase) | CP000915; |
| A0Q6Z1 | HEMH_FRATN | hemH FTN_1120 | *Francisella tularensis* subsp. *novicida* (strain U112) | 4.99.1.1 | Ferrochelatase (EC 4.99.1.1) (Heme synthase) (Protoheme ferro-lyase) | CP000439; |
| Q0BME1 | HEMH_FRATO | hemH FTH_0813 | *Francisella tularensis* subsp. *holarctica* (strain OSU18) | 4.99.1.1 | Ferrochelatase (EC 4.99.1.1) (Heme synthase) (Protoheme ferro-lyase) | CP000437; |
| Q5NFT3 | HEMH_FRATT | hemH FTT_1138 | *Francisella tularensis* subsp. *tularensis* | 4.99.1.1 | Ferrochelatase (EC 4.99.1.1) (Heme synthase) (Protoheme ferro-lyase) | AJ749949; |
| A4IYH5 | HEMH_FRATW | hemH FTW_1172 | *Francisella tularensis* subsp. *tularensis* (strain WY96-3418) | 4.99.1.1 | Ferrochelatase (EC 4.99.1.1) (Heme synthase) (Protoheme ferro-lyase) | CP000608; |
| B5EJ44 | HEMH_GEOBB | hemH Gbem_0039 | *Geobacter bemidjiensis* (strain Bem/ATCC BAA-1014/DSM 16622) | 4.99.1.1 | Ferrochelatase (EC 4.99.1.1) (Heme synthase) (Protoheme ferro-lyase) | CP001124; |
| Q5L283 | HEMH_GEOKA | hemH GK0662 | *Geobacillus kaustophilus* | 4.99.1.1 | Ferrochelatase (EC 4.99.1.1) (Heme synthase) (Protoheme ferro-lyase) | BA000043; |
| Q39ZQ5 | HEMH_GEOMG | hemH Gmet_0019 | *Geobacter metallireducens* (strain GS-15/ATCC 53774/DSM 7210) | 4.99.1.1 | Ferrochelatase (EC 4.99.1.1) (Heme synthase) (Protoheme ferro-lyase) | CP000148; |
| B9M326 | HEMH_GEOSF | hemH Geob_1076 | *Geobacter* sp. (strain FRC-32) | 4.99.1.1 | Ferrochelatase (EC 4.99.1.1) (Heme synthase) (Protoheme ferro-lyase) | CP001390; |
| Q747F5 | HEMH_GEOSL | hemH GSU3312 | *Geobacter sulfurreducens* | 4.99.1.1 | Ferrochelatase (EC 4.99.1.1) (Heme synthase) (Protoheme ferro-lyase) | AE017180; |
| C6E7U2 | HEMH_GEOSM | hemH GM21_0038 | *Geobacter* sp. (strain M21) | 4.99.1.1 | Ferrochelatase (EC 4.99.1.1) (Heme synthase) (Protoheme ferro-lyase) | CP001661; |
| C5D6M6 | HEMH_GEOSW | hemH GWCH70_0650 | *Geobacillus* sp. (strain WCH70) | 4.99.1.1 | Ferrochelatase (EC 4.99.1.1) (Heme synthase) (Protoheme ferro-lyase) | CP001638; |
| A4IKU8 | HEMH_GEOTN | hemH GTNG_0570 | *Geobacillus thermodenitrificans* (strain NG80-2) | 4.99.1.1 | Ferrochelatase (EC 4.99.1.1) (Heme synthase) (Protoheme ferro-lyase) | CP000557; |
| A5GDG7 | HEMH_GEOUR | hemH Gura_0173 | *Geobacter uraniireducens* (strain Rf4) (*Geobacter uraniumreducens*) | 4.99.1.1 | Ferrochelatase (EC 4.99.1.1) (Heme synthase) (Protoheme ferro-lyase) | CP000698; |
| Q7NMC7 | HEMH_GLOVI | hemH gll0839 | *Gloeobacter violaceus* | 4.99.1.1 | Ferrochelatase (EC 4.99.1.1) (Heme synthase) (Protoheme ferro-lyase) | BA000045; |
| Q5FSJ9 | HEMH_GLUOX | hemH GOX0874 | *Gluconobacter oxydans* (*Gluconobacter suboxydans*) | 4.99.1.1 | Ferrochelatase (EC 4.99.1.1) (Heme synthase) (Protoheme ferro-lyase) | CP000009; |
| Q4QLD6 | HEMH_HAEI8 | hemH NTHI1329 | *Haemophilus influenzae* (strain 86-028NP) | 4.99.1.1 | Ferrochelatase (EC 4.99.1.1) (Heme synthase) (Protoheme ferro-lyase) | CP000057; |
| A5UCU6 | HEMH_HAEIE | hemH CGSHiEE_06240 | *Haemophilus influenzae* (strain PittEE) | 4.99.1.1 | Ferrochelatase (EC 4.99.1.1) (Heme synthase) (Protoheme ferro-lyase) | CP000671; |
| P43868 | HEMH_HAEIN | hemH visA HI_1160 | *Haemophilus influenzae* (strain ATCC 51907/DSM 11121/KW20/Rd) | 4.99.1.1 | Ferrochelatase (EC 4.99.1.1) (Heme synthase) (Protoheme ferro-lyase) | L42023; |
| C4K332 | HEMH_HAMD5 | hemH HDEF_0207 | *Hamiltonella defensa* subsp. *Acyrthosiphon pisum* (strain 5AT) | 4.99.1.1 | Ferrochelatase (EC 4.99.1.1) (Heme synthase) (Protoheme ferro-lyase) | CP001277; |
| Q17YG0 | HEMH_HELAH | hemH Hac_0490 | *Helicobacter acinonychis* (strain Sheeba) | 4.99.1.1 | Ferrochelatase (EC 4.99.1.1) (Heme synthase) (Protoheme ferro-lyase) | AM260522; |
| Q7VHH1 | HEMH_HELHP | hemH HH_0996 | *Helicobacter hepaticus* | 4.99.1.1 | Ferrochelatase (EC 4.99.1.1) (Heme synthase) (Protoheme ferro-lyase) | AE017125; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| B6JMR9 | HEMH_HELP2 | hemH HPP12_1045 | Helicobacter pylori (strain P12) | 4.99.1.1 | Ferrochelatase (EC 4.99.1.1) (Heme synthase) (Protoheme ferro-lyase) | CP001217; |
| B5Z875 | HEMH_HELPG | hemH HPG27_1021 | Helicobacter pylori (strain G27) | 4.99.1.1 | Ferrochelatase (EC 4.99.1.1) (Heme synthase) (Protoheme ferro-lyase) | CP001173; |
| Q1CSI9 | HEMH_HELPH | hemH HPAG1_1016 | Helicobacter pylori (strain HPAG1) | 4.99.1.1 | Ferrochelatase (EC 4.99.1.1) (Heme synthase) (Protoheme ferro-lyase) | CP000241; |
| Q9ZKD4 | HEMH_HELPJ | hemH jhp_1005 | Helicobacter pylori J99 (Campylobacter pylori J99) | 4.99.1.1 | Ferrochelatase (EC 4.99.1.1) (Heme synthase) (Protoheme ferro-lyase) | AE001439; |
| B2UUI4 | HEMH_HELPS | hemH HPSH_05535 | Helicobacter pylori (strain Shi470) | 4.99.1.1 | Ferrochelatase (EC 4.99.1.1) (Heme synthase) (Protoheme ferro-lyase) | CP001072; |
| P56107 | HEMH_HELPY | hemH HP_0376 | Helicobacter pylori (Campylobacter pylori) | 4.99.1.1 | Ferrochelatase (EC 4.99.1.1) (Heme synthase) (Protoheme ferro-lyase) | AE000511; |
| A9B546 | HEMH_HERA2 | hemH Haur_3547 | Herpetosiphon aurantiacus (strain ATCC 23779/DSM 785) | 4.99.1.1 | Ferrochelatase (EC 4.99.1.1) (Heme synthase) (Protoheme ferro-lyase) | CP000875; |
| A4G8D5 | HEMH_HERAR | hemH HEAR2650 | Herminiimonas arsenicoxydans | 4.99.1.1 | Ferrochelatase (EC 4.99.1.1) (Heme synthase) (Protoheme ferro-lyase) | CU207211; |
| P42045 | HEMH_HORVU | HEMH | Hordeum vulgare (Barley) | 4.99.1.1 | Ferrochelatase-2, chloroplastic (EC 4.99.1.1) (Ferrochelatase II) (Heme synthase 2) (Protoheme ferro-lyase 2) | D26105; AF02079l; |
| P22830 | HEMH_HUMAN | FECH | Homo sapiens (Human) | 4.99.1.1 | Ferrochelatase, mitochondrial (EC 4.99.1.1) (Heme synthase) (Protoheme ferro-lyase) | D00726; AJ250235; BT019958; AK292937; CH471096; BC039841; L36178; AF495859; |
| Q0BWA5 | HEMH_HYPNA | hemH HNE_3567 | Hyphomonas neptunium (strain ATCC 15444) | 4.99.1.1 | Ferrochelatase (EC 4.99.1.1) (Heme synthase) (Protoheme ferro-lyase) | CP000158; |
| Q5QVZ8 | HEMH_IDILO | hemH Il2347 | Idiomarina loihiensis | 4.99.1.1 | Ferrochelatase (EC 4.99.1.1) (Heme synthase) (Protoheme ferro-lyase) | AE017340; |
| A6T228 | HEMH_JANMA | hemH mma_2885 | Janthinobacterium sp. (strain Marseille) (Minibacterium massiliensis) | 4.99.1.1 | Ferrochelatase (EC 4.99.1.1) (Heme synthase) (Protoheme ferro-lyase) | CP000269; |
| B5Y0N2 | HEMH_KLEP3 | hemH KPK_4223 | Klebsiella pneumoniae (strain 342) | 4.99.1.1 | Ferrochelatase (EC 4.99.1.1) (Heme synthase) (Protoheme ferro-lyase) | CP000964; |
| Q036X3 | HEMH_LACC3 | hemH LSEI_1991 | Lactobacillus casei (strain ATCC 334) | 4.99.1.1 | Ferrochelatase (EC 4.99.1.1) (Heme synthase) (Protoheme ferro-lyase) | CP000423; |
| B3W963 | HEMH_LACCB | hemH LCABL_21650 | Lactobacillus casei (strain BL23) | 4.99.1.1 | Ferrochelatase (EC 4.99.1.1) (Heme synthase) (Protoheme ferro-lyase) | FM177140; |
| Q9CFB4 | HEMH_LACLA | hemH LL1567 L0194 | Lactococcus lactis subsp. lactis (Streptococcus lactis) | 4.99.1.1 | Ferrochelatase (EC 4.99.1.1) (Heme synthase) (Protoheme ferro-lyase) | AE005176; |
| A2RJS3 | HEMH_LACLM | hemH llmg_0934 | Lactococcus lactis subsp. cremoris (strain MG1363) | 4.99.1.1 | Ferrochelatase (EC 4.99.1.1) (Heme synthase) (Protoheme ferro-lyase) | AM406671; |
| Q02Y14 | HEMH_LACLS | hemH LACR_1661 | Lactococcus lactis subsp. cremoris (strain SK11) | 4.99.1.1 | Ferrochelatase (EC 4.99.1.1) (Heme synthase) (Protoheme ferro-lyase) | CP000425; |
| Q88XC3 | HEMH_LACPL | hemH lp_1296 | Lactobacillus plantarum | 4.99.1.1 | Ferrochelatase (EC 4.99.1.1) (Heme synthase) (Protoheme ferro-lyase) | AL935255; |
| A5VLS3 | HEMH_LACRD | hemH Lreu_1554 | Lactobacillus reuteri (strain DSM 20016) | 4.99.1.1 | Ferrochelatase (EC 4.99.1.1) (Heme synthase) (Protoheme ferro-lyase) | CP000705; |
| B2G944 | HEMH_LACRJ | hemH LAR_1460 | Lactobacillus reuteri (strain JCM 1112) | 4.99.1.1 | Ferrochelatase (EC 4.99.1.1) (Heme synthase) (Protoheme ferro-lyase) | AP007281; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| Q5X7W3 | HEMH_LEGPA | hemH lpp0492 | *Legionella pneumophila* (strain Paris) | 4.99.1.1 | Ferrochelatase (EC 4.99.1.1) (Heme synthase) (Protoheme ferro-lyase) | CR628336; |
| A5IHG9 | HEMH_LEGPC | hemH LPC_2918 | *Legionella pneumophila* (strain Corby) | 4.99.1.1 | Ferrochelatase (EC 4.99.1.1) (Heme synthase) (Protoheme ferro-lyase) | CP000675; |
| Q5ZYE7 | HEMH_LEGPH | hemH lpg0425 | *Legionella pneumophila* subsp. *pneumophila* (strain Philadelphia 1/ATCC 33152/DSM 7513) | 4.99.1.1 | Ferrochelatase (EC 4.99.1.1) (Heme synthase) (Protoheme ferro-lyase) | AE017354; |
| Q5WZB4 | HEMH_LEGPL | hemH lpl0468 | *Legionella pneumophila* (strain Lens) | 4.99.1.1 | Ferrochelatase (EC 4.99.1.1) (Heme synthase) (Protoheme ferro-lyase) | CR628337; |
| Q6AHF2 | HEMH_LEIXX | hemH Lxx01090 | *Leifsonia xyli* subsp. *xyli* | 4.99.1.1 | Ferrochelatase (EC 4.99.1.1) (Heme synthase) (Protoheme ferro-lyase) | AE016822; |
| B0SF60 | HEMH_LEPBA | hemH LBF_1123 | *Leptospira biflexa* serovar Patoc (strain Patoc 1/Ames) | 4.99.1.1 | Ferrochelatase (EC 4.99.1.1) (Heme synthase) (Protoheme ferro-lyase) | CP000777; |
| Q8GCV0 | HEMH_LEPBI | hemH | *Leptospira biflexa* | 4.99.1.1 | Ferrochelatase (EC 4.99.1.1) (Heme synthase) (Protoheme ferro-lyase) | AY164270; |
| Q04NU7 | HEMH_LEPBJ | hemH LBJ_4018 | *Leptospira borgpetersenii* serovar Hardjo-bovis (strain JB197) | 4.99.1.1 | Ferrochelatase (EC 4.99.1.1) (Heme synthase) (Protoheme ferro-lyase) | CP000351; |
| Q04X34 | HEMH_LEPBL | hemH LBL_4018 | *Leptospira borgpetersenii* serovar Hardjo-bovis (strain L550) | 4.99.1.1 | Ferrochelatase (EC 4.99.1.1) (Heme synthase) (Protoheme ferro-lyase) | CP000349; |
| B0SNJ9 | HEMH_LEPBP | hemH LEPBI_I1164 | *Leptospira biflexa* serovar Patoc (strain Patoc 1/ATCC 23582/Paris) | 4.99.1.1 | Ferrochelatase (EC 4.99.1.1) (Heme synthase) (Protoheme ferro-lyase) | CP000786; |
| Q03Z41 | HEMH_LEUMM | hemH LEUM_0412 | *Leuconostoc mesenteroides* subsp. *mesenteroides* (strain ATCC 8293/NCDO 523) | 4.99.1.1 | Ferrochelatase (EC 4.99.1.1) (Heme synthase) (Protoheme ferro-lyase) | CP000414; |
| Q929G2 | HEMH_LISIN | hemH lin2314 | *Listeria innocua* | 4.99.1.1 | Ferrochelatase (EC 4.99.1.1) (Heme synthase) (Protoheme ferro-lyase) | AL596171; |
| Q71XF4 | HEMH_LISMF | hemH LMOf2365_2244 | *Listeria monocytogenes* serotype 4b (strain F2365) | 4.99.1.1 | Ferrochelatase (EC 4.99.1.1) (Heme synthase) (Protoheme ferro-lyase) | AE017262; |
| Q8Y565 | HEMH_LISMO | hemH lmo2211 | *Listeria monocytogenes* | 4.99.1.1 | Ferrochelatase (EC 4.99.1.1) (Heme synthase) (Protoheme ferro-lyase) | AL591982; |
| Q65SV7 | HEMH_MANSM | hemH MS1346 | *Mannheimia succiniciproducens* (strain MBEL55E) | 4.99.1.1 | Ferrochelatase (EC 4.99.1.1) (Heme synthase) (Protoheme ferro-lyase) | AE016827; |
| A1U0R2 | HEMH_MARAV | hemH Maqu_1496 | *Marinobacter aquaeolei* (strain ATCC 700491/DSM 11845/VT8) (*Marinobacter hydrocarbonoclasticus* (strain DSM 11845)) | 4.99.1.1 | Ferrochelatase (EC 4.99.1.1) (Heme synthase) (Protoheme ferro-lyase) | CP000514; |
| A6VXF8 | HEMH_MARMS | hemH Mmwyl1_2215 | *Marinomonas* sp. (strain MWYL1) | 4.99.1.1 | Ferrochelatase (EC 4.99.1.1) (Heme synthase) (Protoheme ferro-lyase) | CP000749; |
| Q11ES4 | HEMH_MESSB | hemH Meso_2724 | *Mesorhizobium* sp. (strain BNC1) | 4.99.1.1 | Ferrochelatase (EC 4.99.1.1) (Heme synthase) (Protoheme ferro-lyase) | CP000390; |
| Q607T4 | HEMH_METCA | hemH MCA1671 | *Methylococcus capsulatus* | 4.99.1.1 | Ferrochelatase (EC 4.99.1.1) (Heme synthase) (Protoheme ferro-lyase) | AE017282; |
| Q1H397 | HEMH_METFK | hemH Mfla_0772 | *Methylobacillus flagellatus* (strain KT/ATCC 51484/DSM 6875) | 4.99.1.1 | Ferrochelatase (EC 4.99.1.1) (Heme synthase) (Protoheme ferro-lyase) | CP000284; |
| A2SIR1 | HEMH_METPP | hemH Mpe_A2495 | *Methylibium petroleiphilum* (strain PM1) | 4.99.1.1 | Ferrochelatase (EC 4.99.1.1) (Heme synthase) (Protoheme ferro-lyase) | CP000555; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| B8EJ84 | HEMH_METSB | hemH Msil_3692 | Methylocella silvestris (strain BL2/DSM 15510/NCIMB 13906) | 4.99.1.1 | Ferrochelatase (EC 4.99.1.1) (Heme synthase) (Protoheme ferro-lyase) | CP001280; |
| B0JRN7 | HEMH_MICAN | hemH MAE_09650 | Microcystis aeruginosa (strain NIES-843) | 4.99.1.1 | Ferrochelatase (EC 4.99.1.1) (Heme synthase) (Protoheme ferro-lyase) | AP009552; |
| P22315 | HEMH_MOUSE | Fech | Mus musculus (Mouse) | 4.99.1.1 | Ferrochelatase, mitochondrial (EC 4.99.1.1) (Heme synthase) (Protoheme ferro-lyase) | M61215; M59288; |
| A0QHT7 | HEMH_MYCA1 | hemH MAV_3293 | Mycobacterium avium (strain 104) | 4.99.1.1 | Ferrochelatase (EC 4.99.1.1) (Heme synthase) (Protoheme ferro-lyase) | CP000479; |
| B1MC29 | HEMH_MYCA9 | hemH MAB_2721c | Mycobacterium abscessus (strain ATCC 19977/DSM 44196) | 4.99.1.1 | Ferrochelatase (EC 4.99.1.1) (Heme synthase) (Protoheme ferro-lyase) | CU458896; |
| O07401 | HEMH_MYCAV | hemH | Mycobacterium avium | 4.99.1.1 | Ferrochelatase (EC 4.99.1.1) (Heme synthase) (Protoheme ferro-lyase) | AF002133; |
| P0A577 | HEMH_MYCBO | hemH hemZ Mb1521 | Mycobacterium bovis | 4.99.1.1 | Ferrochelatase (EC 4.99.1.1) (Heme synthase) (Protoheme ferro-lyase) | BX248339; |
| A1KIS5 | HEMH_MYCBP | hemH BCG_1547 | Mycobacterium bovis (strain BCG/Pasteur 1173P2) | 4.99.1.1 | Ferrochelatase (EC 4.99.1.1) (Heme synthase) (Protoheme ferro-lyase) | AM408590; |
| C1AND1 | HEMH_MYCBT | hemH JTY_1522 | Mycobacterium bovis (strain BCG/Tokyo 172/ATCC 35737/TMC 1019) | 4.99.1.1 | Ferrochelatase (EC 4.99.1.1) (Heme synthase) (Protoheme ferro-lyase) | AP010918; |
| A4T9I1 | HEMH_MYCGI | hemH Mflv_3656 | Mycobacterium gilvum (strain PYR-GCK) (Mycobacterium flavescens (strain ATCC 700033/PYR-GCK)) | 4.99.1.1 | Ferrochelatase (EC 4.99.1.1) (Heme synthase) (Protoheme ferro-lyase) | CP000656; |
| B8ZS79 | HEMH_MYCLB | hemH MLBr01805 | Mycobacterium leprae (strain Br4923) | 4.99.1.1 | Ferrochelatase (EC 4.99.1.1) (Heme synthase) (Protoheme ferro-lyase) | FM211192; |
| Q9CBM2 | HEMH_MYCLE | hemH hemZ ML1805 | Mycobacterium leprae | 4.99.1.1 | Ferrochelatase (EC 4.99.1.1) (Heme synthase) (Protoheme ferro-lyase) | AL583923; |
| B2HPD6 | HEMH_MYCMM | hemH MMAR_2291 | Mycobacterium marinum (strain ATCC BAA-535/M) | 4.99.1.1 | Ferrochelatase (EC 4.99.1.1) (Heme synthase) (Protoheme ferro-lyase) | CP000854; |
| Q740Y1 | HEMH_MYCPA | hemH MAP_1211 | Mycobacterium paratuberculosis | 4.99.1.1 | Ferrochelatase (EC 4.99.1.1) (Heme synthase) (Protoheme ferro-lyase) | AE016958; |
| A0QX29 | HEMH_MYCS2 | hemH MSMEG_3152 | Mycobacterium smegmatis (strain ATCC 700084/mc(2)155) | 4.99.1.1 | Ferrochelatase (EC 4.99.1.1) (Heme synthase) (Protoheme ferro-lyase) | CP000480; |
| A3PZF2 | HEMH_MYCSJ | hemH Mjls_2495 | Mycobacterium sp. (strain JLS) | 4.99.1.1 | Ferrochelatase (EC 4.99.1.1) (Heme synthase) (Protoheme ferro-lyase) | CP000580; |
| A1UFU2 | HEMH_MYCSK | hemH Mkms_2503 | Mycobacterium sp. (strain KMS) | 4.99.1.1 | Ferrochelatase (EC 4.99.1.1) (Heme synthase) (Protoheme ferro-lyase) | CP000518; |
| Q1B968 | HEMH_MYCSS | hemH Mmcs_2458 | Mycobacterium sp. (strain MCS) | 4.99.1.1 | Ferrochelatase (EC 4.99.1.1) (Heme synthase) (Protoheme ferro-lyase) | CP000384; |
| A5U219 | HEMH_MYCTA | hemH MRA_1495 | Mycobacterium tuberculosis (strain ATCC 25177/H37Ra) | 4.99.1.1 | Ferrochelatase (EC 4.99.1.1) (Heme synthase) (Protoheme ferro-lyase) | CP000611; |
| P0A576 | HEMH_MYCTU | hemH hemZ Rv1485 MT1532 MTCY277.06 | Mycobacterium tuberculosis | 4.99.1.1 | Ferrochelatase (EC 4.99.1.1) (Heme synthase) (Protoheme ferro-lyase) | BX842576; AE000516; |
| A0PNU6 | HEMH_MYCUA | hemH MUL_1493 | Mycobacterium ulcerans (strain Agy99) | 4.99.1.1 | Ferrochelatase (EC 4.99.1.1) (Heme synthase) (Protoheme ferro-lyase) | CP000325; |
| A1T8R1 | HEMH_MYCVP | hemH Mvan_2754 | Mycobacterium vanbaalenii (strain DSM 7251/PYR-1) | 4.99.1.1 | Ferrochelatase (EC 4.99.1.1) (Heme synthase) (Protoheme ferro-lyase) | CP000511; |
| Q5F9U6 | HEMH_NEIG1 | hemH NGO0293 | Neisseria gonorrhoeae (strain ATCC 700825/FA 1090) | 4.99.1.1 | Ferrochelatase (EC 4.99.1.1) (Heme synthase) (Protoheme ferro-lyase) | AE004969; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| Q9JVA5 | HEMH_NEIMA | hemH NMA0927 | *Neisseria meningitidis* serogroup A | 4.99.1.1 | Ferrochelatase (EC 4.99.1.1) (Heme synthase) (Protoheme ferro-lyase) | AL157959; |
| Q9K097 | HEMH_NEIMB | hemH NMB0718 | *Neisseria meningitidis* serogroup B | 4.99.1.1 | Ferrochelatase (EC 4.99.1.1) (Heme synthase) (Protoheme ferro-lyase) | AE002098; |
| A1KSY0 | HEMH_NEIMF | hemH NMC0669 | *Neisseria meningitidis* serogroup C/serotype 2a (strain ATCC 700532/FAM18) | 4.99.1.1 | Ferrochelatase (EC 4.99.1.1) (Heme synthase) (Protoheme ferro-lyase) | AM421808; |
| Q82UK8 | HEMH_NITEU | hemH NE1476 | *Nitrosomonas europaea* | 4.99.1.1 | Ferrochelatase (EC 4.99.1.1) (Heme synthase) (Protoheme ferro-lyase) | AL954747; |
| Q1QI02 | HEMH_NITHX | hemH Nham_3415 | *Nitrobacter hamburgensis* (strain X14/DSM 10229) | 4.99.1.1 | Ferrochelatase (EC 4.99.1.1) (Heme synthase) (Protoheme ferro-lyase) | CP000319; |
| Q3JAW7 | HEMH_NITOC | hemH Noc_1545 | *Nitrosococcus oceani* (strain ATCC 19707/NCIMB 11848) | 4.99.1.1 | Ferrochelatase (EC 4.99.1.1) (Heme synthase) (Protoheme ferro-lyase) | CP000127; |
| A6Q2Y9 | HEMH_NITSB | hemH NIS_0734 | *Nitratiruptor* sp. (strain SB155-2) | 4.99.1.1 | Ferrochelatase (EC 4.99.1.1) (Heme synthase) (Protoheme ferro-lyase) | AP009178; |
| Q5YU18 | HEMH_NOCFA | hemH NFA_34750 | *Nocardia farcinica* | 4.99.1.1 | Ferrochelatase (EC 4.99.1.1) (Heme synthase) (Protoheme ferro-lyase) | AP006618; |
| B2J9P0 | HEMH_NOSP7 | hemH Npun_F2510 | *Nostoc punctiforme* (strain ATCC 29133/PCC 73102) | 4.99.1.1 | Ferrochelatase (EC 4.99.1.1) (Heme synthase) (Protoheme ferro-lyase) | CP001037; |
| Q8YQR8 | HEMH_NOSS1 | hemH alr3751 | *Nostoc* sp. (strain PCC 7120/UTEX 2576) | 4.99.1.1 | Ferrochelatase (EC 4.99.1.1) (Heme synthase) (Protoheme ferro-lyase) | BA000019; |
| Q8ERX9 | HEMH_OCEIH | hemH OB1168 | *Oceanobacillus iheyensis* | 4.99.1.1 | Ferrochelatase (EC 4.99.1.1) (Heme synthase) (Protoheme ferro-lyase) | BA000028; |
| A6X6W2 | HEMH_OCHA4 | hemH Oant_4266 | *Ochrobactrum anthropi* (strain ATCC 49188/DSM 6882/NCTC 12168) | 4.99.1.1 | Ferrochelatase (EC 4.99.1.1) (Heme synthase) (Protoheme ferro-lyase) | CP000759; |
| B1ZSW3 | HEMH_OPITP | hemH Oter_2470 | *Opitutus terrae* (strain DSM 11246/PB90-1) | 4.99.1.1 | Ferrochelatase (EC 4.99.1.1) (Heme synthase) (Protoheme ferro-lyase) | CP001032; |
| A2Y3Q5 | HEMH_ORYSI | HEMH Osi_018948 | *Oryza sativa* subsp. *indica* (Rice) | 4.99.1.1 | Ferrochelatase-2, chloroplastic (EC 4.99.1.1) (Ferrochelatase II) (Heme synthase 2) (Protoheme ferro-lyase 2) | AB007120; |
| Q3YA36 | HEMH_PANTR | FECH | *Pan troglodytes* (Chimpanzee) | 4.99.1.1 | Ferrochelatase, mitochondrial (EC 4.99.1.1) (Heme synthase) (Protoheme ferro-lyase) | DQ149645; |
| Q6MAW8 | HEMH_PARUW | hemH pc1557 | *Protochlamydia amoebophila* (strain UWE25) | 4.99.1.1 | Ferrochelatase (EC 4.99.1.1) (Heme synthase) (Protoheme ferro-lyase) | BX908798; |
| P57874 | HEMH_PASMU | hemH PM0789 | *Pasteurella multocida* | 4.99.1.1 | Ferrochelatase (EC 4.99.1.1) (Heme synthase) (Protoheme ferro-lyase) | AE004439; |
| A1ASJ7 | HEMH_PELPD | hemH Ppro_2715 | *Pelobacter propionicus* (strain DSM 2379) | 4.99.1.1 | Ferrochelatase (EC 4.99.1.1) (Heme synthase) (Protoheme ferro-lyase) | CP000482; |
| Q4FNS1 | HEMH_PELUB | hemH SAR11_0346 | *Pelagibacter ubique* | 4.99.1.1 | Ferrochelatase (EC 4.99.1.1) (Heme synthase) (Protoheme ferro-lyase) | CP000084; |
| B4RD10 | HEMH_PHEZH | hemH PHZ_c3533 | *Phenylobacterium zucineum* (strain HLK1) | 4.99.1.1 | Ferrochelatase (EC 4.99.1.1) (Heme synthase) (Protoheme ferro-lyase) | CP000747; |
| Q7N0P6 | HEMH_PHOLL | hemH plu3835 | *Photorhabdus luminescens* subsp. *laumondii* | 4.99.1.1 | Ferrochelatase (EC 4.99.1.1) (Heme synthase) (Protoheme ferro-lyase) | BX571871; |
| Q6LTE0 | HEMH_PHOPR | hemH PBPRA1025 | *Photobacterium profundum* (*Photobacterium* sp. (strain SS9)) | 4.99.1.1 | Ferrochelatase (EC 4.99.1.1) (Heme synthase) (Protoheme ferro-lyase) | CR378666; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| Q12BZ9 | HEMH_POLSJ | hemH Bpro_2013 | *Polaromonas* sp. (strain JS666/ATCC BAA-500) | 4.99.1.1 | Ferrochelatase (EC 4.99.1.1) (Heme synthase) (Protoheme ferro-lyase) | CP000316; |
| B2RHB4 | HEMH_PORG3 | hemH PGN_0240 | *Porphyromonas gingivalis* (strain ATCC 33277/DSM 20709/JCM 12257) | 4.99.1.1 | Ferrochelatase (EC 4.99.1.1) (Heme synthase) (Protoheme ferro-lyase) | AP009380; |
| Q7MXP4 | HEMH_PORGI | hemH PG_0127 | *Porphyromonas gingivalis* (*Bacteroides gingivalis*) | 4.99.1.1 | Ferrochelatase (EC 4.99.1.1) (Heme synthase) (Protoheme ferro-lyase) | AE015924; |
| P72183 | HEMH_PROFF | hemH | *Propionibacterium freudenreichii* subsp. *freudenreichii* | 4.99.1.1 | Ferrochelatase (EC 4.99.1.1) (Heme synthase) (Protoheme ferro-lyase) | D85417; U51164; |
| A3PBP9 | HEMH_PROM0 | hemH P9301_05511 | *Prochlorococcus marinus* (strain MIT 9301) | 4.99.1.1 | Ferrochelatase (EC 4.99.1.1) (Heme synthase) (Protoheme ferro-lyase) | CP000576; |
| A2C0Y4 | HEMH_PROM1 | hemH NATL1_05821 | *Prochlorococcus marinus* (strain NATL1A) | 4.99.1.1 | Ferrochelatase (EC 4.99.1.1) (Heme synthase) (Protoheme ferro-lyase) | CP000553; |
| A8G3P0 | HEMH_PROM2 | hemH P9215_06061 | *Prochlorococcus marinus* (strain MIT 9215) | 4.99.1.1 | Ferrochelatase (EC 4.99.1.1) (Heme synthase) (Protoheme ferro-lyase) | CP000825; |
| A2C7Q7 | HEMH_PROM3 | hemH P9303_07661 | *Prochlorococcus marinus* (strain MIT 9303) | 4.99.1.1 | Ferrochelatase (EC 4.99.1.1) (Heme synthase) (Protoheme ferro-lyase) | CP000554; |
| A9BEE9 | HEMH_PROM4 | hemH P9211_05281 | *Prochlorococcus marinus* (strain MIT 9211) | 4.99.1.1 | Ferrochelatase (EC 4.99.1.1) (Heme synthase) (Protoheme ferro-lyase) | CP000878; |
| A2BVI7 | HEMH_PROM5 | hemH P9515_05891 | *Prochlorococcus marinus* (strain MIT 9515) | 4.99.1.1 | Ferrochelatase (EC 4.99.1.1) (Heme synthase) (Protoheme ferro-lyase) | CP000552; |
| Q31C09 | HEMH_PROM9 | hemH PMT9312_0525 | *Prochlorococcus marinus* (strain MIT 9312) | 4.99.1.1 | Ferrochelatase (EC 4.99.1.1) (Heme synthase) (Protoheme ferro-lyase) | CP000111; |
| Q7VD58 | HEMH_PROMA | hemH Pro_0525 | *Prochlorococcus marinus* | 4.99.1.1 | Ferrochelatase (EC 4.99.1.1) (Heme synthase) (Protoheme ferro-lyase) | AE017126; |
| B4F1Q1 | HEMH_PROMH | hemH PMI2183 | *Proteus mirabilis* (strain HI4320) | 4.99.1.1 | Ferrochelatase (EC 4.99.1.1) (Heme synthase) (Protoheme ferro-lyase) | AM942759; |
| Q7V6C6 | HEMH_PROMM | hemH PMT_1240 | *Prochlorococcus marinus* (strain MIT 9313) | 4.99.1.1 | Ferrochelatase (EC 4.99.1.1) (Heme synthase) (Protoheme ferro-lyase) | BX548175; |
| Q7V2F5 | HEMH_PROMP | hemH PMM0525 | *Prochlorococcus marinus* subsp. *pastoris* (strain CCMP1986/MED4) | 4.99.1.1 | Ferrochelatase (EC 4.99.1.1) (Heme synthase) (Protoheme ferro-lyase) | BX548174; |
| A2BQ06 | HEMH_PROMS | hemH A9601_05811 | *Prochlorococcus marinus* (strain AS9601) | 4.99.1.1 | Ferrochelatase (EC 4.99.1.1) (Heme synthase) (Protoheme ferro-lyase) | CP000551; |
| Q46GQ1 | HEMH_PROMT | hemH PMN2A_1857 | *Prochlorococcus marinus* (strain NATL2A) | 4.99.1.1 | Ferrochelatase (EC 4.99.1.1) (Heme synthase) (Protoheme ferro-lyase) | CP000095; |
| Q48MT5 | HEMH_PSE14 | hemH PSPPH_1016 | *Pseudomonas syringae* pv. *phaseolicola* (strain 1448A/Race 6) | 4.99.1.1 | Ferrochelatase (EC 4.99.1.1) (Heme synthase) (Protoheme ferro-lyase) | CP000058; |
| Q15NQ1 | HEMH_PSEA6 | hemH Patl_3987 | *Pseudoalteromonas atlantica* (strain T6c/BAA-1087) | 4.99.1.1 | Ferrochelatase (EC 4.99.1.1) (Heme synthase) (Protoheme ferro-lyase) | CP000388; |
| A6VC51 | HEMH_PSEA7 | hemH PSPA7_5304 | *Pseudomonas aeruginosa* (strain PA7) | 4.99.1.1 | Ferrochelatase (EC 4.99.1.1) (Heme synthase) (Protoheme ferro-lyase) | CP000744; |
| B7V0K1 | HEMH_PSEA8 | hemH PLES_50411 | *Pseudomonas aeruginosa* (strain LESB58) | 4.99.1.1 | Ferrochelatase (EC 4.99.1.1) (Heme synthase) (Protoheme ferro-lyase) | FM209186; |
| Q02G19 | HEMH_PSEAB | hemH PA14_61580 | *Pseudomonas aeruginosa* (strain UCBPP-PA14) | 4.99.1.1 | Ferrochelatase (EC 4.99.1.1) (Heme synthase) (Protoheme ferro-lyase) | CP000438; |
| Q9HVD7 | HEMH_PSEAE | hemH PA4655 | *Pseudomonas aeruginosa* | 4.99.1.1 | Ferrochelatase (EC 4.99.1.1) (Heme synthase) (Protoheme ferro-lyase) | AE004091; |

TABLE 3-continued

Characterized Ferrochelatase Enzymes

| UniProtKB/ SwissProt Accession No. | Entry Name | Gene Names | Organism | EC Number | Protein Names | EMBL Accession No. |
|---|---|---|---|---|---|---|
| Q1IEW1 | HEMH_PSEE4 | hemH PSEEN0886 | *Pseudomonas entomophila* (strain L48) | 4.99.1.1 | Ferrochelatase (EC 4.99.1.1) (Heme synthase) (Protoheme ferro-lyase) | CT573326; |
| Q4K6B3 | HEMH_PSEF5 | hemH PFL_5141 | *Pseudomonas fluorescens* (strain Pf-5/ATCC BAA-477) | 4.99.1.1 | Ferrochelatase (EC 4.99.1.1) (Heme synthase) (Protoheme ferro-lyase) | CP000076; |
| P57778 | HEMH_PSEFC | hemH | *Pseudomonas fluorescens* biotype C | 4.99.1.1 | Ferrochelatase (EC 4.99.1.1) (Heme synthase) (Protoheme ferro-lyase) | AF314196; |
| C3KDN7 | HEMH_PSEFS | hemH PFLU_0756 | *Pseudomonas fluorescens* (strain SBW25) | 4.99.1.1 | Ferrochelatase (EC 4.99.1.1) (Heme synthase) (Protoheme ferro-lyase) | AM181176; |
| A4XR78 | HEMH_PSEMY | hemH Pmen_1077 | *Pseudomonas mendocina* (strain ymp) | 4.99.1.1 | Ferrochelatase (EC 4.99.1.1) (Heme synthase) (Protoheme ferro-lyase) | CP000680; |
| A5VYH6 | HEMH_PSEP1 | hemH Pput_0772 | *Pseudomonas putida* (strain F1/ATCC 700007) | 4.99.1.1 | Ferrochelatase (EC 4.99.1.1) (Heme synthase) (Protoheme ferro-lyase) | CP000712; |
| Q3K6Y7 | HEMH_PSEPF | hemH Pfl01_4730 | *Pseudomonas fluorescens* (strain Pf0-1) | 4.99.1.1 | Ferrochelatase (EC 4.99.1.1) (Heme synthase) (Protoheme ferro-lyase) | CP000094; |
| B0KNF5 | HEMH_PSEPG | hemH PputGB1_0785 | *Pseudomonas putida* (strain GB-1) | 4.99.1.1 | Ferrochelatase (EC 4.99.1.1) (Heme synthase) (Protoheme ferro-lyase) | CP000926; |
| Q88PV4 | HEMH_PSEPK | hemH PP_0744 | *Pseudomonas putida* (strain KT2440) | 4.99.1.1 | Ferrochelatase (EC 4.99.1.1) (Heme synthase) (Protoheme ferro-lyase) | AE015451; |
| B1JER5 | HEMH_PSEPW | hemH PputW619_4445 | *Pseudomonas putida* (strain W619) | 4.99.1.1 | Ferrochelatase (EC 4.99.1.1) (Heme synthase) (Protoheme ferro-lyase) | CP000949; |
| Q88A2 | HEMH_PSESM | hemH PSPTO_1128 | *Pseudomonas syringae* pv. tomato | 4.99.1.1 | Ferrochelatase (EC 4.99.1.1) (Heme synthase) (Protoheme ferro-lyase) | AE016853; |
| Q4ZXU9 | HEMH_PSEU2 | hemH Psyr_0967 | *Pseudomonas syringae* pv. *syringae* (strain B728a) | 4.99.1.1 | Ferrochelatase (EC 4.99.1.1) (Heme synthase) (Protoheme ferro-lyase) | CP000075; |
| A4VKZ1 | HEMH_PSEU5 | hemH PST_1968 | *Pseudomonas stutzeri* (strain A1501) | 4.99.1.1 | Ferrochelatase (EC 4.99.1.1) (Heme synthase) (Protoheme ferro-lyase) | CP000304; |
| Q4FUR3 | HEMH_PSYA2 | hemH Psyc_0376 | *Psychrobacter arcticus* (strain DSM 17307/273-4) | 4.99.1.1 | Ferrochelatase (EC 4.99.1.1) (Heme synthase) (Protoheme ferro-lyase) | CP000082; |
| Q1QDQ5 | HEMH_PSYCK | hemH Pcryo_0415 | *Psychrobacter cryohalolentis* (strain K5) | 4.99.1.1 | Ferrochelatase (EC 4.99.1.1) (Heme synthase) (Protoheme ferro-lyase) | CP000323; |
| A5WH56 | HEMH_PSYWF | hemH PsycPRwf_2057 | *Psychrobacter* sp. (strain PRwf-1) | 4.99.1.1 | Ferrochelatase (EC 4.99.1.1) (Heme synthase) (Protoheme ferro-lyase) | CP000713; |
| Q1LPN9 | HEMH_RALME | hemH Rmet_1001 | *Ralstonia metallidurans* (strain CH34/ATCC 43123/DSM 2839) | 4.99.1.1 | Ferrochelatase (EC 4.99.1.1) (Heme synthase) (Protoheme ferro-lyase) | CP000352; |
| B2UBQ0 | HEMH_RALPJ | hemH Rpic_2877 | *Ralstonia pickettii* (strain 12J) | 4.99.1.1 | Ferrochelatase (EC 4.99.1.1) (Heme synthase) (Protoheme ferro-lyase) | CP001068; |
| Q8XW32 | HEMH_RALSO | hemH RSc2643 RS04573 | *Ralstonia solanacearum* (*Pseudomonas solanacearum*) | 4.99.1.1 | Ferrochelatase (EC 4.99.1.1) (Heme synthase) (Protoheme ferro-lyase) | AL646052; |
| B3PZU8 | HEMH_RHIE6 | hemH RHECIAT_CH0003810 | *Rhizobium etli* (strain CIAT 652) | 4.99.1.1 | Ferrochelatase (EC 4.99.1.1) (Heme synthase) (Protoheme ferro-lyase) | CP001074; |
| Q2K4C4 | HEMH_RHIEC | hemH RHE_CH03556 | *Rhizobium etli* (strain CFN 42/ATCC 51251) | 4.99.1.1 | Ferrochelatase (EC 4.99.1.1) (Heme synthase) (Protoheme ferro-lyase) | CP000133; |
| Q1MBW8 | HEMH_RHIL3 | hemH RL4076 | *Rhizobium leguminosarum* bv. *viciae* (strain 3841) | 4.99.1.1 | Ferrochelatase (EC 4.99.1.1) (Heme synthase) (Protoheme ferro-lyase) | AM236080; |
| Q98H61 | HEMH_RHILO | hemH mll3019 | *Rhizobium loti* (*Mesorhizobium loti*) | 4.99.1.1 | Ferrochelatase (EC 4.99.1.1) (Heme synthase) (Protoheme ferro-lyase) | BA000012; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| B5ZPG3 | HEMH_RHILW | hemH Rleg2_3304 | *Rhizobium leguminosarum* bv. trifolii (strain WSM2304) | 4.99.1.1 | Ferrochelatase (EC 4.99.1.1) (Heme synthase) (Protoheme ferro-lyase) | CP001191; |
| Q92M52 | HEMH_RHIME | hemH R02803 SMc04019 | *Rhizobium meliloti* (*Sinorhizobium meliloti*) | 4.99.1.1 | Ferrochelatase (EC 4.99.1.1) (Heme synthase) (Protoheme ferro-lyase) | AL591688; AF461430; |
| Q7UFZ7 | HEMH_RHOBA | hemH RB8233 | *Rhodopirellula baltica* | 4.99.1.1 | Ferrochelatase (EC 4.99.1.1) (Heme synthase) (Protoheme ferro-lyase) | BX294147; |
| Q59735 | HEMH_RHOCA | hemH | *Rhodobacter capsulatus* (*Rhodopseudomonas capsulata*) | 4.99.1.1 | Ferrochelatase (EC 4.99.1.1) (Heme synthase) (Protoheme ferro-lyase) | U34391; |
| Q2IRD5 | HEMH_RHOP2 | hemH RPB_4542 | *Rhodopseudomonas palustris* (strain HaA2) | 4.99.1.1 | Ferrochelatase (EC 4.99.1.1) (Heme synthase) (Protoheme ferro-lyase) | CP000250; |
| Q07H58 | HEMH_RHOP5 | hemH RPE_4807 | *Rhodopseudomonas palustris* (strain BisA53) | 4.99.1.1 | Ferrochelatase (EC 4.99.1.1) (Heme synthase) (Protoheme ferro-lyase) | CP000463; |
| Q6NBF3 | HEMH_RHOPA | hemH RPA0875 | *Rhodopseudomonas palustris* | 4.99.1.1 | Ferrochelatase (EC 4.99.1.1) (Heme synthase) (Protoheme ferro-lyase) | BX572595; |
| Q13CU0 | HEMH_RHOPS | hemH RPD_0861 | *Rhodopseudomonas palustris* (strain BisB5) | 4.99.1.1 | Ferrochelatase (EC 4.99.1.1) (Heme synthase) (Protoheme ferro-lyase) | CP000283; |
| B3QF66 | HEMH_RHOPT | hemH Rpal_0943 | *Rhodopseudomonas palustris* (strain TIE-1) | 4.99.1.1 | Ferrochelatase (EC 4.99.1.1) (Heme synthase) (Protoheme ferro-lyase) | CP001096; |
| A8GYD7 | HEMH_RICB8 | hemH A1I_07945 | *Rickettsia bellii* (strain OSU 85-389) | 4.99.1.1 | Ferrochelatase (EC 4.99.1.1) (Heme synthase) (Protoheme ferro-lyase) | CP000849; |
| Q1RGK5 | HEMH_RICBR | hemH RBE_1428 | *Rickettsia bellii* (strain RML369-C) | 4.99.1.1 | Ferrochelatase (EC 4.99.1.1) (Heme synthase) (Protoheme ferro-lyase) | CP000087; |
| A8F0B2 | HEMH_RICCK | hemH A1E_05670 | *Rickettsia canadensis* (strain McKiel) | 4.99.1.1 | Ferrochelatase (EC 4.99.1.1) (Heme synthase) (Protoheme ferro-lyase) | CP000409; |
| Q92FV4 | HEMH_RICCN | hemH RC1373 | *Rickettsia conorii* | 4.99.1.1 | Ferrochelatase (EC 4.99.1.1) (Heme synthase) (Protoheme ferro-lyase) | AE006914; |
| Q4UJN9 | HEMH_RICFE | hemH RF_1399 | *Rickettsia felis* (*Rickettsia azadi*) | 4.99.1.1 | Ferrochelatase (EC 4.99.1.1) (Heme synthase) (Protoheme ferro-lyase) | CP000053; |
| Q9ZC84 | HEMH_RICPR | hemH RP884 | *Rickettsia prowazekii* | 4.99.1.1 | Ferrochelatase (EC 4.99.1.1) (Heme synthase) (Protoheme ferro-lyase) | AJ235273; |
| Q68VM9 | HEMH_RICTY | hemH RT0876 | *Rickettsia typhi* | 4.99.1.1 | Ferrochelatase (EC 4.99.1.1) (Heme synthase) (Protoheme ferro-lyase) | AE017197; |
| B5EXN2 | HEMH_SALA4 | hemH SeAg_B0535 | *Salmonella agona* (strain SL483) | 4.99.1.1 | Ferrochelatase (EC 4.99.1.1) (Heme synthase) (Protoheme ferro-lyase) | CP001138; |
| A9MLY4 | HEMH_SALAR | hemH SARI_02445 | *Salmonella arizonae* (strain ATCC BAA-731/CDC346-86/RSK2980) | 4.99.1.1 | Ferrochelatase (EC 4.99.1.1) (Heme synthase) (Protoheme ferro-lyase) | CP000880; |
| Q57S74 | HEMH_SALCH | hemH SCH_0531 | *Salmonella choleraesuis* | 4.99.1.1 | Ferrochelatase (EC 4.99.1.1) (Heme synthase) (Protoheme ferro-lyase) | AE017220; |
| B5FLJ9 | HEMH_SALDC | hemH SeD_A0536 | *Salmonella dublin* (strain CT_02021853) | 4.99.1.1 | Ferrochelatase (EC 4.99.1.1) (Heme synthase) (Protoheme ferro-lyase) | CP001144; |
| B5QU78 | HEMH_SALEP | hemH SEN0470 | *Salmonella enteritidis* PT4 (strain P125109) | 4.99.1.1 | Ferrochelatase (EC 4.99.1.1) (Heme synthase) (Protoheme ferro-lyase) | AM933172; |
| B5R613 | HEMH_SALG2 | hemH SG0500 | *Salmonella gallinarum* (strain 287/91/NCTC 13346) | 4.99.1.1 | Ferrochelatase (EC 4.99.1.1) (Heme synthase) (Protoheme ferro-lyase) | AM933173; |
| B4T9I3 | HEMH_SALHS | hemH SeHA_C0595 | *Salmonella heidelberg* (strain SL476) | 4.99.1.1 | Ferrochelatase (EC 4.99.1.1) (Heme synthase) (Protoheme ferro-lyase) | CP001120; |

TABLE 3-continued

Characterized Ferrochelatase Enzymes

| UniProtKB/SwissProt Accession No. | Entry Name | Gene Names | EC Number | Protein Names | EMBL Accession No. |
|---|---|---|---|---|---|
| B4SWY3 | HEMH_SALNS | hemH SNSL254_A0541 | 4.99.1.1 | Ferrochelatase (EC 4.99.1.1) (Heme synthase) (Protoheme ferro-lyase) | CP001113; |
| Q5PFJ1 | HEMH_SALPA | hemH SPA2233 | 4.99.1.1 | Ferrochelatase (EC 4.99.1.1) (Heme synthase) (Protoheme ferro-lyase) | CP000026; |
| A9MW82 | HEMH_SALPB | hemH SPAB_03079 | 4.99.1.1 | Ferrochelatase (EC 4.99.1.1) (Heme synthase) (Protoheme ferro-lyase) | CP000886; |
| C0PVE1 | HEMH_SALPC | hemH SPC_0504 | 4.99.1.1 | Ferrochelatase (EC 4.99.1.1) (Heme synthase) (Protoheme ferro-lyase) | CP000857; |
| B5BD43 | HEMH_SALPK | hemH SSPA2076 | 4.99.1.1 | Ferrochelatase (EC 4.99.1.1) (Heme synthase) (Protoheme ferro-lyase) | FM200053; |
| B4TMG7 | HEMH_SALSV | hemH SeSA_A0551 | 4.99.1.1 | Ferrochelatase (EC 4.99.1.1) (Heme synthase) (Protoheme ferro-lyase) | CP001127; |
| Q8Z8T2 | HEMH_SALTI | hemH STY0533 t2371 | 4.99.1.1 | Ferrochelatase (EC 4.99.1.1) (Heme synthase) (Protoheme ferro-lyase) | AL627267; AE014613; |
| P37408 | HEMH_SALTY | hemH visA STM0489 | 4.99.1.1 | Ferrochelatase (EC 4.99.1.1) (Heme synthase) (Protoheme ferro-lyase) | AE006468; L26246; |
| O59786 | HEMH_SCHPO | SPCC320.09 | 4.99.1.1 | Ferrochelatase, mitochondrial (EC 4.99.1.1) (Heme synthase) (Protoheme ferro-lyase) | CU329672; |
| A8GAV7 | HEMH_SERP5 | hemH Spro_1143 | 4.99.1.1 | Ferrochelatase (EC 4.99.1.1) (Heme synthase) (Protoheme ferro-lyase) | CP000826; |
| Q12KR9 | HEMH_SHEDO | hemH Sden_2678 | 4.99.1.1 | Ferrochelatase (EC 4.99.1.1) (Heme synthase) (Protoheme ferro-lyase) | CP000302; |
| B2U4S8 | HEMH_SHIB3 | hemH SbBS512_E0408 | 4.99.1.1 | Ferrochelatase (EC 4.99.1.1) (Heme synthase) (Protoheme ferro-lyase) | CP001063; |
| Q32C1 | HEMH_SHIBS | hemH SBO_0375 | 4.99.1.1 | Ferrochelatase (EC 4.99.1.1) (Heme synthase) (Protoheme ferro-lyase) | CP000036; |
| Q32I55 | HEMH_SHIDS | hemH SDY_0444 | 4.99.1.1 | Ferrochelatase (EC 4.99.1.1) (Heme synthase) (Protoheme ferro-lyase) | CP000034; |
| Q0T7B0 | HEMH_SHIF8 | hemH SFV_0448 | 4.99.1.1 | Ferrochelatase (EC 4.99.1.1) (Heme synthase) (Protoheme ferro-lyase) | CP000266; |
| Q83SE5 | HEMH_SHIFL | hemH SF0420 S0427 | 4.99.1.1 | Ferrochelatase (EC 4.99.1.1) (Heme synthase) (Protoheme ferro-lyase) | AE005674; AE014073; |
| Q3Z4S4 | HEMH_SHISS | hemH SSON_0462 | 4.99.1.1 | Ferrochelatase (EC 4.99.1.1) (Heme synthase) (Protoheme ferro-lyase) | CP000038; |
| Q2NV56 | HEMH_SODGM | hemH SG0694 | 4.99.1.1 | Ferrochelatase (EC 4.99.1.1) (Heme synthase) (Protoheme ferro-lyase) | AP008232; |
| Q5HEU3 | HEMH_STAAC | hemH SACOL1888 | 4.99.1.1 | Ferrochelatase (EC 4.99.1.1) (Heme synthase) (Protoheme ferro-lyase) | CP000046; |
| P64124 | HEMH_STAAM | hemH SAV1833 | 4.99.1.1 | Ferrochelatase (EC 4.99.1.1) (Heme synthase) (Protoheme ferro-lyase) | BA000017; |
| P64125 | HEMH_STAAN | hemH SA1651 | 4.99.1.1 | Ferrochelatase (EC 4.99.1.1) (Heme synthase) (Protoheme ferro-lyase) | BA000018; |
| Q6GFM4 | HEMH_STAAR | hemF hemH SAR1924 | 4.99.1.1 | Ferrochelatase (EC 4.99.1.1) (Heme synthase) (Protoheme ferro-lyase) | BX571856; |
| Q6G8A3 | HEMH_STAAS | hemH SAS1754 | 4.99.1.1 | Ferrochelatase (EC 4.99.1.1) (Heme synthase) (Protoheme ferro-lyase) | BX571857; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| P64126 | HEMH_STAAW | hemH MW1773 | Staphylococcus aureus (strain MW2) | 4.99.1.1 | Ferrochelatase (EC 4.99.1.1) (Heme synthase) (Protoheme ferro-lyase) | BA000033; |
| Q5HNA5 | HEMH_STAEQ | hemH SERP1367 | Staphylococcus epidermidis (strain ATCC 35984/RP62A) | 4.99.1.1 | Ferrochelatase (EC 4.99.1.1) (Heme synthase) (Protoheme ferro-lyase) | CP000029; |
| Q8CNS1 | HEMH_STAES | hemH SE_1512 | Staphylococcus epidermidis (strain ATCC 12228) | 4.99.1.1 | Ferrochelatase (EC 4.99.1.1) (Heme synthase) (Protoheme ferro-lyase) | AE015929; |
| Q49YM6 | HEMH_STAS1 | hemH SSP0966 | Staphylococcus saprophyticus subsp. saprophyticus (strain ATCC 15305/DSM 20229) | 4.99.1.1 | Ferrochelatase (EC 4.99.1.1) (Heme synthase) (Protoheme ferro-lyase) | AP008934; |
| Q82KJ6 | HEMH_STRAW | hemH SAV_2407 | Streptomyces avermitilis | 4.99.1.1 | Ferrochelatase (EC 4.99.1.1) (Heme synthase) (Protoheme ferro-lyase) | BA000030; |
| O50533 | HEMH_STRCO | hemH SCO5859 SC9B10.26 | Streptomyces coelicolor | 4.99.1.1 | Probable ferrochelatase (EC 4.99.1.1) (Heme synthase) (Protoheme ferro-lyase) | AL939125; |
| B1VXN6 | HEMH_STRGG | hemH SGR_1673 | Streptomyces griseus subsp. griseus (strain JCM 4626/NBRC 13350) | 4.99.1.1 | Ferrochelatase (EC 4.99.1.1) (Heme synthase) (Protoheme ferro-lyase) | AP009493; |
| B4SNS0 | HEMH_STRM5 | hemH Smal_3991 | Stenotrophomonas maltophilia (strain R551-3) | 4.99.1.1 | Ferrochelatase (EC 4.99.1.1) (Heme synthase) (Protoheme ferro-lyase) | CP001111; |
| Q8CWW4 | HEMH_STRMU | hemH hemZ SMU_2063 | Streptococcus mutans | 4.99.1.1 | Ferrochelatase (EC 4.99.1.1) (Heme synthase) (Protoheme ferro-lyase) | AE014133; |
| Q04KS4 | HEMH_STRP2 | hemH SPD_0895 | Streptococcus pneumoniae serotype 2 (strain D39/NCTC 7466) | 4.99.1.1 | Ferrochelatase (EC 4.99.1.1) (Heme synthase) (Protoheme ferro-lyase) | CP000410: |
| C1C6Y5 | HEMH_STRP7 | hemH SP70585_1048 | Streptococcus pneumoniae (strain 70585) | 4.99.1.1 | Ferrochelatase (EC 4.99.1.1) (Heme synthase) (Protoheme ferro-lyase) | CP000918; |
| B1IBG8 | HEMH_STRPI | hemH SPH_1111 | Streptococcus pneumoniae (strain Hungary19A-6) | 4.99.1.1 | Ferrochelatase (EC 4.99.1.1) (Heme synthase) (Protoheme ferro-lyase) | CP000936; |
| B8ZPG2 | HEMH_STRPJ | hemH SPN23F09340 | Streptococcus pneumoniae (strain ATCC 700669/Spain 23F-1) | 4.99.1.1 | Ferrochelatase (EC 4.99.1.1) (Heme synthase) (Protoheme ferro-lyase) | FM211187; |
| Q97R30 | HEMH_STRPN | hemH SP_1009 | Streptococcus pneumoniae | 4.99.1.1 | Ferrochelatase (EC 4.99.1.1) (Heme synthase) (Protoheme ferro-lyase) | AE005672; |
| B2IPG3 | HEMH_STRPS | hemH SPCG_0985 | Streptococcus pneumoniae (strain CGSP14) | 4.99.1.1 | Ferrochelatase (EC 4.99.1.1) (Heme synthase) (Protoheme ferro-lyase) | CP001033; |
| Q8DQ04 | HEMH_STRR6 | hemH spr0914 | Streptococcus pneumoniae (strain ATCC BAA-255/R6) | 4.99.1.1 | Ferrochelatase (EC 4.99.1.1) (Heme synthase) (Protoheme ferro-lyase) | AE007317; |
| C1CE03 | HEMH_STRPI | hemH SPJ_0949 | Streptococcus pneumoniae (strain JJA) | 4.99.1.1 | Ferrochelatase (EC 4.99.1.1) (Heme synthase) (Protoheme ferro-lyase) | CP000919; |
| C1CRD1 | HEMH_STRZT | hemH SPT_1062 | Streptococcus pneumoniae (strain Taiwan19F-14) | 4.99.1.1 | Ferrochelatase (EC 4.99.1.1) (Heme synthase) (Protoheme ferro-lyase) | CP000921; |
| Q30S35 | HEMH_SULDN | hemH Suden_0918 | Sulfurimonas denitrificans (strain ATCC 33889/DSM 1251) (Thiomicrospira denitrificans (strain ATCC 33889/DSM 1251)) | 4.99.1.1 | Ferrochelatase (EC 4.99.1.1) (Heme synthase) (Protoheme ferro-lyase) | CP000153; |
| B2V955 | HEMH_SULSY | hemH SYO3AOP1_0845 | Sulfurihydrogenibium sp. (strain YO3AOP1) | 4.99.1.1 | Ferrochelatase (EC 4.99.1.1) (Heme synthase) (Protoheme ferro-lyase) | CP001080; |
| Q67T48 | HEMH_SYMTH | hemH STH160 | Symbiobacterium thermophilum | 4.99.1.1 | Ferrochelatase (EC 4.99.1.1) (Heme synthase) (Protoheme ferro-lyase) | AP006840; |
| Q31S00 | HEMH_SYNE7 | hemH Synpcc7942_0137 | Synechococcus elongatus (strain PCC 7942) (Anacystis nidulans R2) | 4.99.1 | Ferrochelatase (EC 4.99.1.1) (Heme synthase) (Protoheme ferro-lyase) | CP000100; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| Q2JVK5 | HEMH_SYNJA | hemH CYA_1034 | *Synechococcus* sp. (strain JA-3-3-Ab) (*Cyanobacteria bacterium* Yellowstone A-Prime) | 4.99.1.1 | Ferrochelatase (EC 4.99.1.1) (Heme synthase) (Protoheme ferro-lyase) | CP000239; |
| Q2JHZ4 | HEMH_SYNJB | hemH CYB_2857 | *Synechococcus* sp. (strain JA-2-3B'a(2-13)) (*Cyanobacteria bacterium* Yellowstone B-Prime) | 4.99.1.1 | Ferrochelatase (EC 4.99.1.1) (Heme synthase) (Protoheme ferro-lyase) | CP000240; |
| B1XL79 | HEMH_SYNP2 | hemH SYNPCC7002_A2589 | *Synechococcus* sp. (strain ATCC 27264/PCC 7002/PR-6) | 4.99.1.1 | Ferrochelatase (EC 4.99.1.1) (Heme synthase) (Protoheme ferro-lyase) | CP000951; |
| Q5N2B2 | HEMH_SYNP6 | hemH syc1368_c | *Agmenellum quadruplicatum* (*Synechococcus* sp. (strain ATCC 27144/PCC 6301/SAUG 1402/1) (*Anacystis nidulans*) | 4.99.1.1 | Ferrochelatase (EC 4.99.1.1) (Heme synthase) (Protoheme ferro-lyase) | AP008231; |
| A5GJF5 | HEMH_SYNPW | hemH SynWH7803_0644 | *Synechococcus* sp. (strain WH7803) | 4.99.1.1 | Ferrochelatase (EC 4.99.1.1) (Heme synthase) (Protoheme ferro-lyase) | CT971583; |
| Q7U5G0 | HEMH_SYNPX | hemH SYNW1747 | *Synechococcus* sp. (strain WH8102) | 4.99.1.1 | Ferrochelatase (EC 4.99.1.1) (Heme synthase) (Protoheme ferro-lyase) | BX569693; |
| A5GS98 | HEMH_SYNR3 | hemH SynRCC307_0854 | *Synechococcus* sp. (strain RCC307) | 4.99.1.1 | Ferrochelatase (EC 4.99.1.1) (Heme synthase) (Protoheme ferro-lyase) | CT978603; |
| Q0I8L9 | HEMH_SYNS3 | hemH sync_2000 | *Synechococcus* sp. (strain CC9311) | 4.99.1.1 | Ferrochelatase (EC 4.99.1.1) (Heme synthase) (Protoheme ferro-lyase) | CP000435; |
| Q3ALP2 | HEMH_SYNSC | hemH Sync9605_0716 | *Synechococcus* sp. (strain CC9605) | 4.99.1.1 | Ferrochelatase (EC 4.99.1.1) (Heme synthase) (Protoheme ferro-lyase) | CP000110; |
| P54225 | HEMH_SYNY3 | hemH slr0839 | *Synechocystis* sp. (strain ATCC 27184/PCC 6803/N-1) | 4.99.1.1 | Ferrochelatase (EC 4.99.1.1) (Heme synthase) (Protoheme ferro-lyase) | BA000022; |
| C5BIF4 | HEMH_TERTT | hemH TERTU_4338 | *Teredinibacter turnerae* (strain ATCC 39867/T7901) | 4.99.1.1 | Ferrochelatase (EC 4.99.1.1) (Heme synthase) (Protoheme ferro-lyase) | CP001614; |
| Q9HLB8 | HEMH_THEAC | hemH Ta0311 | *Thermoplasma acidophilum* (strain ATCC 25905/DSM 1728/JCM 9062/NBRC 15155/AMRC-C165) | 4.99.1.1 | Ferrochelatase (EC 4.99.1.1) (Heme synthase) (Protoheme ferro-lyase) | AL445063; |
| Q8DGU6 | HEMH_THEEB | hemH tlr2216 | *Thermosynechococcus elongatus* (strain BP-1) | 4.99.1.1 | Ferrochelatase (EC 4.99.1.1) (Heme synthase) (Protoheme ferro-lyase) | BA000039; |
| Q72L32 | HEMH_THET2 | hemH TT_C0231 | *Thermus thermophilus* (strain HB27/ATCC BAA-163/DSM 7039) | 4.99.1.1 | Ferrochelatase (EC 4.99.1.1) (Heme synthase) (Protoheme ferro-lyase) | AE017221; |
| Q978U9 | HEMH_THEVO | hemH TV1316 TVG1357926 | *Thermoplasma volcanium* (strain ATCC 51530/DSM 4299/IFO 15438/JCM 9571/GSS1) | 4.99.1.1 | Ferrochelatase (EC 4.99.1.1) (Heme synthase) (Protoheme ferro-lyase) | BA000011; |
| Q31EG9 | HEMH_THICR | hemH Tcr_1864 | *Thiomicrospira crunogena* (strain XCL-2) | 4.99.1.1 | Ferrochelatase (EC 4.99.1.1) (Heme synthase) (Protoheme ferro-lyase) | CP000109; |
| Q3SHA3 | HEMH_THIDA | hemH Tbd_2033 | *Thiobacillus denitrificans* (strain ATCC 25259) | 4.99.1.1 | Ferrochelatase (EC 4.99.1.1) (Heme synthase) (Protoheme ferro-lyase) | CP000116; |
| B8GU82 | HEMH_THISH | hemH Tgr7_0266 | *Thioalkalivibrio* sp. (strain HL-EbGR7) | 4.99.1.1 | Ferrochelatase (EC 4.99.1.1) (Heme synthase) (Protoheme ferro-lyase) | CP001339; |
| Q10WR6 | HEMH_TRIEI | hemH Tery_4313 | *Trichodesmium erythraeum* (strain IMS101) | 4.99.1.1 | Ferrochelatase (EC 4.99.1.1) (Heme synthase) (Protoheme ferro-lyase) | CP000393; |
| Q83H94 | HEMH_TROW8 | hemH TW747 | *Tropheryma whipplei* (strain TW08/27) (Whipple's bacillus) | 4.99.1.1 | Ferrochelatase (EC 4.99.1.1) (Heme synthase) (Protoheme ferro-lyase) | BX251412; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| Q83FJ2 | HEMH_TROWT | hemH TWT_733 | Tropheryma whipplei (strain Twist) (Whipple's bacillus) | 4.99.1.1 | Ferrochelatase (EC 4.99.1.1) (Heme synthase) (Protoheme ferro-lyase) | AE014184; |
| Q9KTB6 | HEMH_VIBCH | hemH VC_0987 | Vibrio cholerae | 4.99.1.1 | Ferrochelatase (EC 4.99.1.1) (Heme synthase) (Protoheme ferro-lyase) | AE003852; |
| Q5E6Q7 | HEMH_VIBF1 | hemH VF_0794 | Vibrio fischeri (strain ATCC 700601/ ES114) | 4.99.1.1 | Ferrochelatase (EC 4.99.1.1) (Heme synthase) (Protoheme ferro-lyase) | CP000020; |
| B5FBZ6 | HEMH_VIBFM | hemH VFMJ11_0831 | Vibrio fischeri (strain MJ11) | 4.99.1.1 | Ferrochelatase (EC 4.99.1.1) (Heme synthase) (Protoheme ferro-lyase) | CP001139; |
| Q87RH3 | HEMH_VIBPA | hemH VP0823 | Vibrio parahaemolyticus | 4.99.1.1 | Ferrochelatase (EC 4.99.1.1) (Heme synthase) (Protoheme ferro-lyase) | BA000031; |
| B7VII4 | HEMH_VIBSL | hemH VS_2267 | Vibrio splendidus (strain LGP32) (Vibrio splendidus (strain Mel32)) | 4.99.1.1 | Ferrochelatase (EC 4.99.1.1) (Heme synthase) (Protoheme ferro-lyase) | FM954972; |
| Q8DFM2 | HEMH_VIBVU | hemH VV1_0187 | Vibrio vulnificus | 4.99.1.1 | Ferrochelatase (EC 4.99.1.1) (Heme synthase) (Protoheme ferro-lyase) | AE016795; |
| Q7MMR4 | HEMH_VIBVY | hemH VV1003 | Vibrio vulnificus (strain YJ016) | 4.99.1.1 | Ferrochelatase (EC 4.99.1.1) (Heme synthase) (Protoheme ferro-lyase) | BA000037; |
| Q8D226 | HEMH_WIGBR | hemH WIGBR5290 | Wigglesworthia glossinidia brevipalpis | 4.99.1.1 | Ferrochelatase (EC 4.99.1.1) (Heme synthase) (Protoheme ferro-lyase) | BA000021; |
| Q73FY6 | HEMH_WOLPM | hemH WD_1186 | Wolbachia pipientis wMel | 4.99.1.1 | Ferrochelatase (EC 4.99.1.1) (Heme synthase) (Protoheme ferro-lyase) | AE017196; |
| B3CLU1 | HEMH_WOLPP | hemH WP0751 | Wolbachia pipientis subsp. Culex pipiens (strain wPip) | 4.99.1.1 | Ferrochelatase (EC 4.99.1.1) (Heme synthase) (Protoheme ferro-lyase) | AM999887; |
| Q7M7P9 | HEMH_WOLSU | hemH WS2157 | Wolinella succinogenes | 4.99.1.1 | Ferrochelatase (EC 4.99.1.1) (Heme synthase) (Protoheme ferro-lyase) | BX571662; |
| Q5GRR7 | HEMH_WOLTR | hemH Wbm0719 | Wolbachia sp. subsp. Brugia malayi (strain TRS) | 4.99.1.1 | Ferrochelatase (EC 4.99.1.1) (Heme synthase) (Protoheme ferro-lyase) | AE017321; |
| C0R4L0 | HEMH_WOLWR | hemH WRi_011580 | Wolbachia sp. subsp. Drosophila simulans (strain wRi) | 4.99.1.1 | Ferrochelatase (EC 4.99.1.1) (Heme synthase) (Protoheme ferro-lyase) | CP001391; |
| Q8PEX0 | HEMH_XANAC | hemH XAC4220 | Xanthomonas axonopodis pv. citri (Citrus canker) | 4.99.1.1 | Ferrochelatase (EC 4.99.1.1) (Heme synthase) (Protoheme ferro-lyase) | AE008923; |
| Q8P3H6 | HEMH_XANCP | hemH XCC4095 | Xanthomonas campestris pv. campestris | 4.99.1.1 | Ferrochelatase (EC 4.99.1.1) (Heme synthase) (Protoheme ferro-lyase) | AE008922; |
| O57478 | HEMH_XENLA | fech | Xenopus laevis (African clawed frog) | 4.99.1.1 | Ferrochelatase, mitochondrial (EC 4.99.1.1) (Heme synthase) (Protoheme ferro-lyase) | AF036617; |
| B2I7H7 | HEMH_XYLF2 | hemH XfasM23_1664 | Xylella fastidiosa (strain M23) | 4.99.1.1 | Ferrochelatase (EC 4.99.1.1) (Heme synthase) (Protoheme ferro-lyase) | CP001011; |
| Q9PFU1 | HEMH_XYLFA | hemH XF_0566 | Xylella fastidiosa | 4.99.1.1 | Ferrochelatase (EC 4.99.1.1) (Heme synthase) (Protoheme ferro-lyase) | AE003849; |
| B0U456 | HEMH_XYLFM | hemH Xfasm12_1736 | Xylella fastidiosa (strain M12) | 4.99.1.1 | Ferrochelatase (EC 4.99.1.1) (Heme synthase) (Protoheme ferro-lyase) | CP000941; |
| Q87B82 | HEMH_XYLFT | hemH PD_1576 | Xylella fastidiosa (strain Temecula1/ ATCC 700964) | 4.99.1.1 | Ferrochelatase (EC 4.99.1.1) (Heme synthase) (Protoheme ferro-lyase) | AE009442; |
| P16622 | HEMH_YEAST | HEM15 YOR176W | Saccharomyces cerevisiae (strain ATCC 204508/S288c) (Baker's yeast) | 4.99.1.1 | Ferrochelatase, mitochondrial (EC 4.99.1.1) (Heme synthase) (Protoheme ferro-lyase) | J05395; X54514; Z75084; BK006948; |
| A1JNA4 | HEMH_YERE8 | hemH YE3088 | Yersinia enterocolitica serotype O:8/ biotype 1B (strain 8081) | 4.99.1.1 | Ferrochelatase (EC 4.99.1.1) (Heme synthase) (Protoheme ferro-lyase) | AM286415; |

TABLE 3-continued

Characterized Ferrochelatase Enzymes

| UniProtKB/SwissProt Accession No. | Entry Name | Gene Names | Organism | EC Number | Protein Names | EMBL Accession No. |
|---|---|---|---|---|---|---|
| P43413 | HEMH_YEREN | hemH | Yersinia enterocolitica | 4.99.1.1 | Ferrochelatase (EC 4.99.1.1) (Heme synthase) (Protoheme ferro-lyase) | Z47767; U46859; |
| A7FL85 | HEMH_YERP3 | hemH YpsIP31758_3053 | Yersinia pseudotuberculosis serotype O:1b (strain IP 31758) | 4.99.1.1 | Ferrochelatase (EC 4.99.1.1) (Heme synthase) (Protoheme ferro-lyase) | CP000720; |
| Q1C4Q0 | HEMH_YERPA | hemH YPA_2610 | Yersinia pestis bv. Antiqua (strain Antiqua) | 4.99.1.1 | Ferrochelatase (EC 4.99.1.1) (Heme synthase) (Protoheme ferro-lyase) | CP000308; |
| B2K6Z7 | HEMH_YERPB | hemH YPTS_1040 | Yersinia pseudotuberculosis serotype IB (strain PB1/+) | 4.99.1.1 | Ferrochelatase (EC 4.99.1.1) (Heme synthase) (Protoheme ferro-lyase) | CP001048; |
| Q8ZC98 | HEMH_YERPE | hemH YPO3117 y1066 YP_0813 | Yersinia pestis | 4.99.1.1 | Ferrochelatase (EC 4.99.1.1) (Heme synthase) (Protoheme ferro-lyase) | AL590842; AE009952; AE017042; |
| A9R0Q8 | HEMH_YERPG | hemH YpAngola_A2895 | Yersinia pestis bv. Antiqua (strain Angola) | 4.99.1.1 | Ferrochelatase (EC 4.99.1.1) (Heme synthase) (Protoheme ferro-lyase) | CP000901; |
| Q1CL26 | HEMH_YERPN | hemH YPN_0972 YP516_1054 | Yersinia pestis bv. Antiqua (strain Nepal516) | 4.99.1.1 | Ferrochelatase (EC 4.99.1.1) (Heme synthase) (Protoheme ferro-lyase) | CP000305; ACNQ01000008; |
| A4TPA3 | HEMH_YERPP | hemH YPDSF_2753 | Yersinia pestis (strain Pestoides F) | 4.99.1.1 | Ferrochelatase (EC 4.99.1.1) (Heme synthase) (Protoheme ferro-lyase) | CP000668; |
| Q05338 | HEMH_YERPS | hemH YPTB0997 | Yersinia pseudotuberculosis | 4.99.1.1 | Ferrochelatase (EC 4.99.1.1) (Heme synthase) (Protoheme ferro-lyase) | BX936398; AF461770; |
| B1JHN0 | HEMH_YERPY | hemH YPK_3193 | Yersinia pseudotuberculosis serotype O:3 (strain YPIII) | 4.99.1.1 | Ferrochelatase (EC 4.99.1.1) (Heme synthase) (Protoheme ferro-lyase) | CP000950; |
| P57779 | HEMH_ZYMMO | hemH ZMO0303 | Zymomonas mobilis | 4.99.1.1 | Ferrochelatase (EC 4.99.1.1) (Heme synthase) (Protoheme ferro-lyase) | AF212041; AE008692; |

Suitable ferrochelatases of the present invention can also be identified by homology or sequence identity to the ferrochelatases disclosed in Table 3. Suitable ferrochelatases include those having an amino acid or nucleotide sequence identity of at least about 25 percent, more preferably at least about 30 to 40 percent, more preferably at least 50 to 60 percent, more preferably at least about 70 to 80 percent, most preferably at least about 85 to 95 percent as compared to a characterized ferrochelatase sequence of Table 3.

Mutant or modified ferrochelatase enzymes that retain their enzymatic activity (i.e., capable of catalyzing the insertion of ferrous iron into protoporphyrin IX to form protoheme (EC 4.99.1.1)) are also suitable for use in the present invention. Modifications or mutations to known ferrochelatase nucleotide sequences, such as nucleotide deletions, insertions, or substitutions that do not alter the coding sequence of the active region of the ferrochelatase enzyme or do not alter the activity of the encoded ferrochelatase enzyme are suitable for use in the methods of the present invention. For example, eukaryotic ferrochelatases possess an amino-terminus signal sequence that is lacking in prokaryote ferrochelatases (Dailey et al., "Ferrochelatase at the Millennium: Structures, Mechanisms, and [2Fe-2S] Clusters," *Cell. Mol. Life. Sci.* 57:1909-1926 (2000) which is hereby incorporated by reference in its entirety). Therefore, recombinant eukaryotic ferrochelatase sequences containing modifications or deletions to this portion of the encoded protein that do not alter enzyme activity are suitable for use in the present invention. Likewise, eukaryotic ferrochelatases also possess a carboxyl-terminal extension sequence that is lacking in a majority of prokaryotic ferrochelatases (Dailey et al., "Ferrochelatase at the Millennium: Structures, Mechanisms, and [2Fe-2S] Clusters," *Cell. Mol. Life. Sci.* 57:1909-1926 (2000), which is hereby incorporated by reference in its entirety). Recombinant eukaryotic ferrochelatase sequences containing modifications or deletions to this extension region are also suitable for use in the methods of the present invention. Similarly, recombinant ferrochelatase sequences containing single-base mutations that do not alter the conserved amino acid residues of the ferrochelatase protein acids (Dailey et al., "Ferrochelatase at the Millennium: Structures, Mechanisms, and [2Fe-2S] Clusters," *Cell. Mol. Life. Sci.* 57:1909-1926 (2000), which is hereby incorporated by reference in its entirety) or the enzyme active site are also suitable for use in the present invention.

In accordance with this aspect of the invention, co-expression of the recombinant heme-binding protein and ferrochelatase protein, or polypeptide thereof, is carried out in the presence of one or more heme precursors, Suitable heme precursors include, without limitation, δ-amino levulinic acid, succinyl CoA, glycine, glutamate, glutamate-1 semialdehyde, porphobilinogen, hydroxymethylbilane, and protoporphyrin.

Co-expression of the recombinant heme-binding protein and ferrochelatase protein or polypeptide can be carried out in any one of the commonly known systems that are available in the art for heterologous protein expression, including, without limitation, eukaryotic and prokaryotic expression systems, and cell-free translation systems as described herein.

Techniques and protocols for manipulation of nucleic acids, including, for example, the preparation of nucleic acid constructs, mutagenesis, sequencing, introduction of DNA into cells and gene expression, and analysis of proteins, are described in detail in *Current Protocols in Molecular Biology*, Ausubel et al. eds., (1992), which is hereby incorporated by reference in its entirety.

Typically, a nucleic acid molecule encoding all or part of a protein of interest, i.e., a heme-binding protein, is obtained using methods such as those described herein. The protein-encoding nucleic acid sequence is cloned into an expression vector that is suitable for the particular host cell of interest using standard recombinant DNA procedures. Suitable expression vectors include those which contain replicon and control sequences that are derived from species compatible with the host cell.

Expression vectors include (among other elements) regulatory sequences (e.g., promoters) that can be operably linked to the desired protein-encoding nucleic acid molecule to cause the expression of such nucleic acid molecule in the host cell. Together, the regulatory sequences and the protein-encoding nucleic acid sequence are an expression construct. Expression vectors may also include an origin of replication, marker genes that provide phenotypic selection in transformed cells, one or more other promoters, and a polylinker region containing several restriction sites for insertion of heterologous nucleic acid sequences.

Expression vectors useful for expression of heterologous protein(s) in a multitude of host cells are well known in the art (Sambrook and Russell, *Molecular Cloning: a Laboratory Manual* 3rd ed. (2001), which is hereby incorporated by reference in its entirety), and some specific examples are provided herein. The host cell is transfected with (or infected with a virus containing) the expression vector using any method suitable for the particular host cell. Such transfection methods are also well known in the art and non-limiting exemplary methods are described herein. The transfected (also called, transformed) host cell is capable of expressing the protein encoded by the corresponding nucleic acid sequence in the expression construct. Transient or stable transfection of the host cell with one or more expression vectors is contemplated by the present disclosure.

In one embodiment of the present invention, the nucleotide sequence encoding the desired heme-binding protein is inserted into one expression vector and the nucleotide sequence encoding the ferrochelatase is inserted into a second expression vector. In this embodiment, the two expression vectors are co-transfected into an appropriate host cell for transcription and translation. In another embodiment of the invention, both nucleotide sequences are inserted into one expression vector and the single expression vector encodes both the recombinant heme-binding protein and the recombinant ferrochelatase.

Many different types of cells may be used to express heterologous proteins, such as bacterial, archaeal, yeast, fungal, insect, vertebrate (such as mammalian cells), and plant cells, including primary cells and immortal cell lines. Numerous representatives of each cell type are commonly used and are available from a wide variety of commercial sources, including, for example, the American Tissue Culture Collection (ATCC). Further details of some specific embodiments are discussed below.

Prokaryotes, such as bacteria, may be used as host cells. Prokaryotic expression systems are advantageous, at least, because of culture affordability, ease of genetic manipulation, and high yields of desired product(s). As described herein, *E. coli* BL21 (DE3) is a suitable prokaryotic host cell. Other suitable *E. coli* host cells include, without limitation, *E. coli* K12 strain 94 (ATCC No. 31,446), coli strain W3 110 (ATCC No, 27,325), *E. coli* X1776 (ATCC No, 31,537), *E. coli* B, and many other strains, such as HB101, JM101, NM522, NM538, NM539, B1-21, B1-21 (DE3) pLysS, Origami B, OmpT-defective CD41, CD43 (DE3), and phosphatidylenthanolamine (PE)-deficient AD93. Similarly, other species and genera of prokaryotes including *Pseudomonas aeruginosa, Salmonella gastroenteritis (typhimirium), S. typhi, S. enteriditis, Shigella flexneri, S. sonnie, S. dysenteriae, Neisseria gonorrhoeae, N. meningitides, Haemophilus influenzae, H. pleuropneumoniae, Pasteurella haemolytica, P. multilocida, Legionella pneumophila, Treponema pallidum, T. denticola, T. orales, Borrelia burgdorferi, Borrelia* spp., *Leptospira interrogans, Klebsiella pneumoniae, Proteus vulgaris, P. morganii, P. mirabilis, Rickettsia prowazeki, R. typhi, R. richettsii, Porphyromonas (Bacteriodes) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A. salmonicida, Lactococcus lactis*, and *Yersinia pestis*, may all be used as prokaryotic expression hosts.

Prokaryotic host cells or other host cells with rigid cell walls may be transformed using any method known in the art, including, for example, calcium phosphate precipitation, or electroporation. Representative prokaryote transformation techniques are described in Hanahan et al., "Plasmid Transformation of *Escherichia coli* and Other Bacteria,"*Meth. Enzymol.*, 204:63-113 (1991), which is hereby incorporated by reference in its entirety.

Vectors typically used for transformation of *E. coli* include, without limitation, pBR322, pUC18, pUC19, pUC118, pUC119, Bluescript M13 and derivatives thereof. Numerous such plasmids are commercially available and are well known in the art.

Different genetic signals and processing events control many levels of gene expression (e.g., DNA transcription and messenger RNA ("mRNA") translation). Transcription of DNA is dependent upon the presence of a promoter, which is a DNA sequence that directs the binding of RNA polymerase, and thereby promotes mRNA synthesis. Promoters vary in their strength (i.e., their ability to promote transcription). For the purposes of expressing a cloned gene, it is desirable to use strong promoters to obtain a high level of transcription and, hence, expression. Therefore, depending upon the host system utilized, any one of a number of suitable promoters may also be incorporated into the expression vector carrying the nucleic acid molecule(s) of the present invention. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Recombinant heme-binding proteins can also be produced in archaeal expression systems. Species that are suitable for serving as hosts include, without limitation, *Methanosarcina acetivorans* and *Sulfolobus solfataricus* (see e.g., Albers et al., "Production of Recombinant and Tagged Proteins in the Hyerthermophilic Archaeon *Sulfolobus solfataricus,*" *Appl. Environ. Microbial.* 72(1):102-11 (2006) and Jonuscheit et al., "A Reporter Gene System for the Hyperthermophilic Archaean *Sulfolobus solfataricus* based on a Selectable and Integrative Shuttle Vector,"*Mol. Microbiol.* 48(5):1241-52 (2003), which is hereby incorporated by reference in its entirety).

Fungal protein expression systems can also be utilized in the methods of the present invention to efficiently produce a functional recombinant heme-binding protein. Fungal species are considered safer than animal cells because they pose little risk of contamination by viruses, prions, or endotoxins. Additionally, fungal systems are more efficient and economical than mammalian expression systems. There are several fungal species which have been used as hosts for the expression of recombinant proteins, including, without limitation, yeast (e.g., *Pichia pastoris, Kluyveromyces lactis*, and *Saccharomyces cerevisiae*), soil fungus (e.g., *Trichoderma reesei*), and black mould fungus (e.g., *Aspergillus niger*).

Yeast strains and yeast-derived vectors are used commonly for the expression of heterologous proteins. For instance, *Pichia pastoris* expression systems, may be used to co-express a recombinant heme-binding protein of interest with ferrochelatase (see e.g., Ballew N., "Revolutionizing Protein Production in Fungi," *Innovations in Pharmaceutical Technology* 70-76 (June 2004), which is hereby incorporated by reference in its entirety). Such systems include suitable *Pichia pastoris* strains, vectors, reagents, transformants, sequencing primers, and media. Available strains include KM71H (a prototrophic strain), SMD1168H (a prototrophic strain), and SMD1168 (a pep4 mutant strain) (Invitrogen).

*Saccharomyces cerevisiae* is also commonly used in heterologous expression systems. The plasmid YRp7 is commonly used as an expression vector in *Saccharomyces* (Stinchcomb et al., "Isolation and Characterization of a Yeast Chromosomal Replicator," *Nature* 282:39-43 (1979); Kingsman et al., "Replication in *Saccharomyces Cerevisiae* of Plasmid pBR313 Carrying DNA from the Yeast trp1 Region," *Gene* 7:141-152 (1979); and Tschemper et al., "Sequence of a Yeast DNA Fragment Containing a Chromosomal Replicator and the TRP1 Gene," *Gene* 10:157-166 (1980), which are hereby incorporated by reference in their entirety). This plasmid contains the trp1 gene that provides a selection marker for a mutant strain of yeast lacking the ability to grow in tryptophan, such as strains ATCC No. 44,076 and PEP4-1 (Jones, E. W., "Proteinase Mutants of *Saccharomyces cerevisiae,"* *Genetics* 85:23-33 (1977), which is hereby incorporated by reference in its entirety). The presence of the trp1 lesion as a characteristic of the yeast host cell genome then provides an effective environment for detecting transformation by growth in the absence of tryptophan.

Yeast host cells can be transformed using the polyethylene glycol method, as described by Hinnen (Hinnen et al., "Transformation of Yeast," *Proc. Natl. Acad. Sci. U.S.A.* 75:1929-1933 (1978), which is hereby incorporated by reference in its entirety). Additional yeast transformation protocols are set forth in Gietz et al., "Improved Method for High Efficiency Transformation of Intact Yeast Cells," *Nucl. Acids Res.* 20(6): 1425 (1992)) and Reeves et al. "A Yeast Intron as a Translation Terminator in a Plasmid Shuttle Vector," *Yeast Res.* 4(6): 573-597 (2004), which are hereby incorporated by reference in their entirety.

Suitable promoting sequences in yeast vectors include the promoters for 3-phosphoglycerate kinase (Hitzeman et al., "Isolation and Characterization of the Yeast 3-Phosphoglycerokinase Gene (PGK) by an Immunological Screening Technique," *J. Biol. Chem.* 255:12073-12080 (1980), which is hereby incorporated by reference in its entirety) or other glycolytic enzymes (Hess et al., "Cooperation of Glycolytic Enzymes," *J. Adv. Enzyme Reg.* 7:149-167 (1969) and Holland et al., "Isolation and Identification of Yeast Messenger Ribonucleic Acids Coding for Enolase, Glyceraldehyde-3-Phosphate Dehydrogenase, and Phosphoglycerate Kinase," *Biochem.* 17:4900-4907 (1978), which are hereby incorporated by referenced in their entirety), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression vectors, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Another representative eukaryotic expression system involves the recombinant baculoviruses, *Autographa californica* nuclear polyhedrosis virus (AcNPV; Summers and Smith, *A Manual of Methods for Baculovirus Vectors and Insect Cell Culture Procedures* Texas Agriculture Experiment Station. Bulletin No. 1555 (1987) and Luckow et al., "Trends in the Development of Baculovirus Expression Vectors," *Biotechnol.* 6:47-55 (1987), which are hereby incorporated by referenced in their entirety) and *Spodoptera frugiperda*. Baculoviruses do not infect humans and can therefore be safely handled in large quantities.

A baculovirus expression vector is prepared as previously described using standard molecular biology techniques. The vector may comprise the polyhedron gene promoter region of a baculovirus, the baculovirus flanking sequences necessary for proper crossover during recombination (the flanking sequences comprise about 200-300 base pairs adjacent to the promoter sequence) and a bacterial origin of replication which permits the construct to replicate in bacteria. In particular examples, the vector is constructed so that a heme-binding protein and ferrochelatase nucleic acid sequences are operably linked to the polyhedron gene promoter (collectively, the "expression construct") and the expression construct is flanked by the above-described baculovirus flanking sequences. Appropriate transfer vectors compatible with insect host cells are known in the art and include, without limitation, pVL1392, pVL1393, pAcGP67 and pAcSecG2T, which incorporate asecretory signal fused to the desired protein, and pAcGHLT and pAcHLT, which contain GST and 6×His tags (BD Biosciences, Franklin Lakes, N.J.).

Insect host cells (e.g., *Spodoptera frugiperda* cells) are infected with a recombinant baculovirus and cultured under conditions allowing expression of the baculovirus-encoded heme-binding proteins and ferrochelatase protein or polypeptide. When using insect cells, suitable baculovirus promoters include late promoters, such as 39K protein promoter or basic protein promoter, and very late promoters, such as the p10 and polyhedron promoters. In some cases it may be desirable to use transfer vectors containing multiple baculoviral promoters. The expressed heme-binding protein may be extracted from the insect cells using methods known in the art.

Mammalian host cells may also be used for heterologous expression of a heme-binding protein and ferrochelatase protein or polypeptide. Examples of suitable mammalian cell lines include, without limitation, monkey kidney CVI line transformed by SV40 (COS-7, ATCC CRL 1651); human embryonic kidney line 293S (Graham et al., "Characteristics of a Human Cell Line Transformed by DNA from Human Adenovirus Type 5," *J. Gen. Virol.* 36:59-74 (1977), which is hereby incorporated by reference in its entirety); baby hamster kidney cells (BHK, ATCC CCL-10); Chinese hamster ovary cells (Urlab et al., "Isolation of Chinese Hamster Cell Mutants Deficient in Dihydrofolate Reductase Activity." *Proc. Natl. Acad. Sci. U.S.A.* 77:4216-4220 (1980), which is hereby incorporated by reference in its entirety); mouse sertoli cells (TM4; Mather J. P., "Establishment and Characterization of Two Distinct Mouse Testicular Epithelial Cell Lines," *Biol. Reprod.* 23:243-252 (1980), which is hereby incorporated by reference in its entirety); monkey kidney cells (CVI-76, ATCC CCL-70); African green monkey kidney cells (VERO-76, ATCC CRL-1587); human cervical carcinoma cells (HELA, ATCC CCL-2); canine kidney cells (MDCK, ATCC CCL-34); buffalo rat liver cells (BRL 3A, ATCC CRL-1442); human lung cells (W138, ATCC CCL-75); human liver cells (Hep G2, HB 8065); mouse mammary tumor cells (MMT 060562, ATCC CCL-51); rat hepatoma cells (HTC, MI.54; Baumann ct al., "Dexamethasone Regulates the Program of Secretory Glycoprotein Synthesis in Hepatoma Tissue Culture Cells,"*J. Cell Biol.* 85:1-8 (1980), which is hereby incorporated by reference in its entirety); and TRI cells (Mather et al., "Culture of Testicular Cells in Hormone-Supplemented Serum-Free Medium," *Annals N.Y. Acad. Sci.* 383:44-68 (1982), which is hereby incorporated by reference in its entirety). Expression vectors for these cells ordinarily include (if necessary) DNA sequences for an origin of replication, a promoter located 5' of the nucleic acid sequence to be expressed, a ribosome binding site, an RNA splice site, a polyadenylation site, and/or a transcription terminator site.

Promoters used in mammalian expression vectors can be of viral origin. Such viral promoters may be derived from polyoma virus, adenovirus 2, and simian virus 40 (SV40). The SV40 virus contains two promoters that are termed the early and late promoters. These promoters are useful because they are both easily obtained from the virus as one nucleic acid fragment that also contains the viral origin of replication (Fiers et al., "Complete Nucleotide Sequence of SV40 DNA," *Nature* 273:113-120 (1978), which is hereby incorporated by reference in its entirety). Smaller or larger SV40 DNA fragments may also be used, provided they contain the approximately 250-bp sequence extending from the HindIII site toward the BglI site located in the viral origin of replication. Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., polyoma virus, adenovirus, VSV, BPV) and inserted into the expression vector. Alternatively, the origin of replication may be provided by the host cell chromosomal replication mechanism.

Cell-free translation systems are known in the art, and can be used to synthesize heme-binding proteins using the methods of the present invention (see e.g., Kurland, "Translational Accuracy In vitro," *Cell* 28:201-202 (1982) and Pavlov et al., "Rate of Translation of Natural mRNAs in an Optimized In vitro System,"*Arch. Biochem. Biophys.* 328:9-16 (1996); and Cell-Free Translation Systems, Spirin A. S., ed. (2002); *Cell-Free Protein Expression*, Swartz J. A., ed. (2003), which are hereby incorporated by reference in their entirety). The most frequently used cell-free translation systems consist of extracts from rabbit reticulocytes, wheat germ and *E. coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. Each extract is supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.) that facilitate the function of the particular translation machinery.

Either DNA or RNA, in plasmid or linear form, can be used as the starting material for cell-free protein synthesis. However, DNA starting material is necessarily transcribed to RNA using a "coupled" or "linked" system. A "linked" system generally involves DNA transcription with a bacteriophage polymerase followed by translation in the rabbit reticulocyte lysate or wheat germ lysate. Unlike eukaryotic systems (such as, rabbit reticulocyte or wheat germ) where transcription and translation occur sequentially, transcription and translation occur simultaneously in *E. coli* cell free systems. Thus. *E. coli* translation systems are "coupled" and can be performed in the same tube using either a DNA or RNA template. Methods of using *E. coli* cell-free systems have been described in detail (see e.g., Kigawa et al., "Cell-Free Production and Stable-Isotope Labeling of Milligram Quantities of Proteins," *FEBS Lett.* 442:15-19 (1999); Noren et al., "A General Method for Site-Specific Incorporation of Unnatural Amino Acids into Proteins," *Science* 244:182-188 (1989); Hanes et al., "In vitro Selection and Evolution of Functional Proteins by Using Ribosome Display," *Proc. Natl. Acad. Sci. U.S.A.* 94:4937-4942 (1997); Wilson et al., "The Use of mRNA Display to Select High-Affinity Protein-Binding Peptides," *Proc. Natl. Acad. Sci. U.S.A.* 98:3750-3755 (2001); and Sawasaki et al., "A Cell-Free Protein Synthesis System for High-Throughput Proteomics," *Proc. Natl. Acad. Sci. U.S.A.* 99(23):14652-14657 (2002), which are hereby incorporated by reference in their entirety). In the *E. coli* system, it may be advantageous to place a Shine-Dalgarno ribosome binding site upstream of the initiator codon in a DNA template. In particular examples, an *E. coli* S30 extract system allows expression from DNA vectors containing natural *E. coli* promoter sequences (such as lac or tac).

Another aspect of the present invention relates to a system for producing functional heme-binding proteins. This system comprises an expression system and one or more expression constructs encoding a recombinant heme-binding protein and a recombinant ferrochelatase.

Suitable expression systems are described above, including cell expression systems (e.g., bacterial, fungal, archaeal, and mammalian) and cell-free expression systems.

The expression constructs of the system will depend on the type of expression system. Suitable expression constructs are described supra. The expression constructs can be in linear form or contained in a plasmid or viral vector, and can further contain regulatory elements, such as a promoter sequence, a ribosome binding sequence, and a nucleic acid molecule encoding a termination sequence, to optimize protein expression. The system of the present invention can include one expression construct encoding both the recombinant heme-binding protein and ferrochelatase. Alternatively, the system can include a first expression construct encoding the recombinant heme-binding protein and a second expression construct encoding the recombinant ferrochelatase.

In accordance with this aspect of the invention, the system for producing functional heme-binding proteins further includes one or more heme precursors. Suitable precursors include δ-amino levulinic acid, succinyl CoA, glycine, glutamate, glutamate-1-semialdehyde, porphobilinogen, hydroxymethylbilane and protoporphyrin as described supra.

Another aspect of the present invention relates to a purified preparation of recombinant functional heme-binding protein.

In a preferred embodiment of the present invention, the purified preparation of functional recombinant heme-binding protein is prepared in accordance with the methods described supra. The purified preparation of recombinant heme-binding protein of the present invention has full heme incorporation and does not contain metal-free porphyrin. The purity of the preparation is assessed by the presence or absence of un-metallated heme, which can be measured by fluorescence spectroscopy and resonance Raman spectroscopy. In a preferred embodiment of the invention, the purified preparation of functional, recombinant heme-binding protein of the present invention is not fluorescent when excited at a wavelength of 397 nm and has a resonance Raman spectrum showing no evidence of free-base porphyrin incorporation (see Examples infra).

Purified preparations of heme-binding proteins of the present invention have a variety of therapeutic, research, and commercial utilities. With regard to therapeutic applications, purified preparations of hemoglobin are desired. Hemoglobin is a heme-binding protein responsible for carrying and delivering oxygen to tissues and organs in animals. Recombinant hemoglobin preparations are used as effective and safe oxygen carriers as an alternative to blood transfusion. A purified preparation of recombinant hemoglobin prepared in accordance with the methods of the present invention is fully functional due to full heme incorporation. Accordingly, the incorporation of a purified preparation of hemoglobin of the present invention into oxygen carrier and blood substitute technologies would improve the oxygen carrying capacity. Suitable oxygen carrier and blood substitute technologies include, without limitation, those disclosed in U.S. Pat. No. 4,412,989 to Iwashits et al., U.S. Pat. No. 6,022,849 to Olsen et al, U.S. Pat. No. 7,329,641 to Fronticellie et al., and U.S. Patent Publication No. 2006/0088583 to Takeoka et al., which are hereby incorporated by reference in their entirety.

Cytochrome P450s are a superfamily of enzymes that are critical to human drug metabolism. These proteins have been implicated in many clinical cases of adverse drug reaction and toxicity stemming from mechanism-based enzyme inhibition and drug-drug interactions. High-throughput assays that identify molecules that inhibit or induce CYP450 early in the drug development process are invaluable for guiding the elimination of candidate drugs that have unwanted metabolic properties and facilitating the production of better clinical candidates. Purified preparations of cytochrome P450 proteins of the present invention will benefit the variety of well established preclinical screening assays that are designed to predict drug metabolism and toxicity (see e.g., Trubetskoy et al., "Highly Minaturized Formats for In Vitro Drug Metabolism Assays Using Vivid Fluorescent Substrate and Recombinant Human Cytochrome P450 Enzymes," *J Bimolecular Screening* 56-66 (2005); Donato et al., "Fluorescence-Based Assays for Screening Nine Cytochrome P450 (P450) Activities in Intact Cells Expression Individual Human P450 Enzymes," *Drug Metab. Disposition* 32(7):699-706 (2004); Zhang et al., "Cytochrome P450 Reaction-Phenotyping: An Industrial Perspective," Expert Opin, Drug Metab. Toxicol. 3(5):667-87 (2007); Buters et al., "A Highly Sensitive Tool for the Assay of Cytochrome P450 Enzyme Activity in Rat, Dog, and Man: Direct Fluorescence Monitoring of the Deethylation of 7-ethoxy-4-trifluoromethylcoumarin," *Biochem. Pharm.* 46(20):1577-1584 (1993); and Yim et al., "A Continuous Spectrophotometric Assay for NADPH-cytochrome P450 Reductase Activity Using 3-(4,5-Dimethylthiazol-2-yl)-2,5-diphenyltetrazolium Bromide," *J. Biochem. Mol. Biol.* 38(3):366-369 (2005), which are hereby incorporated by reference in their entirety).

Purified preparations of nitric oxide synthases of the present invention also have therapeutic utility with regard to the treatment of vascular diseases, cancer, microbial infections, tissue injury, and neurological pathologies, and for promoting wound healing (see e.g., U.S. Pat. No. 5,658,565 to Billiar et al., U.S. Patent Publication No. 20070071725 to Paterson et al., and U.S. Patent Publication No. 20100087370 to Jain et al., which are hereby incorporated by reference in their entirety).

Purified preparations of cyclooxygenases (e.g. COX-1, COX-2, COX-3) of the present invention also have therapeutic/commercial utility. These enzymes mediate the formation of prostanoids, including prostaglandins, prostacyclin, and thromboxane. Pharmacological inhibition of these enzymes provides relief from the symptoms of inflammation and pain. Accordingly, purified preparations of cyclooxygenases made in accordance with the present invention can be used to screen and identify, using methods described infra, more potent inhibitors than the currently available non-steroidal anti-inflammatory drugs.

In addition to therapeutic utility, purified preparations of heme-binding proteins also have biotechnological utilities. For example, lignin peroxidase is a heme-binding protein that degrades plant lignin, a heterogenous aromatic polymer that encases the cellulose fibers of lignocellulose (see Weng et al., "Emerging Strategies in Lignin Engineering and Degradation for Cellulosic Biofuel Production," *Curr. Opin. Biotech.* 19:166-172 (2008), which is hereby incorporated by reference in its entirety). The lignocellulose content of plant biomass is a primary source of renewable carbon that can be used to produce bio-ethanol and chemical feedstocks for commercial use. A major obstacle to exploiting this renewable carbon source is the presence and degradation of lignin. Therefore, lignin degradation via lignin peroxidase, offers an attractive strategy for optimizing biofuel production (see e.g., U.S Patent Application Publication Nos. 2010/0291653 to Ness et al., 2010/0017916 to Pappan et al., 2005/0233423 to Berka et al., which are hereby incorporated by reference in their entirety). Accordingly, the present invention contemplates the use of a purified preparation of lignin peroxidase that does not contain metal-free porphyrin, for biofuel production.

Another aspect of the present invention relates to a method of identifying an agent that modulates activity of a heme-binding protein. This method involves providing a candidate agent and providing a recombinant functional heme-binding protein. This method further involves contacting the candidate agent with the recombinant functional heme-binding protein under conditions at which the functional heme-binding protein is active and comparing the activity of the functional heme-binding protein as a result of said contacting to the activity of the heme-binding protein alone, both under said conditions at which the heme-binding protein is active. A candidate agent that modulates the activity of a heme-binding protein is identified based on said comparing.

A related aspect of the present invention relates to a method of evaluating the metabolism of an agent by a heme-binding protein. This method involves providing a candidate agent and providing a recombinant functional heme-binding protein. This method further involves contacting the candidate agent with the recombinant functional heme-binding protein under conditions at which the functional heme-binding protein is active and comparing the activity of the functional heme-binding protein as a result of said contacting to the activity of the heme-binding protein alone, both under said conditions at which the heme-binding protein is active. The metabolism of the candidate agent by a heme-binding protein is evaluated based on said comparing.

In one embodiment of this aspect of the present invention, the above methods further involve providing a heme-binding protein substrate and/or one or more heme-binding protein co-factors, where the heme-binding protein substrate and/or heme-binding co-factor is present when the heme-binding protein is contacted with the candidate agent. The activity of the heme-binding protein in the presence of the one or more heme-binding cofactors with the heme-binding protein substrate is evaluated. In other words, the rate of metabolism or conversion of the heme-binding protein substrate by the heme-binding protein is a measure of heme-binding protein activity.

In accordance with this aspect of the present invention a decrease in the activity of the functional heme-binding protein in the presence of the candidate agent compared to in the absence of the candidate agent identifies an agent that modulates the heme-binding protein activity. In this regard, the candidate agent is an inhibitor of heme-binding protein activity. Activators of heme-binding protein activity can also be identified using this assay. An increase in heme-binding protein activity would identify candidate activators of heme-binding protein activity.

In accordance with aspects of the present invention directed to evaluating the metabolism of an agent by a heme-binding protein, an increase in the activity of a functional heme-binding protein in the presence of the candidate agent compared to in the absence of the candidate agent may identify an agent that is a substrate for heme-binding protein metabolism. Alternatively, a decrease in heme-binding protein activity may also indicate that the candidate agent is a substrate for the heme-binding protein activity (e.g., a substrate for cytochrome P450 metabolism). In this case, the observed decrease in heme-binding protein activity would result from competition for heme-protein binding between the heme-binding protein substrate and the candidate agent. In either case, metabolism of the candidate agent by the heme-binding protein can be further evaluated by analyzing the metabolic profile of the candidate agent using methods known in the art (e.g., high-performance liquid chromatography).

In accordance with these aspects of the present invention, the recombinant functional heme-binding protein does not contain metal-free porphyrin. Any of the heme-binding proteins described supra can be utilized in this aspect of the invention. In one embodiment of the present invention, the heme-binding protein is a cytochrome P450 protein. As noted above, the cytochrome P450 family of enzymes are the major catalysts for the oxidative metabolism of a vast array of hydrophobic chemicals. These enzymes are involved in the metabolism or biotransformation of endogenous as well as exogenous hydrophobic compounds. Since cytochrome P450-mediated metabolism influences drug clearance, toxicity, activation, and in some cases, adverse interaction with other drugs, accurately identifying agents that modulate cytochrome P450 activity or serve as substrates for metabolism is particularly important for early toxicological screening of candidate drugs. A number of cytochrome P450 screening assays are known in the art (see e.g., Donato et al., "Fluorescence-Based Assays for Screening Nine Cytochrome P450 (P450) Activities in Intact Cells Expression Individual Human P450 Enzymes," Drug Metab. Disposition 32(7):699-706 (2004); Zhang et al., "Cytochrome P450 Reaction-Phenotyping: An Industrial Perspective," Expert Opin. Drug Metab. Toxicol, 3(5):667-87 (2007); Buters et al., "A Highly Sensitive Tool for the Assay of Cytochrome P450 Enzyme Activity in Rat, Dog, and Man: Direct Fluorescence Monitoring of the Deethylation of 7-ethoxy-4-trifluoromethylcoumarin," Biochem, Pharm. 46(20):1577-1584 (1993); and Yim et al., "A Continuous Spectrophotometric Assay for NADPH-cytochrome P450 Reductase Activity Using 3-(4,5-Dimethylthiazol-2-yl)-2,5-diphenyltetrazolium Bromide," J. Biochem. Mol. Biol. 38(3066-369 (2005), which are hereby incorporated by reference in their entirety) and are commercially available, especially in high-throughput formats (see e.g. Promega. Invitrogen, and Agilent Technologies), all of which can be utilized in these aspects of the present invention, Incorporation of purified preparations of recombinant cytochrome P450 proteins of the present invention will enhance the accuracy of these and other P450 enzyme assays known and used in academic and pharmaceutical research arenas.

EXAMPLES

The following examples illustrate various methods for compositions in the treatment method of the invention. The examples are intended to illustrate, but in no way limit, the scope of the invention.
Materials and Methods for Examples 1-3:
Co-expression of Ferrochelatase with gsNOS. Ferrochelatase (FC) and gsNOS were expressed from the same pACYCduet vector (Novagen). To clone FC, genomic DNA was extracted from E. coli BL21(DE3) cells with the genomic DNA extraction kit from Epicenter. The FC gene was then PCR-amplified (Phusion polymerase, New England Biolabs) from the genomic DNA with primers that generated Nde1 and Xho1 sites at the 5' and 3' ends of the gene, respectively. A stop codon was introduced into the 3' primer before the Xho1 site to prevent C-terminal attachment of the vector-supplied S-tag. The amplified FC gene was then cloned into the Nde1 and Xho1 sites in Multiple Cloning Site-2 of the pACYCdtiet vector. The gene for gsNOS was derived from a previous pET28a-gsNOS plasmid (Sudhamsu et al., "Structure and Reactivity of a Thermostable Prokaryotic Nitric-Oxide Synthase that Forms a Long-Lived Oxy-Heme Complex," J. Biol. Chem. 281:9623-9632 (2006), which is hereby incorporated by reference in its entirety) by digesting the vector with Nco1 and Xho1 so as to include the His-tag and the thrombin cleavage site along with the coding sequence for gsNOS in the excised fragment. The Nco1-Xho1 fragment was then cloned into the pACYCduet-FC plasmid between the Nco1 and Sal1 sites. Sal1 and Xho1 produce compatible cohesive ends and thereby allow the His-tag, thrombin cleavage site and gsNOS fragment to be cloned between the Nco1 and Sal1 sites of Multiple cloning site-1 of the pACYCduct-FC plasmid. The resulting pACYCduet plasmid allows over-expression of gsNOS with a cleavable His-tag and FC with no tag, GsNOS was expressed and purified as reported before (Sudhamsu et al., "Structure and Reactivity of a Thermostable Prokaryotic Nitric-Oxide Synthase that Forms a Long-Lived Oxy-Heme Complex," J. Biol. Chem. 281:9623-9632 (2006), which is hereby incorporated by reference in its entirety). Co-expression of gsNOS and FC was also performed similarly to expression of gsNOS alone, although, a lesser amount of δ-ALA was added at the time of induction (10 mg/L versus 25 mg/L for gsNOS), and the growth media was supplemented with 100 μM $FeCl_3$. The antibiotics, chloramphenicol (34 μg/L) and kanamycin (50 μg/L), were added to the growth media of pACYCduet-gsNOS-FC and pET28a-gsNOS plasmids, respectively.

Co-expression of Ferrochelatase with BP450 and HBPAS. For co-expression of BP450 and HBPAS the same procedure was used. BP450 (NCBI: CBG70284) was cloned into pET151/D-TOPO (Invitrogen), a directional cloning vector with an N-terminal 6xHis-Tag followed by a TEV cleavage site and an ampicillin selectable marker. HBPAS (NCBI: NP_248866) was cloned into pET28a (Novagen) using NdeI and HindIII restriction sites, which included an N-terminal 6xHis-Tag followed by a thrombin cleavage site and a kanamycin selectable maker. Competent E. coli BL21 (DE3) cells containing FC/pACYCduet were transformed with either BP450/pET151/D-TOPO or HBPAS/pET28. Cells were grown at 37° C. in Luria broth containing 20 ug/mL Cm and 100 ug/L Amp (BP450) or 50 ug/L Kan (HBPAS) to an OD=0.6-0.8, Prior to induction with IPTG, the temperature was reduced to 17° C. and 25 mg/L d-ALA was added to the growth media. Cells were harvested 18-20 hrs after induction. An identical procedure with cells lacking the FC plasmid was used to express BP450 and HBPAS without FC. Both proteins were purified using Ni-NTA (Qiagen) chromatography techniques following the manufacturer's protocol. Furthermore, the proteins were purified to >95% purity using size exclusion chromatography after the removal of 6xHis.

Spectroscopy. Resonance Raman and UV-Visible spectra were recorded as described previously (Kabir et al., "Substrate-Ligand Interactions in Geobacillus Stearothermophilus Nitric Oxide Synthase," Biochem. 47:12389-12397 (2008), which is hereby incorporated by reference in its entirety).

Materials. Sodium chloride was obtained from Mallinkrodt, Ferric Chloride, IPTG and TRIS were from Fisher Scientific, Kanamycin, and Chloramphenicol from USBiological. δ-ALA was obtained from Sigma-Aldrich.

Example 1

UV-Vis Spectroscopy and SDS-PAGE Analysis of gsNOS

GsNOS (Geobacillus stearothermophihis Nitric Oxide Synthase) is a thermophilic enzyme that forms a highly stable heme-oxygen complex (Sudhamsu et al., "Structure and Reactivity of a Thermostable Prokaryotic Nitric-Oxide Synthase that Forms a Long-Lived Oxy-Heme Complex," J. Biol. Chem. 281:9623-9632 (2006), which is hereby incorporated by reference in its entirety) that has helped in identification of catalytic intermediates responsible for L-arginine oxidation to nitric oxide (Davydov et al., "EPR And ENDOR Characterization of the Reactive Intermediates in the Generation of NO by Cryoreduced Oxy-Nitric Oxide Synthase from G. Stearotherniophilus," J. Am. Chem. Soc. 131:14493-14507 (2009), which is hereby incorporated by reference in its entirety). In the over-expression of heme proteins the heme precursor δ-ALA is routinely added to the growth media when protein production is induced. Such δ-ALA supplementation results in complete heme incorporation for two other bacterial NOS proteins: *B. subtilis* NOS (Pant et al., "Structure of a Nitric Oxide Synthase Heme Protein from *Bacillus Subtilis*," *Biochem.* 41:11071-11079 (2002), which is hereby incorporated by reference in its entirety) and *D. radiodurans* NOS (Buddha et al., "Regioselective Nitration of Tryptophan by a Complex Between Bacterial Nitric-Oxide Synthase and Tryptophanyl-Trna Synthetase," *J. Biol. Chem.* 279:49567-49570 (2004), which is hereby incorporated by reference in its entirety). However, in what follows, it is shown that gsNOS over-expressed and purified from *E. coli* consists of two species: native heme-containing gsNOS, and gsNOS with protoporphyrin IX (free-base porphyrin) bound instead of heme. It was hypothesized that co-expression of ferrochelatase, the enzyme that metallates porphyrin would ameliorate this problem.

A UV-Vis spectroscopic analysis of gsNOS over-expressed in *E. coli* shows that the amount of heme incorporated with the protein changes from batch to batch, with the ratio of Soret peak height (403 nm) to protein peak height (280 nm) ($Abs_{403}/Abs_{280}$) varying between 0.25-0.40. Co-expression of FC with gsNOS increased $Abs_{403}/Abs_{280}$ to 0.6 (FIG. 1) in several (>3) different protein expression trials. Thus, gsNOS co-expressed with FC increases heme content of the protein in a consistent fashion.

Purified gsNOS, when over-expressed in *E. coli* with 25 mg/L δ-ALA added at the time of induction, results in two bands of ~42 kDa on SDS-PAGE (FIG. 1, Inset, lane A). Both bands shift on His-tag cleavage (FIG. 1, Inset, lane B), which indicates that both species represent recombinant gsNOS, with an intact N-terminus, but different gel mobilities. MALDI mass spectrometry of the sample shows only one sharp peak at a mass consistent with that of full-length gsNOS, which rules out proteolysis as the factor distinguishing the proteins represented in the two bands. Thus, the apparent difference in molecular weight on the gel of the two species (~3 kDa) may rather stem from a net charge difference. GsNOS, when co-expressed with FC from *E. coli* BL21 (DE3) cells, results in only a single species on SDS-PAGE (which corresponds to the lower band of the two observed previously; FIG. 1 Inset, lane C). On His-tag cleavage, this band shifts as a single species (FIG. 1, Inset, lane D). Protoporphyrin IX is the penultimate product in the heme biosynthesis pathway. FC catalyzes the last step in heme biosynthesis, i.e., insertion of an iron atom into protoporphyrin IX. Thus, the presence of two bands in the absence of FC coexpression suggests that protoporphyrin IX, rather than heme, has been incorporated into a substantial fraction of the sample.

Example 2

Resonance Raman and Fluorescence Analysis of gsNOS

Figures 2A, 2B:
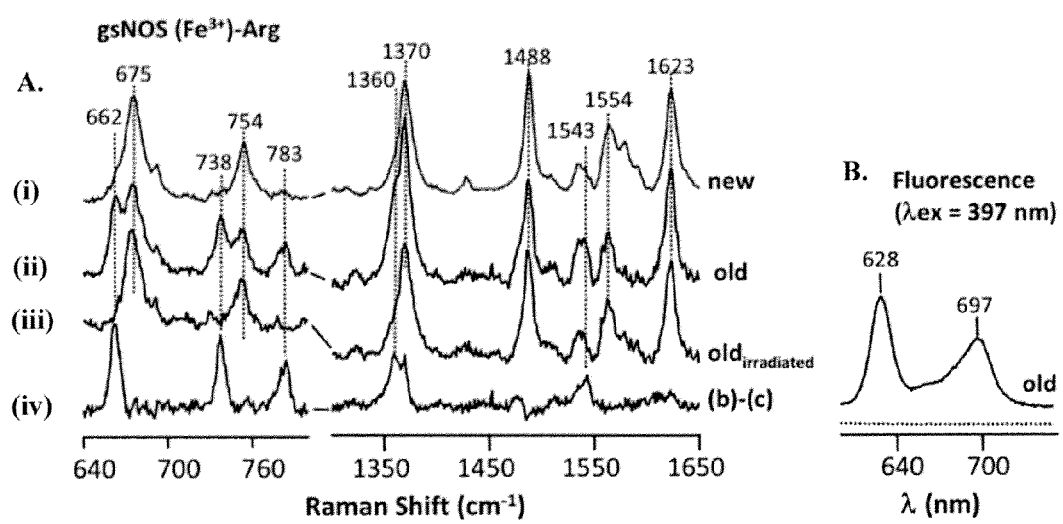
FIGS. 2A-2B are Resonance Raman and fluorescence spectra of recombinantly expressed gsNOS. The Resonance Raman spectra from gsNOS co-expressed with FC is shown as FIG. 2A(i), and gsNOS expressed by itself is depicted in FIGS. 2A(ii) and 2A(iii). The spectrum in FIG. 2A(ii) is obtained with 3 mW of 413.1 nm laser excitation with an acquisition time of 5 min. The spectrum in FIG. 2A(iii) is from the same sample as FIG. 2A(ii), but obtained after prolonged irradiation with 42 mW of 413.1 nm laser for two hours.

Confirmation of porphyrin incorporation into gsNOS came from resonance Raman studies of gsNOS in the presence of substrate L-arginine. A sample of gsNOS (expressed without FC) in the presence of substrate L-arginine, shows vibrational frequencies at 662 cm$^{-1}$, 738 cm$^{-1}$, 783 cm$^{-1}$, 1360 cm$^{-1}$ and 1543 cm$^{-1}$, apart from the typical vibrational frequencies that have been previously observed (Santolini et al., "Resonance Raman Study of *Bacillus Subtilis* NO Synthase-Like Protein: Similarities and Differences with Mammalian NO Synthases," *Biochem.* 45:1480-1489 (2006) and Rousseau et al., "Ligand-Protein Interactions in Nitric Oxide Synthase," *J. Inorganic Biochem.* 99:306-323 (2005), which are hereby incorporated by reference in their entirety) for other NOSs (FIG. 2B). These additional bands disappear after exposure to laser (FIG. 2C) and the subsequent difference spectrum (before and after laser exposure) highlights the original, additional resonances (FIG. 2D). The frequencies of these vibrations indicates the presence of free-base porphyrin in the protein sample (Blackwood et al., "Alternative Modes of Substrate Distortion in Enzyme and Antibody Catalyzed Ferrochelation Reactions," *Biochem.* 37:779-782 (1998) and Lu et al., "Binding of Protoporphyrin IX and Metal Derivatives to the Active Site of Wild-Type Mouse Ferrochelatase at Low Porphyrin-to-Protein Ratios," *Biochem.* 41:8253-8262 (2002), which are hereby incorporated by reference in their entirety). Furthermore, the enhanced photosensitivity of porphyrin compared to heme explains why the bands disappear after exposure (Blackwood et al., "Alternative Modes of Substrate Distortion in Enzyme and Antibody Catalyzed Ferrochelation Reactions," *Biochem.* 37:779-782 (1998) and Lu et al., "Binding of Protoporphyrin IX and Metal Derivatives to the Active Site of Wild-Type Mouse Ferrochelatase at Low Porphyrin-to-Protein Ratios," *Biochem.* 41:8253-8262 (2002), which are hereby incorporated by reference in their entirety). The presence of free base porphyrin is corroborated by the fluorescence spectrum of gsNOS (FIG. 2E), which when measured with excitation at 397 nm shows definitive characteristics of un-metallated heme (Lozovaya et al., "Protoporphyrin-IX as a Possible Ancient Photosensitizer—Spectral and Photochemical Studies," *Origins Of Life And Evolution Of The Biosphere* 20:321-330 (1990), which is hereby incorporate by reference in its entirety). Iron-bound heme is not fluorescent when excited at this wavelength. Incorporation of free-base porphyrin suggests that the last step of heme biosynthesis, i.e., Fe metallation to heme, which is performed by FC, cannot keep pace with protein folding and porphyrin incorporation. Co-expression of FC from *E. coli* with gsNOS and addition of 10 mg/L of δ-ALA of (60 μM, ~$0.50 per liter) generates a sample that is non-fluorescent and whose resonance Raman spectrum shows no evidence of porphyrin (FIG. 2A). Thus, under these conditions, the protein is fully heme incorporated.

Whether foregoing the addition of δ-ALA was also tested, while co-expressing FC would result in complete heme incorporation of gsNOS. The purified protein, which was checked for heme content by both SDS-PAGE and by UV-Vis spectroscopy had a higher degree of heme incorporation than under conditions of only adding δ-ALA (heme:protein ratio ~0.5); however, heme incorporation was not complete, Addition of a small amount of δ-ALA, (10 mg/L) is sufficient to make up for the slow rate of δ-ALA biosynthesis and produce fully incorporated protein in the presence of FC.

Example 3

FC-Assisted Heme Incorporation for a Bacterial P450 (BP450) and a Heme-Binding PAS Protein (HBPAS)

Figure 3:
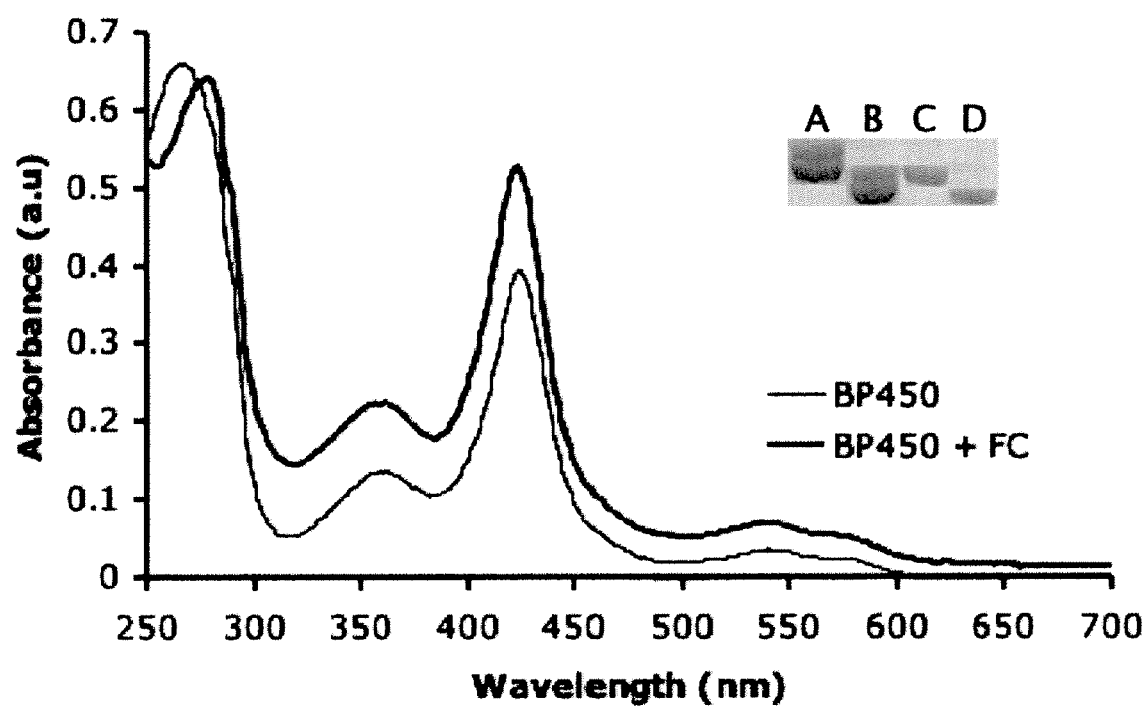
FIG. 3 shows the UV-Vis spectra of BP450 expressed by itself (thin line) and BP450 expressed with FC (thick line). Co-expression of FC results in a substantial increase in heme content of BP450 ($Abs_{Soret}/Abs_{280}$). The inset of FIG. 3 is an immunoblot showing that BP450 expressed alone also results in two bands (lane A), both of which shift on His-tag cleavage (lane B). BP450 co-expressed with FC results in one band (lane C), which shifts on His-tag cleavage as expected (lane D).
Figure 4:
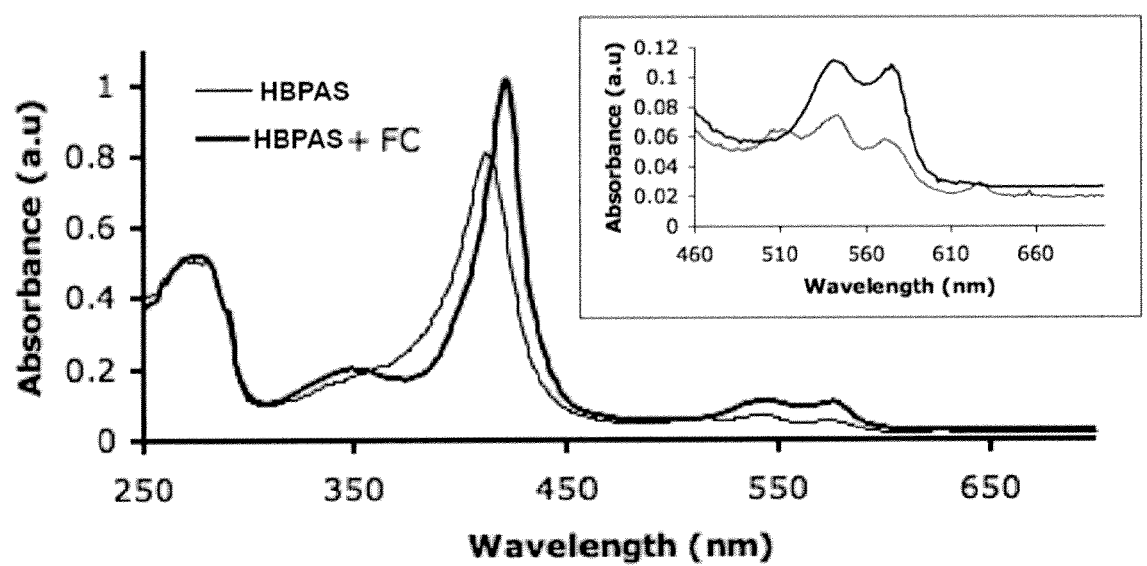
FIG. 4 shows the UV-Vis spectra of a Heme Binding PAS domain (HBPAS; His-ligated). When expressed by itself (thin line), the UV-Vis spectra of HBPAS shows four Q-hand absorption peaks (FIG. 4 inset). Co-expression with FC (thick line) increases the heme content and results in only two Q-bands (inset).
Figure 5:
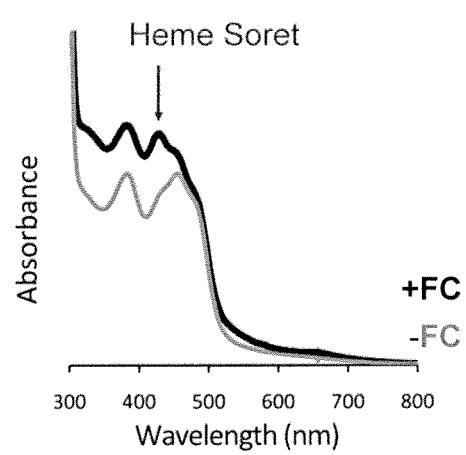
FIG. 5 shows the UV-Vis spectra of full-length NOS containing a reductase domain (>100 KdA). Under normal conditions of expression the Soret band indicative of heme incorporation is barely visible above the flavin absorption of the reductase component (gray trace), however, upon co-expression with ferrochelatase a strong Soret absorption peak (at ~416 nm), indicative of heme incorporation becomes apparent (black trace), Total yields of full-length NOS also increase in the presence of ferrochelatase.

In addition to gsNOS, FC also increases heme content to saturating levels in two other unrelated proteins: BP450, a Cys-ligated heme protein and HBPAS: a His-ligated heme protein. Both of these proteins, when over-expressed in *E. coli*, are produced with partial heme incorporation, UV-Vis spectra of purified BP450 and BP450 co-expressed with FC are strikingly different, with the increased intensity of the Soret peak indicative of greater heme content in the material produced along with FC (FIG. 3), When analyzed by SDS- PAGE, BP450 again also shows two bands (FIG. 3, Inset, lane A), which both shift on His-tag cleavage (FIG. 3, Inset, lane B). Like gsNOS, on co-expression with FC (FIG. 3, Inset, lane C) BP450 produces only one band, which shifts on His-tag cleavage (FIG. 3, Inset, lane D). In contrast, HBPAS always results in a single band on a SDS-PAGE gel, but shows absorption for four Q-bands in the UV-Vis spectrum when produced without FC (FIG. 4, thin line). Pure heme proteins show only two such bands. The extra band(s) are representative of protein bound protoporphyrin IX (Lozovaya et al., "Protoporphyrin-IX as a Possible Ancient Photosensitizer—Spectral and Photochemical Studies," *Origins Of Life And Evolution Of The Biosphere* 20:321-330 (1990), which is hereby incorporated by reference in its entirety). Co-expression of FC results in an increase in the $Abs_{(Soret)}/Abs_{(280)}$ and the extra Q-bands disappear (FIG. 4, thick line). The fluorescence spectrum of HBPAS without co-expression of FC is similar to that of gsNOS expressed without FC, but this fluorescence, attributable to protoporphyrin IX, also disappears on co-expression with FC.

Discussion of Examples 1-3

The production of δ-ALA is a rate-limiting step for heme biosynthesis (Ades, I. Z., "Heme Production in Animal-Tissues—The Regulation of Biogenesis of Delta-Aminolevulinate Synthase," *Internat. Biochem.* 22:565-578 (1990); Woodard et al., "Regulation of Heine-Biosynthesis in *Escherichia-Coli*," *Archives Biochem. Biophys.* 316:110-115 (1995); Gibson et al., "Is Delta-Aminolevulinic Acid Dehydratase Rate Limiting in Heme Biosynthesis Following Exposure of Cells to Delta-Aminolevulinic Acid?" *Photochem. Photobiol.* 73:312-317 (2001); and Heinemann et al., "The Biochemistry of Heme Biosynthesis," *Archives Biochem. Biophys.* 474:238-251 (2008), which are hereby incorporated by reference in their entirety) and δ-ALA synthesis is itself slowed by heme feedback inhibition. Thus, as has been well recognized (Ades, I. Z., "Heme Production in Animal-Tissues—The Regulation of Biogenesis of Delta-Aminolevulinate Synthase,"*Internat. J. Biochem.* 22:565-578 (1990); Woodard et al., "Regulation of Heme-Biosynthesis in *Escherichia-Coli*," *Archives Biochem. Biophys.* 316:110-115 (1995); Gibson et al., "Is Delta-Aminolevulinic Acid Dehydratase Rate Limiting in Heme Biosynthesis Following Exposure of Cells to Delta-Aminolevulinic Acid?" *Photochem. Photobtol.* 73:312-317 (2001); and Heinemann et al., "The Biochemistry of Heme Biosynthesis,"*Archives Biochem. Biophys.* 474:238-251 (2008), which are hereby incorporated by reference in their entirety), feeding with δ-ALA greatly aids recombinant heme protein production in *E. coli*. However, as demonstrated herein, under conditions of augmentation with δ-ALA, ferrous iron insertion into protoporphyrin IX becomes rate-limiting. Co-expression with ferrochelatase along with the addition of a small amount of δ-ALA, is sufficient to produce fully incorporated heme protein. This method is applicable for both Cys-ligated and His-ligated heme proteins. In the case of the two Cys-ligated proteins, porphyrin substitution could be observed on an SDS-PAGE gel as two closely spaced bands and also by fluorescence spectroscopy. In the one His-ligated heme protein example, UV-Visible and fluorescence spectra were effective indicators of insufficient porphyrin metallation, but only one band was observed by SDS-PAGE even with less than full porphyrin content. This is probably because the heme or porphyrin does not remain associated with the PAS protein during electrophoresis, unlike the other two cases.

In conclusion, the simple and inexpensive method of co-expressing ferrochelatase is effective at producing fully incorporated heme proteins in *E. coli*.

Example 4

FC-Assisted Heme Incorporation for Full-Length NOS

Co-expression of FC and full-length NOS was carried out as described supra. Under normal conditions of expression the Soret band indicative of heme incorporation is barely visible above the flavin absorption of the reductase component (gray trace), however, upon co-expression with ferrochelatase a strong Soret absorption peak (at ~416 nm), indicative of heme incorporation becomes apparent (black trace). Total yields of full-length NOS also increase in the presence of ferrochelatase as indicated by the overall greater cofactor absorption profile.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of producing a functional recombinant heme-binding protein comprising:
   providing an *Escherichia coli* host cell that expresses endogenous ferrochelatase protein;
   co-expressing in said host cell a non-native recombinant heme-binding protein and a recombinant ferrochelatase protein or a polypeptide thereof which retains iron insertion activity, wherein said host cell expresses both the endogenous ferrochelatase protein and the recombinant ferrochelatase protein or polypeptide thereof; and
   culturing said host cell under conditions effective for complete heme incorporation into the recombinantly produced heme-binding protein, thereby producing a functional heme-binding protein that does not contain metal-free porphyrin.

2. The method of claim 1, wherein said co-expressing is carried out in the presence of one or more heme precursors.

3. The method of claim 2, wherein the heme precursor is selected from the group consisting of δ-amino levulinic acid, succinyl CoA, glycine, glutamate, glutamate-1-semialdehyde, porphobilinogen, hydroxymethylbilane, and protoporphyrin.

4. The method of claim 1 further comprising:
   providing one or more expression vectors encoding the recombinant heme-binding protein and the recombinant ferrochelatase.

5. The method of claim 4, wherein the one or more expression vectors comprise one expression vector encoding both the recombinant heme-binding protein and the recombinant ferrochelatase.

6. The method of claim 4, wherein the one or more expression vectors comprise a first expression vector encoding the recombinant heme-binding protein and a second expression vector encoding ferrochelatase.

7. The method of claim 4, wherein the one or more expression vectors is selected from the group consisting of a bacterial expression vector, fungal expression vector, baculoviral expression vector, plant expression vector, archaeal expression vector, and mammalian expression vector.

8. The method of claim 1, wherein the heme-binding protein is a mammalian heme-binding protein.

9. The method of claim 1, wherein the heme-binding protein is a bacterial heme-binding protein.

10. The method of claim 1, wherein the heme-binding protein is a member of a class of heme-binding proteins selected from the group consisting of globins, cytochromes, bacterioferritins, hydroxylamine oxidoreductases, nitrophorins, peroxidases, cyclooxygenases, catalases, cytochromes P-450s, chloroperoxidases, PAS-domain heme sensors, H-NOX heme sensors, and nitric oxide synthases.

11. A system for producing functional heme-binding proteins comprising:
one or more expression constructs encoding a non-native recombinant heme-binding protein and a recombinant ferrochelatase and
an *Escherichia coli* host cell that expresses endogenous ferrochelatase protein and contains said one or more expression constructs.

12. The system of claim 11 further comprising:
one or more heme precursors.

13. The system of claim 12, wherein the one or more heme precursors is selected from the group consisting of δ-amino levulinic acid, succinyl CoA, glycine, glutamate, glutamate-1-semialdehyde, porphobilinogen, hydroxymethylbilane, and protoporphyrin.

14. The system of claim 11, wherein the one or more expression constructs further comprise a promoter sequence, a nucleic acid encoding a ribosome binding sequence, and a nucleic acid encoding a termination sequence.

15. The system of claim 11, wherein the one or more expression constructs is selected from the group consisting of a linear DNA construct, a plasmid vector, and a viral vector.

16. The system of claim 11, wherein the one or more expression constructs comprise one expression construct encoding both the recombinant heme-binding protein and the recombinant ferrochelatase.

17. The system of claim 11, wherein the one or more expression constructs comprise a first expression construct encoding the recombinant heme-binding protein and a second expression construct encoding the recombinant ferrochelatase.

18. The system of claim 11, wherein the one or more expression constructs is selected from the group consisting of a bacterial expression vector, fungal expression vector, baculoviral expression vector, plant expression vector, archaeal expression vector, and mammalian expression vector.

19. The system of claim 11, wherein the heme-binding protein is a mammalian heme-binding protein.

20. The system of claim 11, wherein the heme-binding protein is a bacterial heme-binding protein.

21. The system of claim 11, wherein the heme-binding protein is a member of a class of heme-binding proteins selected from the group consisting of cytochromes, bacterioferritins, hydroxylamine oxidoreductases, nitrophorins, peroxidases, cyclooxygenases, catalases, cytochromes P-450s, chloroperoxidases, globins, PAS-domain heme sensors, H-NOX heme sensors, and nitric oxide synthases.

22. The system of claim 11, wherein the system produces a functional heme-binding protein that does not contain metal-free porphyrin.

23. A method of producing a functional recombinant heme-binding protein comprising:
providing a bacterial or yeast host cell that expresses endogenous ferrochelatase protein;
co-expressing in said host cell (i) a non-native recombinant heme-binding protein that is a member of a class of heme-binding proteins selected from the group consisting of cytochrome P450s, PAS-domain heme sensors, and nitric oxide synthases, and (ii) a recombinant ferrochelatase protein or a polypeptide thereof which retains iron insertion activity, wherein said host cell expresses both the endogenous ferrochelatase protein and the recombinant ferrochelatase protein or polypeptide thereof; and
culturing said host cell under conditions effective for complete heme incorporation into the recombinantly produced heme-binding protein, thereby producing a functional heme-binding protein that does not contain metal-free porphyrin.

24. The method of claim 23, wherein said co-expressing is carried out in the presence of one or more heme precursors.

25. The method of claim 24, wherein the heme precursor is selected from the group consisting of δ-amino levulinic acid, succinyl CoA, glycine, glutamate, glutamate-1-semialdehyde, porphobilinogen, hydroxymethylbilane, and protoporphyrin.

26. The method of claim 23 further comprising:
providing one or more expression vectors encoding the recombinant heme-binding protein and the recombinant ferrochelatase.

27. The method of claim 26, wherein the one or more expression vectors comprise one expression vector encoding both the recombinant heme-binding protein and the recombinant ferrochelatase.

28. The method of claim 26, wherein the one or more expression vectors comprise a first expression vector encoding the recombinant heme-binding protein and a second expression vector encoding ferrochelatase.

29. The method of claim 26, wherein the one or more expression vectors is selected from the group consisting of a bacterial expression vector, fungal expression vector, baculoviral expression vector, plant expression vector, archaeal expression vector, and mammalian expression vector.

30. The method of claim 23, wherein the heme-binding protein is a mammalian heme-binding protein.

31. The method of claim 23, wherein the heme-binding protein is a bacterial heme-binding protein.

32. A system for producing functional heme-binding proteins comprising:
one or more expression constructs encoding (i) a non-native recombinant heme-binding protein that is a member of a class of heme-binding proteins selected from the group consisting of cytochrome P450s, PAS-domain heme sensors, and nitric oxide synthases, and (ii) a recombinant ferrochelatase and
a bacterial or yeast cell that expresses endogenous ferrochelatase protein and contains said one or more expression constructs.

33. The system of claim 32 further comprising:
one or more heme precursors.

34. The system of claim 32, wherein the one or more heme precursors is selected from the group consisting of δ-amino levulinic acid, succinyl CoA, glycine, glutamate, glutamate-1-semialdehyde, porphobilinogen, hydroxymethylbilane, and protoporphyrin.

35. The system of claim 32, wherein the one or more expression constructs further comprise a promoter sequence, a nucleic acid encoding a ribosome binding sequence, and a nucleic acid encoding a termination sequence.

36. The system of claim 32, wherein the one or more expression constructs is selected from the group consisting of a linear DNA construct, a plasmid vector, and a viral vector.

37. The system of claim 32, wherein the one or more expression constructs comprise one expression construct encoding both the recombinant heme-binding protein and the recombinant ferrochelatase.

38. The system of claim 32, wherein the one or more expression constructs comprise a first expression construct encoding the recombinant heme-binding protein and a second expression construct encoding the recombinant ferrochelatase.

39. The system of claim 32, wherein the one or more expression constructs is selected from the group consisting of a bacterial expression vector, fungal expression vector, baculoviral expression vector, plant expression vector, archaeal expression vector, and mammalian expression vector.

40. The system of claim 32, wherein the heme-binding protein is a mammalian heme-binding protein.

41. The system of claim 32, wherein the heme-binding protein is a bacterial heme-binding protein.

42. The system of claim 32, wherein the system produces a functional heme-binding protein that does not contain metal-free porphyrin.

* * * * *